US010213482B2

(12) United States Patent
Muller et al.

(10) Patent No.: US 10,213,482 B2
(45) Date of Patent: Feb. 26, 2019

(54) METHODS OF TREATING CHRONIC INFLAMMATORY DISEASES

(71) Applicants: Centre National de la Recherche Scientifique, Paris (FR); ImmuPharma France SA, Mulhouse (FR)

(72) Inventors: Sylviane Muller, Strasbourg (FR); Robert H. Zimmer, Mulhouse (FR); Jean-Paul Briand, Strasbourg (FR)

(73) Assignees: ImmuPharma France SA, Mulhouse (FR); Centre National De La Recherche Scientifique, Paris (FR)

( * ) Notice: Subject to any disclaimer, the term of this patent is extended or adjusted under 35 U.S.C. 154(b) by 0 days.

(21) Appl. No.: 14/966,679

(22) Filed: Dec. 11, 2015

(65) Prior Publication Data

US 2016/0166636 A1 Jun. 16, 2016

Related U.S. Application Data

(60) Provisional application No. 62/091,379, filed on Dec. 12, 2014.

(51) Int. Cl.
*A61K 38/17* (2006.01)
*C07K 14/47* (2006.01)

(52) U.S. Cl.
CPC .......... *A61K 38/1709* (2013.01); *C07K 14/47* (2013.01)

(58) Field of Classification Search
CPC .......................... A61K 38/1709; C07K 14/47
See application file for complete search history.

(56) References Cited

U.S. PATENT DOCUMENTS

| | | | |
|---|---|---|---|
| 4,522,811 A | 6/1985 | Eppstein et al. | |
| 5,527,688 A | 6/1996 | Mallia | |
| 5,541,291 A | 7/1996 | Keene | |
| 5,561,222 A | 10/1996 | Keene et al. | |
| 7,872,098 B1 | 1/2011 | Muller | |
| 7,884,184 B2 | 2/2011 | De Groot | |
| 2003/0186849 A1 | 10/2003 | Zimmer | |
| 2011/0223242 A1 | 9/2011 | Danicher et al. | |
| 2015/0111835 A1 | 4/2015 | Muller et al. | |

FOREIGN PATENT DOCUMENTS

| | | |
|---|---|---|
| DE | 204831 | 12/1983 |
| DE | 205340 | 12/1983 |
| FR | 2900341 | 11/2007 |
| JP | 2005512958 | 5/2005 |
| RU | 2214417 | 10/2003 |
| WO | WO 1995/025124 | 9/1995 |
| WO | WO 2000/020583 | 4/2000 |
| WO | WO 2003/020747 | 3/2003 |
| WO | WO 2003/025014 | 3/2003 |
| WO | WO 2013/088194 | 6/2013 |

OTHER PUBLICATIONS

Zarling, et al., "Phosphorylated peptides are naturally processed and presented by major histocompatability complex class I molecules in vivo", J. Exp. Med., 192:1755-1762 (2000).*
International Search Report and Written Opinion for PCT/EP2015/079395, dated Jan. 10, 2017.
Brand, D.D., Latham, K.A. & Rosloniec, E.F. (2007) Collagen-induced arthritis. Nature Protocols 2: 1269-1275.
Gros, F., Arnold, J., Page, N., Décossas, M., Korganow, A.-S., Martin, T. & Muller, S. (2012) Macroautophagy is deregulated in murine and human lupus T lymphocytes. Autophagy 8: 1113-1123.
Macri, C., Wang, F., Tasset, I., Schall, N., Page, N., Briand, J.-P., Cuervo A.M. & Muller, S. (2014) Modulation of deregulated chaperone-mediated autophagy by a phosphopeptide. Autophagy, in press.
Monneaux F., Hoebeke J., Sordet C., Nonn C., Briand J.-P., Maillère B., Sibillia J. & Muller S. (2005) Selective modulation of CD4+ T cells from lupus patients by a promiscuous, protective peptide analogue. J. Immunol.175: 5839-5847.
Monneaux F., Lozano J.M., Patarroyo M.E., Briand J.-P. & Muller S. (2003) T cell recognition and therapeutic effects of a phosphorylated synthetic peptide of the 70K snRNP protein administered in MRL/lpr lupus mice. Eur. J. Immunol. 33: 287-296.
Monneaux F., Parietti V., Briand J.P. & Muller S. (2004) Intramolecular T cell spreading in unprimed MRL/lpr mice: importance of the U1-70K protein sequence 131-151. Arthritis Rheum. 50: 3232-3238.
Monneaux F., Parietti V., Briand J.-P. & Muller S. (2007) Importance of spliceosomal RNP1 motif for intermolecular T-B cell spreading and tolerance restoration in lupus. Arthritis Res. Ther. 9: R111.
Muller S., Monneaux F., Schall N., Rashkov R.K., Oparanov B.A., Wiesel P., Geiger J.M. & Zimmer R. (2008) Spliceosomal peptide P140 for immunotherapy of systemic lupus erythematosus. Results of an early phase II clinical trial. Arthritis Rheum. 58: 3873-3883.
Muller, S. & Wallace D.J. (2014) The importance of implementing proper selection of excipients in lupus clinical trials. Lupus 23:609-614.
Muller, Sylviane: "Session Title: B cell Function and Targeting in Systemic Lupus Erythematosus Session Type: Abstract Submissions (ACR) Chaperone-Mediated Autophagy As a Target Of Therapeutic P140 Peptide Used In Lupus", Jan. 1, 2013 (Jan. 1, 2013), XP055330934, Retrieved from the Internet: URL:http://pdfcrowd.com/url_to_pdf/?use_pr int_media=1 [retrieved on Dec. 21, 2016] abstract.
Page N., Gros F., Schall N., Décossas M., Bagnard D., Briand J.-P. & Muller S. (2011) HSC70 blockade by the therapeutic peptide P140 affects autophagic processes and endogenous MHCII presentation in murine lupus. Ann. Rheum. Dis. 70:837-843.
Page N., Schall N., Strub J.-M., Quinternet M., Chaloin O., Décossas M., Cung M.-T., Van Dorsselaer A., Briand J.-P. & Muller S. (2009) The spliceosomal phosphopeptide P140 controls the lupus disease by interacting with the HSC70 protein and via a mechanism mediated by T cells. PloS ONE 4: e5273.

(Continued)

*Primary Examiner* — Robert S Landsman
*Assistant Examiner* — Bruce D. Hissong
(74) *Attorney, Agent, or Firm* — Bryan D. Zerhusen, Esq.; Cantor Colburn LLP

(57) ABSTRACT

The present invention relates to a peptide, or a salt thereof, comprising or consisting of the amino acid sequence IHM-VYSKRSGKPRGYAFIEY, comprising one or more post-translational modifications, for the treatment, prevention or amelioration of a hyper autophagy-related autoimmune disease or disorder.

16 Claims, 24 Drawing Sheets
Specification includes a Sequence Listing.

(56) References Cited

OTHER PUBLICATIONS

Schall, N. & Muller, S. (2014) "Resetting the autoreactive immune system with a therapeutic peptide in lupus" Lupus, in press (2015) 24, pp. 412-418.
Schall, N., Page., N., Macri, M., Chaloin, O., Briand, J.-P. & Muller, S. (2012) Peptide-based approaches to treat lupus and other autoimmune diseases. J. Autoimmunity 39: 143-153.
Wilhelm, M. & Muller, S. "Target autophagy as a novel therapeutic strategy in Autoimmune Diseases", Progress in Inflammation Resarch; Autophagy Networks in inflammation; Chapter Autoimmune diseases. Submitted, pp. 267-295.
Zimmer, R., Scherbarth, H.R., Rillo, O.L., Gomez-Reino, J. & Muller, S. (2013) Lupuzor/P140 peptide in patients with systemic lupus erythematosus: a randomised, double-blind, placebo-controlled phase IIb clinical trial. Ann. Rheum. Dis. 72: 1830-1835.
Alessandri et al., 2012 Alessandri C, Barbati C, Vacirca D, et al (2012) T lymphocytes from patients with systemic lupus erythematosus are resistant to induction of autophagy. FASEB J 26:4722-4732. doi: 10.1096/fj.12-206060.
Alirezaei et al., 2009 Alirezaei M, Fox HS, Flynn CT, et al (2009) Elevated ATG5 expression in autoimmune demyelination and multiple sclerosis. Autophagy 5:152-158. doi: 10.4161/auto.5.2.7348.
Anguiano et al., 2013 Anguiano J, Garner TP, Mahalingam M, et al (2013) Chemical modulation of chaperone-mediated autophagy by retinoic acid derivatives. Nat Chem Biol 9:374-382. doi: 10.1038/nchembio.1230.
Awan MUF, Deng Y (2014) Role of autophagy and its significance in cellular homeostasis. Appl Microbiol Biotechnol 98:5319-5328. doi: 10.1007/s00253-014-5721-8.
Baek K-H, Park J, Shin I (2012) Autophagy-regulating small molecules and their therapeutic applications. Chem Soc Rev 41:3245-3263. doi: 10.1039/c2cs15328a.
Bhattacharfya et al., 2014 Bhattacharya A, Parillon X, Zeng S, et al (2014) Deficiency of autophagy in dendritic cells protects against experimental autoimmune encephalomyelitis. J Biol Chem 289:26525-26532. doi: 10.1074/jbc.M114.575860.
Blum JS, Wearsch PA, Cresswell P (2013) Pathways of antigen processing. Annu Rev Immunol 31:443-473. doi: 10.1146/annurev-immunol-032712-095910.
Brun S, Beaino W, Kremer L, Taleb O, Mensah-Nyagan AG, Lam CD, Greer JM, De Seze J, Trifilieff T, 2015. Characterization a new rat model for chronic inflammatory demyelinating polyradiculoneuropathies. J. Neuroimmunol. 278: 1-10.
Burster T, Beck A, Tolosa E, et al (2004) Cathepsin G, and not the asparagine-specific endoprotease, controls the processing of myelin basic protein in lysosomes from human B lymphocytes. J Immunol 172:5495-5503. doi: 10.4049/jimmunol.172.9.5495.
Carrithers MD (2014) Update on Disease-Modifying Treatments for Multiple Sclerosis. Clin Ther. doi: 10.1016/j.clinthera.2014.08.006.
Cenci S (2014) Autophagy, a new determinant of plasma cell differentiation and antibody responses. Mol Immunol 62:289-295. doi: 10.1016/j.molimm.2014.02.008.
Cheong H, Lu C, Lindsten T, Thompson CB (2012) Therapeutic targets in cancer cell metabolism and autophagy. Nat Biotechnol 30:671-678. doi: 10.1038/nbt.2285.
Choi AMK, Ryter SW, Levine B (2013) Autophagy in human health and disease. N. Engl J Med 368:1845-1846. doi: 10.1056/NEJMc1303158.
Clarke AJ, Ellinghaus U, Cortini A, et al (2014) Autophagy is activated in systemic lupus erythematosus and required for plasmablast development. Ann Rheum Dis. doi: 10.1136/annrheumdis-2013-204343.
Codogno P, Mehrpour M, Proikas-Cezanne T (2012) Canonical and non-canonical autophagy: variations on a common theme of self-eating? Nat Rev Mol Cell Biol 13:7-12. doi: 10.1038/nrm3249.
Colbert JD, Matthews SP, Miller G, Watts C (2009) Diverse regulatory roles for lysosomal proteases in the immune response. Eur J Immunol 39:2955-2965. doi: 10.1002/eji.200939650.

Conway KL, Kuballa P, Khor B, et al (2013) ATG5 regulates plasma cell differentiation. Autophagy 9:528-537. doi: 10.4161/auto.23484.
Cuervo AM, Macian F (2014) Autophagy and the immune function in aging. Curr Opin Immunol 29:97-104. doi: 10.1016/j.coi.2014.05.006.
Cuervo AM, Wong E (2014) Chaperone-mediated autophagy: roles in disease and aging. Cell Res 24:92-104. doi: 10.1038/cr.2013.153.
Cuervo AM (2004) Autophagy: many paths to the same end. Mol Cell Biochem 263:55-72. doi: 10.1023IB:MCBI.0000041848.57020.57.
Dani et al., 2004 Dani A, Chaudhry A, Mukherjee P, et al (2004) The pathway for MHCII-mediated presentation of endogenous proteins involves peptide transport to the endo-lysosomal compartment. J Cell Sci 117:4219-4230. doi: 10.1242/jcs.01288.
Daubeuf et al., Bioprotocol, 645, 2013.
Daubeuf, F. and Frossard, N. 2012. Performing Bronchoalveolar Lavage in the Mouse. Curr Protoc Mouse Biol 2: 167-175.
Dengjel J, Schoor O, Fischer R, et al (2005) Autophagy promotes MHC class II presentation of peptides from intracellular source proteins. Proc Natl Acad Sci U S A 102:7922-7927. doi: 10.1073/pnas.0501190102.
Deretic V, Saitoh T, Akira S (2013) Autophagy in infection, inflammation and immunity. Nat Rev Immunol 13:722-737. doi: 10.1038/nri3532.
Deretic V (2012) Autophagy: an emerging immunological paradigm. J Immunol Baltim Md 1950 189:15-20. doi: 10.4049/jimmunol.1102108.
Dörfel et al., 2005 Dörfel D, Appel S, Grünebach F, et al (2005) Processing and presentation of HLA class I and II epitopes by dendritic cells after transfection with in vitro-transcribed MUC1 RNA. Blood 105:3199-3205. doi: 10.1182/blood-2004-09-3556.
Dowdle WE, Nyfeler B, Nagel J, et al (2014) Selective VPS34 inhibitor blocks autophagy and uncovers a role for NCOA4 in ferritin degradation and iron homeostasis in vivo. Nat Cell Biol 16:1069-1079. doi: 10.1038/ncb3053.
Ewald SE, Lee BL, Lau L, et al (2008) The ectodomain of Toll-like receptor 9 is cleaved to generate a functional receptor. Nature 456:658-662. doi: 10.1038/nature07405.
Feng Y, He D, Yao Z, Klionsky DJ (2014) The machinery of macroautophagy. Cell Res 24:24-41. doi: 10.1038/cr.2013.168.
Fernandez D, Bonilla E, Mirza N, et al (2006) Rapamycin reduces disease activity and normalizes T cell activation-induced calcium fluxing in patients with systemic lupus erythematosus. Arthritis Rheum 54:2983-2988. doi: 10.1002/art.22085.
Fleming A, Noda T, Yoshimori T, Rubinsztein DC (2011) Chemical modulators of autophagy as biological probes and potential therapeutics. Nat Chem Biol 7:9-17. doi: 10.1038/nchembio.500.
Glas J, Seiderer J, Bues S, et al (2013) IRGM variants and susceptibility to inflammatory bowel disease in the German population. PloS One 8:e54338. doi: 10.1371/journal.pone.0054338.
Gros F, Arnold J, Page N, et al (2012) Macroautophagy is deregulated in murine and human lupus T lymphocytes. Autophagy 8:1054-1053. doi: 10.4161/auto.20275.
Gros and Muller, 2014 Gros F, Muller S (2014) Pharmacological regulators of autophagy and their link with modulators of lupus disease. Br J Pharmacol 171:4337-4359. doi: 10.1111/bph.12792.
Gutierrez et al., 2004 Gutierrez MG, Master SS, Singh SB, et al (2004) Autophagy is a defense mechanism inhibiting BCG and *Mycobacterium tuberculosis* survival in infected macrophages. Cell 119:753-766. doi: 10.1016/j.cell.2004.11.038.
Hampe J, Franke A, Rosenstiel P, et al (2007) a genome-wide association scan of nonsynonymous SNPs identifies a susceptibility variant for Crohn disease in ATG16L1. Nat Genet 39:207-211. doi: 10.1038/ng1954.
Hanly JG (2014) Diagnosis and management of neuropsychiatric SLE. Nat Rev Rheumatol 10:338-347. doi: 10.1038/nrrheum.2014.15.
Harley JB, Alarcón-Riquelme ME, et al (2008) International Consortium for Systemic Lupus Erythematosus Genetics (SLEGEN), Genome-wide association scan in women with systemic lupus erythematosus identifies susceptibility variants in ITGAM, PXK, KIAA1542 and other loci. Nat Genet 40:204-210. doi: 10.1038/ng.81.

(56) References Cited

OTHER PUBLICATIONS

Hayter SM, Cook MC (2012) Updated assessment of the prevalence, spectrum and case definition of autoimmune disease. Autoimmun Rev 11:754-765. doi: 10.1016/j.autrev.2012.02.001.
He C, Klionsky DJ (2009) Regulation mechanisms and signaling pathways of autophagy. Annu Rev Genet 43:67-93. doi: 10.1146/annurev-genet-102808-114910.
Hong et al., 2004 Hong Z, Jiang Z, Liangxi W, et al (2004) Chloroquine protects mice from challenge with CpG ODN and LPS by decreasing proinflammatory cytokine release. Int Immunopharmacol 4:223-234. doi: 10.1016/j.intimp.2003.12.006.
HPLC; Neimark and Briand, 1993, "Development of a fully automated multichannel peptide synthesizer with integrated TFA cleavage capability" (Abstract).
Huss M, Wieczorek H (2009) Inhibitors of V-ATPases: old and new players. J Exp Biol 212:341-346. doi: 10.1242/jeb.024067.
Inglese and Petracca, 2014; Inglese M, Petracca M (2014) Therapeutic strategies in multiple sclerosis: A focus on neuroprotection and repair and relevance to schizophrenia. Schizophr Res. doi: 10.1016/j.schres.2014.04.040.
Jahreiss L, Menzies FM, Rubinsztein DC (2008) The itinerary of autophagosomes: from peripheral formation to kiss-and-run fusion with lysosomes. Traffic Cph Den 9:574-587. doi: 10.1111/j.1600-0854.2008.00701.x.
Järvinen TM, Hellquist A, Zucchelli M, et al (2012) Replication of GWAS-identified systemic lupus erythematosus susceptibility genes affirms B-cell receptor pathway signalling and strengthens the role of IRF5 in disease susceptibility in a Northern European population. Rheumatol Oxf Engl 51:87-92. doi: 10.1093/rheumatology/ker263.
Jeltsch-David and Muller, 2014). Jeltsch-David H, Muller S (2014) Neuropsychiatric systemic lupus erythematosus: pathogenesis and biomarkers. Nat Rev Neurol 10:579-596. doi: 10.1038/nrneurol.2014.148.
Jia and He, 2011 Jia W, He Y-W (2011) Temporal regulation of intracellular organelle homeostasis in T lymphocytes by autophagy. J Immunol 186:5313-5322. doi: 10.4049/jimmunol.1002404.
Jiang and Mizushima, 2014 Jiang P, Mizushima N (2014) Autophagy and human diseases. Cell Res 24:69-79. doi: 10.1038/cr.2013.161.
Jones et al., 2013 Jones SA, Mills KHG, Harris J (2013) Autophagy and inflammatory diseases. Immunol Cell Biol 91:250-258. doi: 10.1038/icb.2012.82.
Kang R, Zeh HJ, Lotze MT, Tang D (2011) The Beclin 1 network regulates autophagy and apoptosis. Cell Death Differ 18:571-580. doi: 10.1038/cdd.2010.191.
Kato et al., 2014 Kato M, Ospelt C, Gay RE, et al (2014) Dual role of autophagy in stress-induced cell death in rheumatoid arthritis synovial fibroblasts. Arthritis Rheumatol 66:40-48. doi: 10.1002/art.38190.
Kaushik S, Cuervo AM (2012) Chaperone-mediated autophagy: a unique way to enter the lysosome world. Trends Cell Biol 22:407-417. doi: 10.1016/j.tcb.2012.05.006.
Kawada M, Masuda T, Ishizuka M, Takeuchi T (2002) 15-Deoxyspergualin inhibits Akt kinase activation and phosphatidylcholine synthesis. J Biol Chem 277:27765-27771. doi: 10.1074/jbc.M200318200.
Kirkin et al. 2009 Kirkin V, McEwan DG, Novak I, Dikic I (2009) A role for ubiquitin in selective autophagy. Mol Cell 34:259-269. doi: 10.1016/j.molcel.2009.04.026.
Klionsky and Emr, 2000 Klionsky DJ, Emr SD (2000) Autophagy as a regulated pathway of cellular degradation. Science 290:1717-1721. doi: 10.1126/science.290.5497.1717.
Klionsky DJ, Elazar Z, Seglen PO, Rubinsztein DC (2008) Does bafilomycin A1 block the fusion of autophagosomes with lysosomes? Autophagy 4:849-850. doi: 10.4161/auto.6845.
Klionsky et al., 2012 Klionsky DJ, Abdalla FC, Abeliovich H, et al (2012) Guidelines for the use and interpretation of assays for monitoring autophagy. Autophagy 8:445-544. doi: 10.4161/auto.19496.

Konishi A, Arakawa S, Yue Z, Shimizu S (2012) Involvement of Beclin 1 in engulfment of apoptotic cells. J Biol Chem 287:13919-13929. doi: 10.1074/jbc.M112.348375.
Korolchuck et al., 2010 Korolchuk VI, Menzies FM, Rubinsztein DC (2010) Mechanisms of cross-talk between the ubiquitin-proteasome and autophagy-lysosome systems. FEBS Lett 584:1393-1398. doi: 10.1016/j.febslet.2009.12.047.
Kroemer G, Levine B (2008) Autophagic cell death: the story of a misnomer. Nat Rev Mol Cell Biol 9:1004-1010. doi: 10.1038/nrm2529.
Kuznik A, Bencina M, Svajger U, et al (2011) Mechanism of endosomal TLR inhibition by antimalarial drugs and imidazoquinolines. J Immunol 186:4794-4804. doi: 10.4049/jimmunol.1000702.
Lai Z-W, Borsuk R, Shadakshari A, et al (2013) Mechanistic target of rapamycin activation triggers IL-4 production and necrotic death of double-negative T cells in patients with systemic lupus erythematosus. J Immunol 191:2236-2246. doi: 10.4049/jimmunol.1301005.
Lamb et al., 2013 Lamb CA, Yoshimori T, Tooze SA (2013) the autophagosome: origins unknown, biogenesis complex. Nat Rev Mol Cell Biol 14:759-774. doi: 10.1038/nrm3696.
Lee E, Koo Y, Ng A, et al (2014) Autophagy is essential for cardiac morphogenesis during vertebrate development. Autophagy 10:572-587. doi: 10.4161/auto.27649.
Lee YH, Lee HS, Choi SJ, et al (2011) Efficacy and safety of tacrolimus therapy for lupus nephritis: a systematic review of clinical trials. Lupus 20:636-640. doi: 10.1177/0961203310389486.
Leung et al., 2010 Leung CS, Haigh TA, Mackay LK, et al (2010) Nuclear location of an endogenously expressed antigen, EBNA1, restricts access to macroautophagy and the range of CD4 epitope display. Proc Natl Acad Sci U S A 107:2165-2170. doi: 10.1073/pnas.0909448107.
Levine B, Kroemer G (2008) Autophagy in the pathogenesis of disease. Cell 132:27-42. doi: 10.1016/j.cell.2007.12.018.
Levine et al., 2011 Levine B, Mizushima N, Virgin HW (2011) Autophagy in immunity and inflammation. Nature 469:323-335. doi: 10.1038/nature09782.
Li et al., 2014 Li B, Yue Y, Dong C, et al (2014) Blockade of macrophage autophagy ameliorates activated lymphocytes-derived DNA induced murine lupus possibly via inhibition of proinflammatory cytokine production. Clin Exp Rheumatol 32:705-714.
Li J, Wang Z, Dai L, et al (2013) Effects of rapamycin combined with low dose prednisone in patients with chronic immune thrombocytopenia. Clin Dev Immunol 2013:548085. doi: 10.1155/2013/548085.
Li W, Zou W, Yang Y, et al (2012) Autophagy genes function sequentially to promote apoptotic cell corpse degradation in the engulfing cell. J Cell Biol 197:27-35. doi: 10.1083/jcb.201111053.
Lilienbaum et al., 2013 Lilienbaum A (2013) Relationship between the proteasomal system and autophagy. Int J Biochem Mol Biol 4:1-26.
Lin et al., 2013 Lin N-Y, Beyer C, Giessl A, et al (2013) Autophagy regulates TNFα-mediated joint destruction in experimental arthritis. Ann Rheum Dis 72:761-768. doi: 10.1136/annrheumdis-2012-201671.
Lleo A, Invernizzi P, Selmi C, et al (2007) Autophagy: highlighting a novel player in the autoimmunity scenario. J Autoimmun 29:61-68. doi: 10.1016/j.jaut.2007.06.003.
Lloyd, 2010 Lloyd TE (2010) Novel therapeutic approaches for inclusion body myositis. Curr Opin Rheumatol 22:658-664. doi: 10.1097/BOR.0b013e32833f0f4a.
Lorenz H-M, Grunke M, Wendler J, et al (2005) Safety of 15-deoxyspergualin in the treatment of glomerulonephritis associated with active systemic lupus erythematosus. Ann Rheum Dis 64:1517-1519. doi: 10.1136/ard.2005.035329.
Lorenz H-M, Schmitt WH, Tesar V, et al (2011) Treatment of active lupus nephritis with the novel immunosuppressant 15-deoxyspergualin: an open-label dose escalation study. Arthritis Res Ther 13:R36. doi: 10.1186/ar3268.
Lu XC, Tao Y, Wu C, et al (2013) Association between variants of the autophagy related gene—IRGM and susceptibility to Crohn's disease and ulcerative colitis: a meta-analysis. PloS One 8:e80602. doi: 10.1371/journal.pone.0080602.

(56) References Cited

OTHER PUBLICATIONS

Lui SL, Yung S, Tsang R, et al (2008) Rapamycin prevents the development of nephritis in lupus-prone NZB/W F1 mice. Lupus 17:305-313. doi: 10.1177/0961203307088289.
Majai G, Kiss E, Tarr T, et al (2014) Decreased apopto-phagocytic gene expression in the macrophages of systemic lupus erythematosus patients. Lupus 23:133-145. doi: 10.1177/0961203313511557.
Manoury B (2013) Proteases: Essential Actors in Processing Antigens and Intracellular Toll-Like Receptors. Front Immunol. doi: 10.3389/fimmu.2013.00299.
Manoury et al., 2002 Manoury B, Mazzeo D, Fugger L, et al (2002) Destructive processing by asparagine endopeptidase limits presentation of a dominant T cell epitope in MBP. Nat Immunol 3:169-174. doi: 10.1038/ni754.
Marchiando AM, Ramanan D, Ding Y, et al (2013) A deficiency in the autophagy gene Atg16L1 enhances resistance to enteric bacterial infection. Cell Host Microbe. doi: 10.1016/j.chom.2013.07.013.
Marino G, Niso-Santano M, Baehrecke EH, Kroemer G (2014) Self-consumption: the interplay of autophagy and apoptosis. Nat Rev Mol Cell Biol 15:81-94. doi: 10.1038/nrm3735.
Marquez RT, Xu L (2012) Bcl-2:Beclin 1 complex: multiple, mechanisms regulating autophagy/apoptosis toggle switch. Am J Cancer Res 2:214-221.
Matsumoto F, Saitoh S-I, Fukui R, et al (2008) Cathepsins are required for Toll-like receptor 9 responses. Biochem Biophys Res Commun 367:693-699. doi: 10.1016/j.bbrc.2007.12.130.
Matthews SP, Werber I, Deussing J, et al (2010) Distinct protease requirements for antigen presentation in vitro and in vivo. J Immunol 184:2423-2431. doi: 10.4049/jimmunol.0901486.
Miller BC, Zhao Z, Stephenson LM, et al (2008) The autophagy gene ATG5 plays an essential role in B lymphocyte development. Autophagy 4:309-314.
Mizumura K, Cloonan SM, Haspel JA, Choi AMK (2012) The emerging importance of autophagy in pulmonary diseases. Chest 142:1289-1299. doi: 10.1378/chest.12-0809.
Mizushima N, Yoshimori T, Levine B (2010) Methods in mammalian autophagy research. Cell 140:313-326. doi: 10.1016/j.cell.2010.01.028.
Mizushima N, Yoshimori T, Ohsumi Y (2011) The role of Atg proteins in autophagosome formation. Annu Rev Cell Dev Biol 27:107-132. doi: 10.1146/annurev-cellbio-092910-154005.
Mizushima N (2007) Autophagy: process and function. Genes Dev 21:2861-2873. doi: 10.1101/gad.1599207.
Molitoris JK, McColl KS, Swerdlow S, et al (2011) Glucocorticoid elevation of dexamethasone-induced gene 2 (Dig2/RTP801/REDD1) protein mediates autophagy in lymphocytes. J Biol Chem 286:30181-30189. doi: 10.1074/jbc.M111.245423.
Monneaux F, Briand JP, Muller S (2000) B and T cell immune response to small nuclear ribonucleoprotein particles in lupus mice: autoreactive CD4(+) T cells recognize a T cell epitope located within the RNP80 motif of the 70K protein. Eur J Immunol 30:2191-2200. doi: 10.1002/1521-4141(2000)30:8<2191::AID-IMMU2191>3.0.CO;2-R.
Monneaux F, Dumortier H, Steiner G, et al (2001) Murine models of systemic lupus erythematosus: B and T cell responses to spliceosomal ribonucleoproteins in MRL/Fas(lpr) and (NZB x NZW)F(1) lupus mice. Int Immunol 13:1155-1163. doi: 10.1093/intimm/13.9.1155.
Münz C (2012) Antigen processing for MHC class II presentation via autophagy. Front Antigen Present Cell Biol 3:9. doi: 10.3389/fimmu.2012.00009.
Murthy et al., 2014 Murthy A, Li Y, Peng I, et al (2014) A Crohn's disease variant in Atg16l1 enhances its degradation by caspase 3. Nature 506:456-462. doi: 10.1038/nature13044.
Nedjic J, Aichinger M, Emmerich J, et al (2008) Autophagy in thymic epithelium shapes the T-cell repertoire and is essential for tolerance. Nature 455:396-400. doi: 10.1038/nature07208.
Neefjes et al., 2011 Neefjes J, Jongsma MLM, Paul P, Bakke O (2011) Towards a systems understanding of MHC class I and MHC class II antigen presentation. Nat Rev Immunol 11:823-836. doi: 10.1038/nri3084.

Nogalska A, D'Agostino C, Terracciano C, et al (2010) Impaired autophagy in sporadic inclusion-body myositis and in endoplasmic reticulum stress-provoked cultured human muscle fibers. Am J Pathol 177:1377-1387. doi: 10.2353/ajpath.2010.100050.
Ohshima J, Lee Y, Sasai M, et al (2014) Role of mouse and human autophagy proteins in IFN-γ-induced cell-autonomous responses against Toxoplasma gondii. J Immunol 192:3328-3335. doi: 10.4049/jimmunol.1302822.
Okamoto K (2014) Organellophagy: eliminating cellular building blocks via selective autophagy. J Cell Biol 205:435-445. doi: 10.1083/jcb.201402054.
Oliva and Cenci, 2014 Oliva L, Cenci S (2014) Autophagy in plasma cell pathophysiology. Front Immunol 5:103. doi: 10.3389/fimmu.2014.00103.
Orozco et al., 2011 Orozco G, Eyre S, Hinks A, et al (2011) Study of the common genetic background for rheumatoid arthritis and systemic lupus erythematosus. Ann Rheum Dis 70:463-468. doi: 10.1136/ard.2010.137174.
Oshumi, 2014 Ohsumi Y (2014) Historical landmarks of autophagy research. Cell Res 24:9-23. doi: 10.1038/cr.2013.169.
Paludan et al., 2005 Paludan C, Schmid D, Landthaler M, et al (2005) Endogenous MHC class II processing of a viral nuclear antigen after autophagy. Science 307:5.
Pampliega O, Orhon I, Patel B, et al (2013) Functional interaction between autophagy and ciliogenesis. Nature 502:194-200. doi: 10.1038/nature12639.
Park et al., 2008 Park B, Brinkmann MM, Spooner E, et al (2008) Proteolytic cleavage in an endolysosomal compartment is required for activation of Toll-like receptor 9. Nat Immunol 9:1407-1414. doi: 10.1038/ni.1669.
Pengo et al., 2013 Pengo N, Scolari M, Oliva L, et al (2013) Plasma cells require autophagy for sustainable immunoglobulin production. Nat Immunol 14:298-305. doi: 10.1038/ni.2524.
Pierdominici et al., 2012 Pierdominici M, Vomero M, Barbati C, et al (2012) Role of autophagy in immunity and autoimmunity, with a special focus on systemic lupus erythematosus. FASEB J 26:1400-412. doi: 10.1096/fj.11-194175.
Pierdominici et al., 2014 Pierdominici M, Barbati C, Vomero M, et al (2014) Autophagy as a pathogenic mechanism and drug target in lymphoproliferative disorders. FASEB J 28:524-535. doi: 10.1096/fj.13-235655.
Pua et al., 2009 Pua HH, Guo J, Komatsu M, He Y-W (2009) Autophagy is essential for mitochondrial clearance in mature T lymphocytes. J Immunol 182:4046-4055. doi: 10.4049/jimmunol.0801143.
Puleston and Simon, 2013 Puleston DJ, Simon AK (2014) Autophagy in the immune system. Immunology 141:1-8. doi: 10.1111/imm.12165.
Ravikumar et al., 2010 Ravikumar B, Sarkar S, Davies JE, et al (2010) Regulation of mammalian autophagy in physiology and pathophysiology. Physiol Rev 90:1383-1435. doi: 10.1152/physrev.00030.2009.
Renna et al., 2010 Renna M, Jimenez-Sanchez M, Sarkar S, Rubinsztein DC (2010) Chemical inducers of autophagy that enhance the clearance of mutant proteins in neurodegenerative diseases. J Biol Chem 285:11061-11067. doi: 10.1074/jbc.R109.072181.
Rose NR, Bona C (1993) Defining criteria for autoimmune diseases (Witebsky's postulates revisited). Immunol Today 14:426-430. doi: 10.1016/0167-5699(93)90244-F.
Rubinsztein et al., 2012 Rubinsztein DC, Codogno P, Levine B (2012) Autophagy modulation as a potential therapeutic target for diverse diseases. Nat Rev Drug Discov 11:709-730. doi: 10.1038/nrd3802.
Ryter SW, Mizumura K, Choi AMK (2014) The impact of autophagy on cell death modalities. Int J Cell Biol 2014:502676. doi: 10.1155/2014/502676.
Saitoh and Akira, 2010 Saitoh T, Akira S (2010) Regulation of innate immune responses by autophagy-related proteins. J Cell Biol 189:925-935. doi: 10.1083/jcb.201002021.
Saitoh T, Fujita N, Jang MH, et al (2008) Loss of the autophagy protein Atg16L1 enhances endotoxin-induced IL-1beta production. Nature 456:264-268. doi: 10.1038/nature07383.

(56) References Cited

OTHER PUBLICATIONS

Sandri M, Coletto L, Grumati P, Bonaldo P (2013) Misregulation of autophagy and protein degradation systems in myopathies and muscular dystrophies. J Cell Sci 126:5325-5333. doi: 10.1242/jcs.114041.
Schall N, Muller S (2014) Resetting the autoreactive immune system with a therapeutic peptide in lupus. Lupus. In press.
Shen S, Kepp O, Kroemer G (2012) The end of autophagic cell death? Autophagy 8:1-3. doi: 10.4161/auto.8.1.16618.
Shibutani ST, Yoshimori T (2014) A current perspective of autophagosome biogenesis. Cell Res 24:58-68. doi: 10.1038/cr.2013.159.
Shoji-Kawata S, Sumpter R, Leveno M, et al (2013) Identification of a candidate therapeutic autophagy-inducing peptide. Nature 494:201-206. doi: 10.1038/nature11866.
Singh SB, Davis AS, Taylor GA, Deretic V (2006) Human IRGM induces autophagy to eliminate intracellular mycobacteria. Science 313:1438-1441. doi: 10.1126/science.1129577.
Staskiewicz L, Thorburn J, Morgan MJ, Thorburn A (2013) Inhibiting autophagy by shRNA knockdown: cautions and recommendations. Autophagy 9:1449-1450. doi: 10.4161/auto.24895.
Stephenson LM, Miller BC, Ng A, et al (2009) Identification of Atg5-dependent transcriptional changes and increases in mitochondrial mass in Atg5-deficient T lymphocytes. Autophagy 5:625-635. doi: 10.4161/auto.5.5.8133.
Stricher F, Macri C, Ruff M, Muller S (2013) HSPA8/HSC70 chaperone protein: structure, function, and chemical targeting. Autophagy 9:1937-1954. doi: 10.4161/auto.26448.
Stylianou K, Petrakis I, Mavroeidi V, et al (2011) The PI3K/Akt/mTOR pathway is activated in murine lupus nephritis and downregulated by rapamycin. Nephrol Dial Transplant 26:498-508. doi: 10.1093/ndt/gfq496.
Sumpter MD, Tatro LS, Stoecker WV, Rader RK (2012) Evidence for risk of cardiomyopathy with hydroxychloroquine. Lupus 21:1594-1596. doi: 10.1177/0961203312462757.
Temiz et al., 2009 Temiz P, Weihl CC, Pestronk A (2009) Inflammatory myopathies with mitochondrial pathology and protein aggregates. J Neurol Sci 278:25-29. doi: 10.1016/j.jns.2008.11.010.
Thomé R, Issayama LK, DiGangi R, et al (2014) Dendritic cells treated with chloroquine modulate experimental autoimmune encephalomyelitis. Immunol Cell Biol 92:124-132. doi: 10.1038/icb.2013.73.
Troncoso R, Paredes F, Parra V, et al (2014) Dexamethasone-induced autophagy mediates muscle atrophy through mitochondrial clearance. Cell Cycle 13:2281-2295. doi: 10.4161/cc.29272.
Tsvetkov AS, Miller J, Arrasate M, et al (2010) A small-molecule scaffold induces autophagy in primary neurons and protects against toxicity in a Huntington disease model. Proc Natl Acad Sci U S A 107:16982-16987. doi: 10.1073/pnas.1004498107.
Valdor et al., 2014 Valdor R, Mocholi E, Botbol Y, et al (2014) Chaperone-mediated autophagy regulates T cell responses through targeted degradation of negative regulators of T cell activation. Nat Immunol 15:1046-1054. doi: 10.1038/ni.3003.
Van Kasteren and Overkleeft, 2014 Van Kasteren SI, Overkleeft HS (2014) Endo-lysosomal proteases in antigen presentation. Curr Opin Chem Biol 23C:8-15. doi: 10.1016/j.cbpa.2014.08.011.
Vidal et al., 2014 Vidal RL, Matus S, Bargsted L, Hetz C (2014) Targeting autophagy in neurodegenerative diseases. Trends Pharmacol Sci. doi: 10.1016/j.tips.2014.09.002.
Villadangos et al., 1999 Villadangos JA, Bryant RA, Deussing J, et al (1999) Proteases involved in MHC class II antigen presentation. Immunol Rev 172:109-120. doi: 10.1111/j.1600-065X.1999.tb01360.x.
Xu et al., 2007 Xu Y, Jagannath C, Liu X-D, et al (2007) Toll-like receptor 4 is a sensor for autophagy associated with innate immunity. Immunity 27:135-144. doi: 10.1016/j.immuni.2007.05.022.
Xu et al., 2013 Xu K, Xu P, Yao J-F, et al (2013a) Reduced apoptosis correlates with enhanced autophagy in synovial tissues of rheumatoid arthritis. Inflamm Res 62:229-237. doi: 10.1007/s00011-012-0572-1.

Xu X, Kobayashi S, Chen K, et al (2013b) Diminished autophagy limits cardiac injury in mouse models of type 1 diabetes. J Biol Chem 288:18077-18092. doi: 10.1074/jbc.M113.474650.
Yamahara K, Yasuda M, Kume S, et al (2013) The role of autophagy in the pathogenesis of diabetic nephropathy. J Diabetes Res 2013:193757. doi: 10.1155/2013/193757.
Yamamoto A, Tagawa Y, Yoshimori T, et al (1998) Bafilomycin A1 prevents maturation of autophagic vacuoles by inhibiting fusion between autophagosomes and lysosomes in rat hepatoma cell line, H-4-II-E cells. Cell Struct Funct 23:33-42.
Yang et al., 2013 Yang W, Tang H, Zhang Y, et al (2013) Meta-analysis followed by replication identifies loci in or near CDKN1B, TET3, CD80, DRAM1, and ARID5B as associated with systemic lupus erythematosus in Asians. Am J Hum Genet 92:41-51. doi: 10.1016/j.ajhg.2012.11.018.
Yang Z, Klionsky DJ (2010) Eaten alive: a history of macroautophagy. Nat Cell Biol 12:814-822. doi: 10.1038/ncb0910-814.
Zhou et al., 2005 Zhou D, Li P, Lin Y, et al (2005) Lamp-2a facilitates MHC class II presentation of cytoplasmic antigens. Immunity 22:571-581. doi: 10.1016/j.immuni.2005.03.009.
Zhou et al., 2011 Zhou X, Lu X, Lv J, et al (2011) Genetic association of PRDM1-ATG5 intergenic region and autophagy with systemic lupus erythematosus in a Chinese population. Ann Rheum Dis 70:1330-1337. doi: 10.1136/ard.2010.140111.
Alete, et al., "Cell surface nucleolin on developing muscle is a potential ligand for the axonal receptor protein tyrosine phosphatese-σ", FEBS Journal, 273:4668-4681 (2006).
Andersen, et al., "Phosphorylated peptides can be transported by TAP molecules, presented by class I MHC molecules, and recognized by phosphorylated-specific CTL", J. Immuno. 163:3812-3818 (1999).
Anderton, "Peptide-based immunotherapy of autoimmunity: a path of puzzles, paradoxes and possibilities", Immunol. 104:367-376 (2001).
Arbuckle, et al., "Development of autoantibodies before the clinical onset of systemic lupus erythematosus", N. Engl. J. Med. 349(16):1526-1533 (2003).
Axen, "Chemical coupling of peptides and proteins to polysaccharides by means of cyanogen halides", et al., Nature, 214:1302 (1987).
Bates, et al., "Antiproliferative Activity of G-rich Oligonucleotides correlates with protein binding", J. Biol. Chem. 274, 26369 (1999).
Brahms, et al., "The C-terminal RG dipeptide repeats of the spliceosome Sm proteins D1 and D3 contain symmetrical dimethylarginines, which form a major B-cell epitope for anti-SM autoantibodies", J. Biol. Chem. 275:17122-17129 (2000).
Cambridge, et al., "B cell depletion therapy in systemic lupus erythaematosus: relationships among serum B lymphocyte stimulator levels, autoantibody profile and clinical response", Ann Rheum Dis 67:1011-1016 (2008).
Carpino, L.A., "1-hydroxy-7-azabenzotriazole. An efficient peptide coupling additive", J. Am. Chem Soc. 115:4397-4398 (1993).
Cui, et al., "Modulating protein activity and cellular function by methionine residue oxidation", Amino Acids 43:505-517 (2011).
D'Cruz, et al.,"Systemic lupus erythematosus", Lancet 369:587-596 (2007).
Egleton, et al., "Bioavailability and transport of peptides and peptide drugs into the brain", Peptides, 9:1431-1439 (1997).
Eilat, et al., "Prevention of systemic lupus erythematosus-like disease in (NZBxNZW)F1 mice by treating with CDR1- and CDR3-based peptides of a pathogenic autoantibody", J. Clin. Immunol. 20:268-278 (2000).
Ho, et al., "Comparing the effect on protein stability of methionine oxidation versus mutagenesis: steps toward engineering oxidative resistance in proteins", Protein Engineering, Oxford University Press, Surrey, GB, 14:343-347 (2001).
Hochberg, M.C., "The epidemiology of systemic lupus erythematosus⁽⁾", Rheum Dis Clin North Am 16:617-639 (1990).
Holman, "Partial purification and characterization of an extractible nuclear antigen which reacts with sle sera", Ann NY Acad. Sci. 124(2):800-806 (1965).
International Search Report, and Written Opinion, dated Jun. 4, 2012, for PCT/IB2011/003256, filed Dec. 13, 2011.

(56) References Cited

OTHER PUBLICATIONS

Jouanne, et al., "A peptide derived from a polyreactive monoclonal anti-DNA natural antibody modulate lupus development in (NZBxNZW)F1 mice"., Immunology 96:333-339 (1999).
Kaliyaperumal, et al., "Antigen-specific therapy of murine lupus nephritis using nucleosomal peptides: tolerance spreading impairs pathogenic function of autoimmune T and B cells", J. Immunol. 162:5775-5783 (1999).
Kattah, Nichole Hanick, "Tetramers reveal CD4+ T cells that are specific for UI-70 in systemic lupus erythematosus", Stanford University, Dept. of Immunology, doctoral dissertation (2010).
Klein-Gunnewiek, et al., "The U1 snRNP complex: an autoantigen in connective tissue disease", Clin. Exp. Rheumatol. 15:549-560 (1997).
Kreuter, et al., "Passage of peptides through the bood-brain barrier with colloidal polymer particles (nanoparticles)", Brain Res. 674:171-174 (1995).
Krust, et al., "The anti-HIV pentameric pseudopeptide HB-19 is preferentially taken up in vivo by lymphoid organs where it forms a complex with nucleolin", PNAS, 98(24):14090-14095, Nov. 20, 2001.
Lerner, et al., "Antibodies to small nuclear RNAs complexed with proteins are produced by patients with systemic lupus erythematosus", Proc Natl Acad Sci USA 76(11);5495-5499 (1979).
Lerner, et al., "Two novel classes of small ribonucleoproteins detected by antibodies associated with lupus erythematosus", Science 211(4480):400-402 (1981).
Luijten, KM., et al., "The Systemic Lupus Erythematosus Responder Index (SRI); A new SLE Disease Activity Asssessment", Autoimmun Rev. Mar. 2012: 11(5): 326-329.
Manning, et al., "Stability of protein pharmaceuticals: an update", Pharmaceutical research, Kluwer Academic Publishers-Plenum Publishers, NL, 27:544-575 (2010).
Marino, et al., "Prevention of systemic lupus erythematosus in MRL/Ipr mice by administration of an immunoglobulin-binding peptide", Nature Biotechn. 18:735-739 (2000).
Merrifield, R.B., "Solid phase peptide. I. The synthesis of a tetrapeptide", J. Am. Chem. Soc. 85:2149-2154 (1963).
Monneaux, et al., "Key sequence involved in the spreading of the systemic autoimmune response to spliceosomal proteins", Scand. J. Immunol. 54:45-54 (2001).
Monneaux, et al., "Laboratory protocols for the identification of Th cell epitopes on self antigens in mice with systemic autoimmune diseases", J. Immunol. Meth. 244:195-204 (2000).
Nath, et al., "Genetics of human systemic lupus erythematosus: the emerging picture", Curr. Opin. Immunol. 16(6):794-800 (2004).
Neimark, et al., "Development of a fully automated multichannel peptide synthesizer with integrated TFA cleavage capability", Pept Res. 6(4):219-228 (1993).

Nicolaus, B.J.R., "Symbiotic approach to drug design", Decision Making in Drug Research, New York, pp. 173-186 (1983).
Nisole, et al., "The Anti-HIV pentameric pseudopeptide HB-19 binds the c-terminal end of nucleolin and prevents anchorage of virus particles in the plasma membrane of target cells", J. Biological Chemistry 277(23)20877-20886, Jun. 7, 2002.
Nisole, et al., "The Anti-HIV pseudopeptide HB-19 forms a complex with the cell-surface-expressed nucleolin independent of heparan sulfate proteoglycans", J. Biological Chemistry 274(39):27875-27884, Sep. 24, 1999.
Nisole, et al., "The HB-19 pseudopeptide 5[Kψ($CH_2N$)PR]-TASP Inhibits attachment of T lymphocyte- and Macrophase-Tropic HIV to permissive cells", AIDS Res. Hum. Retroviruses 16(3):237-249, Feb. 10, 2000.
Northemann, et al., "Identification of an inhibitory element within the human 68-kDa (U1) ribonucleoprotein antigen", Prot. Exp. Purif. 6:748-756 (1995).
Okawa, et al., "Production of anti-peptide specific antibody in mice following immunization with peptides conjugated to mannan", J. Immunological Methods 149:127-131 (1992).
Orlando, M., "Modification of proteins and low molecular weight substance with hydroxyethyl starch (HES)", Inauguraldissertation, Geisen, p. 166 (2003).
Page et al., "A therapeutic peptide in lupus alters autophagic processes and stability of MHCII molecules in MRL/Ipr B cells", Autophagy 7(5):539-540 (2011).
Scofield, "Autoantibodies as predictors of disease", Lancet, 363:1544-1546 (2004).
Singh, et al., "Immune tolerance to autoantibody-derived peptides delays development of autoimmunity in murine lupus", J. Clin. Invest. 96:2990-2996 (1995).
Theissen, H., et al., "Cloning of the human complementary DNA for the U-1 RNA-Associated 70 K protein", EMBO (European Molecular Biology Organization) Journal, 5:3209-3218 (1986).
Uniprot Accession No. Q62376, (2001).
Utz, et al., "Posttranslational protein modifications, apoptosis, and the bypass of tolerance to autoantigens", Arthritis Rheum. 41:1152-1160 (1998).
Vogt, "Oxidation of methionyl residues in proteins: tools, targets, and reversal", Free Radical Biology & Medicine 18(1):93-105 (1995).
Wakeland, et al., "Delineating the Genetic Basis of Systemic Lupus Erythematosus", Immunity, 15(3):397-408 (2001).
Woppmann, et al., "Identification of an snRNP-associated kinase activity that phosphorylates arginine/serine rich domains typical of slicing factors", Nucleic Acids Res 21:2815-2822 (1993).
Xu, et al., "Inhibition of DNA replication and induction of S phase cell cycle arrest by G-rich oligonucleotides", J. Biol. Chem. 276, 43221 (2001).

* cited by examiner

SEQUENCE LISTING

```
<160> NUMBER OF SEQ ID NOS: 6

<210> SEQ ID NO 1
<211> LENGTH: 21
<212> TYPE: PRT
<213> ORGANISM: Artificial sequence
<220> FEATURE:
<223> OTHER INFORMATION: derived from U1 snRNP 70 kDa

<400> SEQUENCE: 1

Arg Ile His Met Val Tyr Ser Lys Arg Ser Gly Lys Pro Arg Gly Tyr
1               5                   10                  15

Ala Phe Ile Glu Tyr
            20

<210> SEQ ID NO 2
<211> LENGTH: 20
<212> TYPE: PRT
<213> ORGANISM: Artificial sequence
<220> FEATURE:
<223> OTHER INFORMATION: derived from U1 snRNP 70 kDa
```

```
<400> SEQUENCE: 2

Ile His Met Val Tyr Ser Lys Arg Ser Gly Lys Pro Arg Gly Tyr Ala
1               5                   10                  15

Phe Ile Glu Tyr
            20

<210> SEQ ID NO 3
<211> LENGTH: 437
<212> TYPE: PRT
<213> ORGANISM: Homo sapiens

<400> SEQUENCE: 3

Met Thr Gln Phe Leu Pro Pro Asn Leu Leu Ala Leu Phe Ala Pro Arg
1               5                   10                  15

Asp Pro Ile Pro Tyr Leu Pro Leu Glu Lys Leu Pro His Glu Lys
            20                  25                  30

His His Asn Gln Pro Tyr Cys Gly Ile Ala Pro Tyr Ile Arg Glu Phe
            35                  40                  45

Glu Asp Pro Arg Asp Ala Pro Pro Thr Arg Ala Glu Thr Arg Glu
    50                  55                  60

Glu Arg Met Glu Arg Lys Arg Glu Lys Ile Glu Arg Gln Gln
65                  70                  75                  80

Glu Val Glu Thr Glu Leu Lys Met Trp Asp Pro His Asn Asp Pro Asn
                85                  90                  95

Ala Gln Gly Asp Ala Phe Lys Thr Leu Phe Val Ala Arg Val Asn Tyr
            100                 105                 110

Asp Thr Thr Glu Ser Lys Leu Arg Glu Phe Glu Val Tyr Gly Pro
    115                 120                 125

Ile Lys Arg Ile His Met Val Tyr Ser Lys Arg Ser Gly Lys Pro Arg
130                 135                 140

Gly Tyr Ala Phe Ile Glu Tyr Glu His Glu Arg Asp Met His Ser Ala
145                 150                 155                 160

Tyr Lys His Ala Asp Gly Lys Lys Ile Asp Gly Arg Arg Val Leu Val
                165                 170                 175

Asp Val Glu Arg Gly Arg Thr Val Lys Gly Trp Arg Pro Arg Arg Leu
            180                 185                 190

Gly Gly Gly Leu Gly Gly Thr Arg Arg Gly Gly Ala Asp Val Asn Ile
        195                 200                 205

Arg His Ser Gly Arg Asp Asp Thr Ser Arg Tyr Asp Glu Arg Pro Gly
    210                 215                 220

Pro Ser Pro Leu Pro His Arg Asp Arg Asp Arg Asp Arg Glu Arg Glu
225                 230                 235                 240

Arg Arg Glu Arg Ser Arg Glu Arg Asp Lys Glu Arg Glu Arg Arg
                245                 250                 255

Ser Arg Ser Arg Asp Arg Arg Arg Ser Arg Ser Arg Asp Lys Glu
            260                 265                 270

Glu Arg Arg Arg Ser Arg Glu Arg Ser Lys Asp Lys Asp Arg Asp Arg
        275                 280                 285

Lys Arg Arg Ser Ser Arg Ser Arg Glu Arg Ala Arg Glu Arg Glu
    290                 295                 300

Arg Lys Glu Glu Leu Arg Gly Gly Gly Asp Met Ala Glu Pro Ser
305                 310                 315                 320

Glu Ala Gly Asp Ala Pro Pro Asp Asp Gly Pro Pro Gly Glu Leu Gly
                325                 330                 335
```

-continued

```
Pro Asp Gly Pro Asp Gly Pro Glu Glu Lys Gly Arg Asp Arg Asp Arg
            340                 345                 350

Glu Arg Arg Arg Ser His Arg Ser Glu Arg Arg Arg Arg Asp Arg
        355                 360                 365

Asp Arg Asp Arg Asp Arg Asp Arg Glu His Lys Arg Gly Glu Arg Gly
    370                 375                 380

Ser Glu Arg Gly Arg Asp Glu Ala Arg Gly Gly Gly Gly Gln Asp
385                 390                 395                 400

Asn Gly Leu Glu Gly Leu Gly Asn Asp Ser Arg Asp Met Tyr Met Glu
                405                 410                 415

Ser Glu Gly Gly Asp Gly Tyr Leu Ala Pro Glu Asn Gly Tyr Leu Met
            420                 425                 430

Glu Ala Ala Pro Glu
            435

<210> SEQ ID NO 4
<211> LENGTH: 21
<212> TYPE: PRT
<213> ORGANISM: Artificial sequence
<220> FEATURE:
<223> OTHER INFORMATION: derived from U1 snRNP 70 kDa
<220> FEATURE:
<221> NAME/KEY: MOD_RES
<222> LOCATION: (4)..(4)
<223> OTHER INFORMATION: OXIDATION
<220> FEATURE:
<221> NAME/KEY: MOD_RES
<222> LOCATION: (10)..(10)
<223> OTHER INFORMATION: PHOSPHORYLATION

<400> SEQUENCE: 4

Arg Ile His Met Val Tyr Ser Lys Arg Ser Gly Lys Pro Arg Gly Tyr
1               5                   10                  15

Ala Phe Ile Glu Tyr
            20

<210> SEQ ID NO 5
<211> LENGTH: 20
<212> TYPE: PRT
<213> ORGANISM: Artificial sequence
<220> FEATURE:
<223> OTHER INFORMATION: derived from U1 snRNP 70 kDa
<220> FEATURE:
<221> NAME/KEY: MOD_RES
<222> LOCATION: (3)..(3)
<223> OTHER INFORMATION: OXIDATION
<220> FEATURE:
<221> NAME/KEY: MOD_RES
<222> LOCATION: (9)..(9)
<223> OTHER INFORMATION: PHOSPHORYLATION

<400> SEQUENCE: 5

Ile His Met Val Tyr Ser Lys Arg Ser Gly Lys Pro Arg Gly Tyr Ala
1               5                   10                  15

Phe Ile Glu Tyr
            20

<210> SEQ ID NO 6
<211> LENGTH: 66
<212> TYPE: DNA
<213> ORGANISM: Artificial Sequence
<220> FEATURE:
<223> OTHER INFORMATION: derived from U1 snRNP 70 kDa
```

```
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 6
mgnathcaya tggtntayws naarmgnwsn ggnaarccnm gnggntaygc nttyathgar    60 taytrr                                                              66
```

METHODS OF TREATING CHRONIC INFLAMMATORY DISEASES

CROSS-REFERENCE TO RELATED APPLICATIONS

This application claims the benefit of U.S. Provisional Patent Application 62/091,379, filed: Dec. 12, 2014, titled: Modified Peptides and Their Use for Treating Autophagy-Related Diseases, which is incorporated herein by reference.

INCORPORATION BY REFERENCE

An electronic version of the Sequence Listing file name: P140_seq_listing_ST15.txt, size: 6.5 KB containing SEQ ID NOs: 1-6 is filed herewith, and is hereby incorporated by reference in its entirety.

BACKGROUND

1. Field of the Discovery

The present invention relates to modified peptides, and their use for treating immune diseases, including autoimmune diseases and autophagy-related autoimmune disorders.

2. Background Information

In autoimmunity, the patient's immune system is activated against the body's own components. Autoimmune diseases are not considered orphan diseases. In general they are even not regarded as rare since as a whole they affect millions people worldwide. As a result of genetic influence, which is mostly polygenic, or environmental and metabolic factors, there is some disequilibrium regarding their incidence or severity in some parts of the world and in particular groups of people. According to the American Autoimmune Related Diseases Association, autoimmune diseases affect up to 50 million Americans. There is a sexual dimorphism among autoimmune diseases with a well-established disequilibrium toward the female population. The overall cumulative prevalence of all autoimmune diseases is around 5%, with about 3% for males and 7% for females (Hayter and Cook, 2012). This female bias occurs in 59% of autoimmune diseases, probably in relation with hormonal influence and X-chromosome encoded genes. In general the onset for autoimmune diseases occurs in young people (20-29 year age-group). It has been estimated that autoimmune diseases are among the top ten leading causes of death among women in all age groups up to 65 years.

Under the term autoimmune diseases, there are more than eighty illnesses caused by autoimmunity, including, e.g. Crohn's disease/CD; primary biliary cirrhosis, myasthenia gravis, immune thrombocytopenic purpura, rheumatoid arthritis, neuropsychiatric lupus, ocular myasthenia gravis, psoriatic arthritis. Also some individuals may have more than one autoimmune disorder at the same time, which complicates the task of follow-up and treatment, and makes each case unique. However, there is no known prevention for most autoimmune disorders, and in general there is no specific treatment.

A large number of autoimmune diseases are recognized. They are characterized as "organ-specific" when they are restricted to certain organs such as thyroid (e.g. Graves' disease, autoimmune thyroiditis, Hashimoto's disease), pancreas (e.g. type 1 diabetes in which insulin-producing beta cells are destroyed) and muscles (myasthenia gravis) or involve a particular tissue in different places (e.g. Goodpasture's disease, which affects the basement membrane in the lung and kidney). In contrast, they are classified as "systemic" when they implicate a variety of organs and tissues in the whole body. The most emblematic representative of the large family of systemic autoimmune diseases is systemic lupus erythematosus (SLE) in which heart, joints, skin, lungs, blood vessels, liver, kidneys, and nervous system can be affected. In fact, between these two commonly described families, there is no sharp delineation. For example, scleroderma, also known as systemic sclerosis, which is a chronic systemic autoimmune disease characterized by hardening of the skin, also affects blood vessels, muscles, and internal organs in severe forms.

Deciphering the molecular and cellular mechanisms leading to immune tolerance breaking and evolution toward autoimmune disease remains a vast area of investigations in the scientific and clinical community. Nowadays, no universal signature could be identified, and clues are largely lacking regarding the reasons of their tropism as well as on the elements triggering their initiation and maintenance. Relatively little is also known regarding the events governing the successive periods of flares and remission occurring in certain autoimmune diseases such as SLE.

The multifactorial and polymorphic nature of most autoimmune diseases dramatically complicates their diagnosis and the treatment that can be applied to mitigate the symptoms. Except in very rare cases, the treatments are largely palliative and do not target the cause of illness. Although immense progress has been made over the last decades leading to patients' survival rates that have considerably augmented, innovative therapeutic solutions are still awaiting that would combine efficacy, selectivity- and thus less secondary effects- and reliability. Without adapted treatment, the quality-of-life can be relatively poor in autoimmune patients and decreases as the disease evolves (fatigue, pain, fever associated to specific symptoms). Unfortunately, the medications required to minimize symptoms and slow-down inflammatory syndrome (i.e. corticosteroids, immunosuppressive drugs and tumor necrosis factor (TNF-α) blockers used for long-term periods) induce an alteration of the whole immune system leading to intestinal bleeding, kidney failure, increased blood pressure, insomnia, depression, psychosis, osteoporosis, muscle loss, and diabetes, not to mention overwhelming repetitive infection episodes and cancer development. In certain autoimmune diseases such as those affecting the central nervous system, or in anti-phospholipid syndrome that can be associated to SLE, the therapeutic solutions are limited, not specific, and unfortunately sometimes inefficient (Carrithers, 2014; Hanly, 2014; Inglese and Petracca, 2014; Jeltsch-David and Muller, 2014). Intense research is currently ongoing to develop novel immunomodulatory strategies based on molecular targets that are engaged in deregulated autoimmune processes and can be specifically re-orientated. In this context, a better knowledge of cellular and molecular mechanisms that underline autoimmune responses and most particularly the homeostasis and regulation of autoimmune cells is central.

Autophagy is a normal physiological process that plays a pivotal role for cell survival, differentiation, development, and homeostasis. Selective or not, canonical or non-canonical, autophagy processes are considerably more complex than originally thought. Depending on favourable or unfavourable cell environment conditions, the autophagy machinery will promote both cell survival and cell death, thus maintaining a decisive balance between manufacture of cellular components and breakdown of damaged or superfluous organelles and other cellular constituents, for example. Autophagy displays complex, still-debated, interwoven links with several other degradative pathways, such as apoptosis and proteasome-mediated systems. Among its many cellular regulatory functions that have been experimentally proven or that are anticipated, autophagy decisively controls immunity and inflammation, and any impaired autophagy signalling can potentially lead to autoimmune-related diseases.

Thus, there exists in the art an ongoing need for therapeutic interventions to treat and prevent autoimmune diseases. In particular, there exists a need for therapeutic interventions that target key cellular processes involved in the initiation and persistence of autoimmune diseases, e.g., the autophagic process, which is involved in the establishment and maintenance of immune tolerance and the proper effectiveness of the immune system, which has particular importance in autoimmunity. Accordingly, there is a need to provide therapeutic interventions capable of advantageously modulating the autophagic processes as a means for treating, preventing and/or ameliorating the symptoms of autoimmune disorders.

SUMMARY

The present description provides therapeutic compositions and methods of using the same that are based on the surprising and unexpected discovery that chemically modified peptides as described herein are potent modulators of autophagy, in particular excessive or increased chaperone-mediated autophagy (CMA). The chemically modified peptides as described herein are derived from the U1-70K spliceosomal protein. The described peptides and compositions comprising effective amounts of the same are effective for treating, preventing and/or ameliorating the symptoms of diseases characterized by an increased autophagy flux; i.e., hyper autophagy-related autoimmune disorders such as hyper-CMA related disorders. Accordingly, in certain additional aspects, the disclosure provides methods of making and using the described peptides and compositions comprising the same for the treatment, prevention and/or amelioration of the symptoms of diseases characterized by an increased autophagy flux, e.g., CMA. Without being bound by any particular theory, it is hypothesized that the described compositions reduce autophagy flux by blocking certain activities of the lysosome.

Thus, in one aspect the present description provides chemically modified peptides of SEQ ID NOs: 1, 2, 4 and 5, including derivatives, analogs and salt forms thereof.

In certain embodiment, the description provides an isolated peptide comprising or consisting of the amino acid sequence of SEQ ID NO: 1: RIHMVYSKRSGKPRG-YAFIEY [SEQ ID NO: 1], or

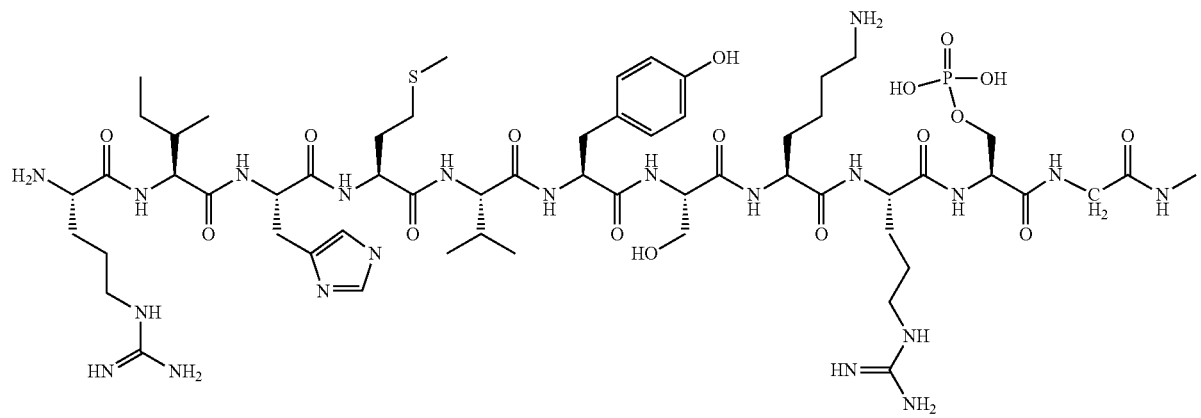

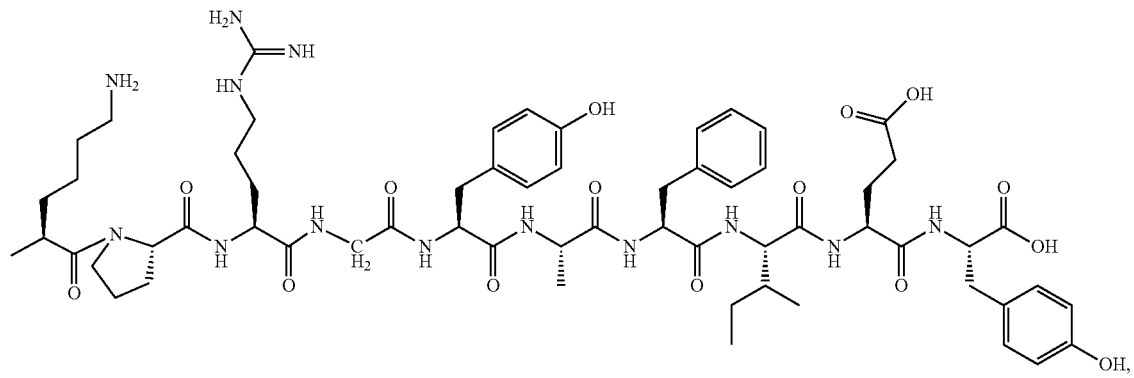

or salt thereof, having at least one post-translational modification selected from the group consisting of phosphorylation of a serine residue, oxidation of a methionine residue, and acetylation of a lysine residue, and combinations thereof. In an embodiment of this aspect, the description provides a composition comprising an isolated and/or chemically modified peptide (recombinant or synthesized) having or consisting of the amino acid sequence of SEQ ID NO: 1, or salt thereof, wherein the peptide comprises a phosphoserine at position 10 (i.e., "P140 peptides"). In certain embodiments, the description provides an isolated and/or chemically modified peptide (recombinant or synthesized) having or consisting of the amino acid sequence of SEQ ID NO: 1, or salt thereof, wherein the peptide comprises a phosphoserine at position 10, and an oxidized Methionine residue at position 4.

In certain additional embodiments, the peptide of SEQ ID NO:1 also comprises an acetylated lysine residue. In particular, said peptide of SEQ ID NO: 1 comprises a phosphoserine at position 10, and an oxidized Methionine residue at position 4, and an acetylation of one or both of the lysine at position 8 and 12, and more particularly further comprises a phosphoserine at position 7.

In certain embodiments, the description provides an isolated and/or chemically modified peptide (recombinant or synthesized), or a salt thereof, comprising or consisting of the amino acid sequence: IHMVYSKRSGKPRGYAFIEY [SEQ ID NO: 2], in which the Serine (S) at position 9 is phosphorylated, and the Methionine (M) at position 3 is oxidized.

In certain embodiments, the description provides a peptide of compound I having the following formula:

Compound I can also be represented by:

$$\text{IHM(O)VYSKRS(PO}_3\text{H}_2\text{)GKPRGYAFIEY} \quad \text{[SEQ ID NO: 5]}$$

in which "M(O)" represents oxidized methionine, and "S(PO$_3$H$_2$)" represents phosphoserine.

These peptides are derived from the human U1 snRNP 70 kDa protein (SEQ ID NO: 3), and correspond to the region delimited by the amino acid segment extending from the residue 132 to the residue 151 of SEQ ID NO: 3. Formally, the residue which is phosphorylated corresponds to the amino acid at the position 140 from the first methionine of SEQ ID NO: 3, and the residue which is oxidized corresponds to the amino acid at the position 134 from the first methionine of SEQ ID NO: 3.

In additional aspects, the description provides an isolated and/or chemically modified peptide (recombinant or synthesized) comprising or consisting of the amino acid sequence of SEQ ID NO: 2, or salt thereof, having at least one post-translational modification selected from the group consisting of phosphorylation of a serine residue, oxidation of a methionine residue, and acetylation of a lysine residue, and combinations thereof. In an embodiment of this aspect, the description provides a composition comprising an isolated and/or chemically modified peptide (recombinant or synthesized) having or consisting of the amino acid sequence of SEQ ID NO: 2, or salt thereof, wherein the peptide comprises a phosphoserine at position 9, and an oxidized Methionine residue at position 3. In certain additional embodiments, the peptide of SEQ ID NO:2 also comprises an acetylated lysine residue.

In certain embodiments, the description provides a peptide of compound II having the following formula:

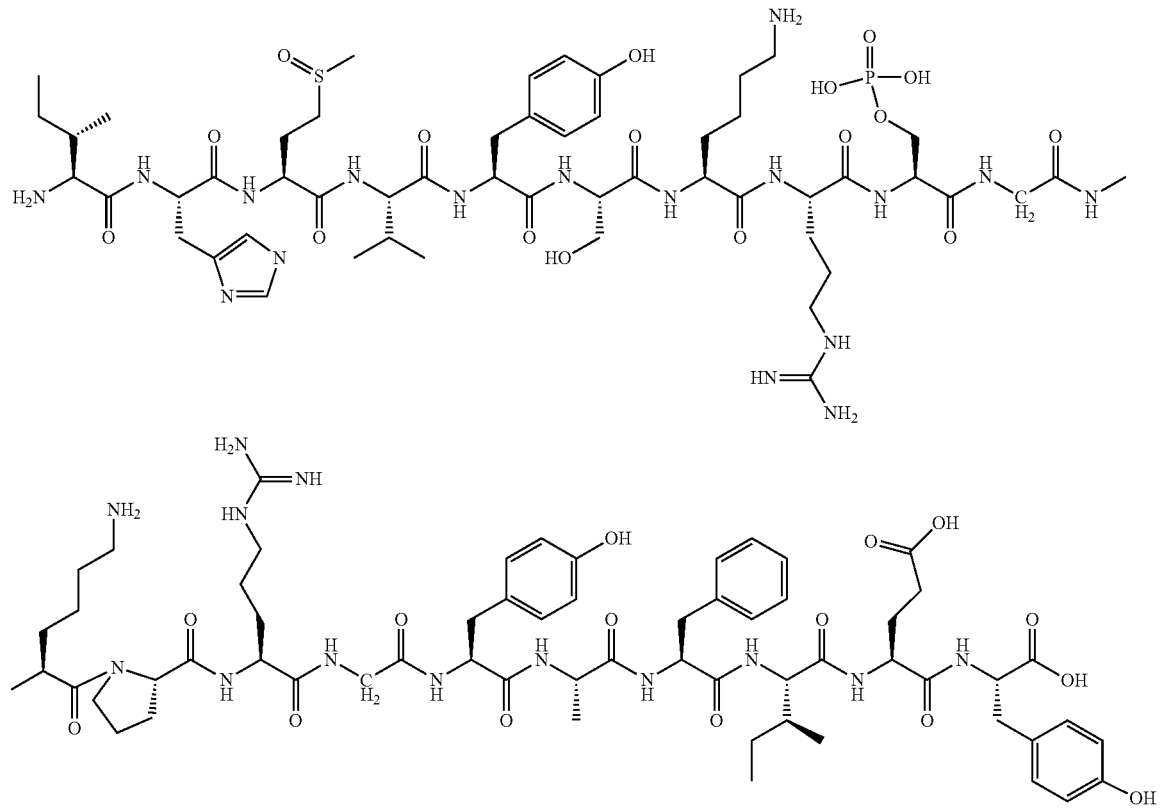

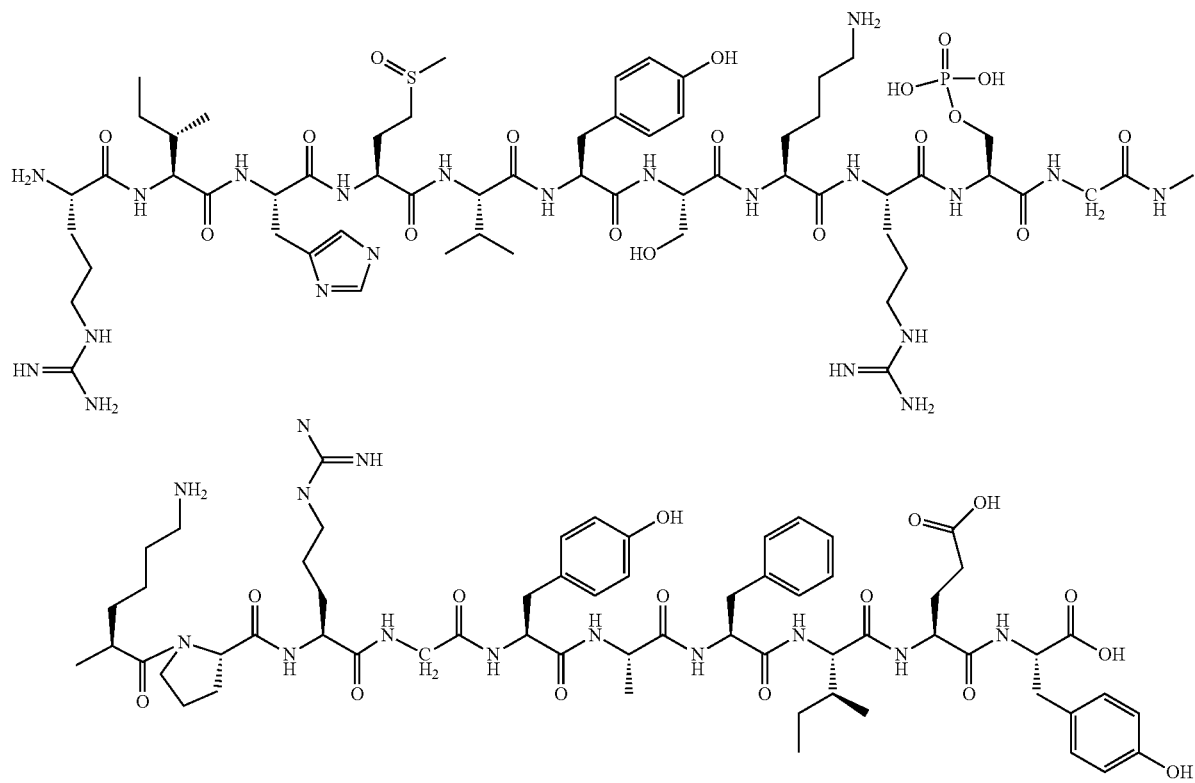

Compound II can also be represented by:

[SEQ ID NO: 4]
RIHM(O)VYSKRS(PO₃H₂)GKPRGYAFIEY in which M(O) represents oxidation of methionine, and S(PO₃H₂) represents the phosphorylation of serine.

Thus, the description provides peptides, or a salt thereof, comprising or consisting of the amino acid sequence chosen among the group consisting of SEQ ID NO: 4 and SEQ ID NO: 5.

In an additional embodiment, the description provides a composition comprising an effective amount of at least one peptide, or salt thereof, selected from the group consisting of the amino acid sequence SEQ ID NO: 2, comprising a phosphoserine at position 9, and oxidized Methionine at position 3; the amino acid sequence SEQ ID NO: 1, comprising a phosphoserine at position 10, and an oxidized Methionine at position 4; the amino acid sequence of SEQ ID NO: 1, or salt thereof, wherein the peptide comprises a phosphoserine at position 10, and a combination thereof.

In another aspect the present description provides compositions comprising an effective amount of one or more of the peptides as described herein, and an excipient or carrier.

In an additional aspect, the present description provides methods for treating, preventing or ameliorating the symptoms of an autoimmune disease, e.g., an autophagy-related immune system disease or disorder, e.g., a hyper autophagy-related autoimmune disease or hyper-CMA related autoimmune disease, comprising administering an effective amount of a therapeutic composition as described herein to a subject in need thereof, wherein the composition is effective for treating, preventing and/or ameliorating at least one symptom of the disease or disorder.

In certain embodiments, the disease or disorder is selected from the group consisting of a disease or disorder related to excessive or increased autophagy, e.g., CMA. In certain embodiments the disease or disorder is a chronic inflammatory disorder such as rheumatoid arthritis (RA), multiple sclerosis (MS), myopathies, muscular dystrophy (MD), Crohn's disease (CD), Chronic obstructive pulmonary disease (COPD) fibromyalgia, polymyositis, pulmonary disease, chronic immune thrombocytopenia (ITP), neuropsychiatric lupus, Gougerot-Sjögren syndrome, rheumatoid arthritis, Guillain-Barré disease (chronic/CIDP), asthma (acute or chronic), eosinophilic airway inflammation, irritable bowel syndrome (IBS or IBD), chronic inflammatory demyelinating polyradiculoneuropathy (CIDP), type II diabetes, regeneration of fat tissue, scleroderma, psoriasis, Alzheimer's, or Parkinson's.

In certain additional aspects, the description provides therapeutic compositions comprising an effective amount of at least one peptide as described herein, and at least one additional bioactive agent, e.g., an immunomodulatory agent, e.g., an agent capable of inhibiting or reducing autophagy flux. In certain embodiments, the composition further comprises an excipient or carrier as described herein.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

DETAILED DESCRIPTION

Figure 1:
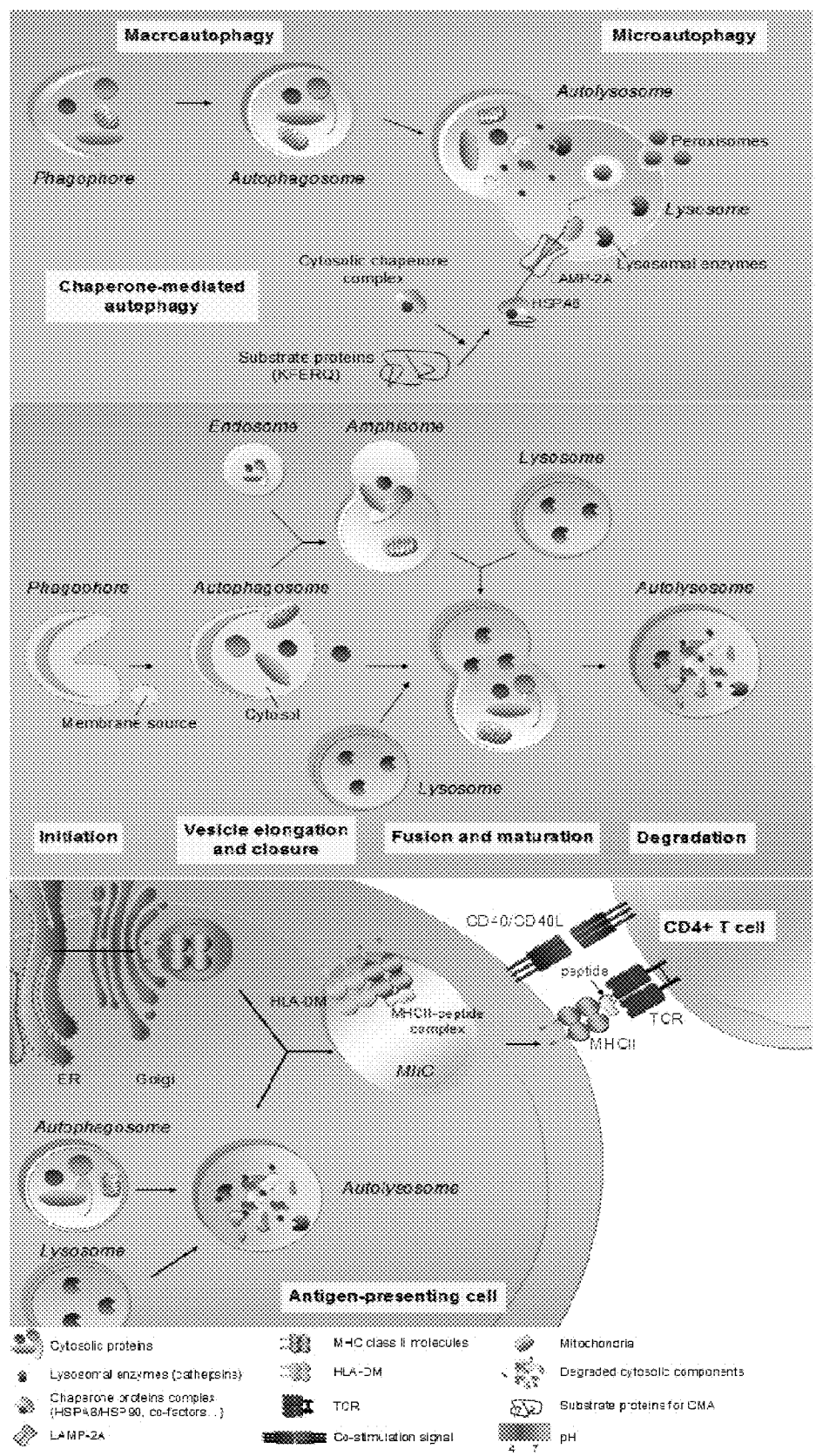
FIG. 1. Schematic depiction of autophagic pathways. (A) The three main autophagy axes, macroautophagy, microautophagy and CMA. The process of macroautophagy is initiated with the formation the so-called isolation membrane. The latter is elongated to engulf cytosolic materials, forming a characteristic double-membrane structure termed autophagosome. The latter next fuses with a lysosome to become an autolysosome, after which the engulfed material is degraded. The molecular pathways regulating autophagy are highly conserved from yeast to higher eukaryotic cells. In CMA, proteins carrying the pentapeptide KFERQ-like signal sequence are recognized by the HSPA8 chaperone, which then associates to LAMP-2A, triggering its oligomerization. This event permits to the targeted protein to be translocated into the lysosome lumen through a process that requires HSPA8. Microautophagy involves the direct sequestration of cellular components by the lysosome through invagination of the lysosomal membranes; (B) Main steps of the macroautophagic process; (C) Autophagy as the major sources of peptides for presentation by MHCII molecules to T cells. Abbreviations: CMA, chaperone-mediated autophagy; ER, endoplasmic reticulum; HLA, human leukocytes antigen; HSPA8/HSC70, heat shock cognate protein of 70 KDa; LAMP-2A, lysosome-associated membrane protein-2A; MIIC, major histocompatibility complex class II compartment; MHCII, major histocompatibility complex class II; TCR, T cell receptor.

The following is a detailed description of the invention provided to aid those skilled in the art in practicing the present invention. Those of ordinary skill in the art may make modifications and variations in the embodiments described herein without departing from the spirit or scope of the present invention. Although any methods and materials similar or equivalent to those described herein can also be used in the practice or testing of the present invention, the preferred methods and materials are now described. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

As used herein, the following terms may have meanings ascribed to them below, unless specified otherwise. However, it should be understood that other meanings that are known or understood by those having ordinary skill in the art to which the invention belongs are also possible, and within the scope of the present invention.

It must be noted that as used herein and in the appended claims, the singular forms "a", "and", and "the" include plural references (i.e., refer to one or to more than one or at least one) to the grammatical object of the article. By way of example, "an element" means one element or more than one element.

The term "about" as it is used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. In accordance with the above, the phrase "about" is normally used to encompass values within the standard deviation or standard error.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "derivatives" can mean, but is in no way limited to, chemical compositions, for example, nucleic acids, nucleotides, polypeptides or amino acids, formed from the native compounds either directly, by modification, or by partial substitution. The term "analogs" can mean, but is in no way limited to, chemical compositions, for example, nucleic acids, nucleotides, polypeptides or amino acids that have a structure similar to, but not identical to, the native compound.

The term "effective amount/dose," "pharmaceutically effective amount/dose," "pharmaceutically effective amount/dose" or "therapeutically effective amount/dose" can mean, but is in no way limited to, that amount/dose of the active pharmaceutical ingredient sufficient to prevent, inhibit the occurrence, ameliorate, delay or treat (alleviate a symptom to some extent, preferably all) the symptoms of a condition, disorder or disease state. The effective amount depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the agent. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The term "pharmacological composition," "therapeutic composition," "therapeutic formulation" or "pharmaceutically acceptable formulation" can mean, but is in no way limited to, a composition or formulation that allows for the effective distribution of an agent provided by the invention, which is in a form suitable for administration to the physical location most suitable for their desired activity, e.g., systemic administration.

The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

The term "local administration" refers to a route of administration in which the agent is delivered to a site that is apposite or proximal, e.g., within about 10 cm, to the site of the lesion or disease.

The term "conservative mutations" refers to the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

By "homology" is meant the nucleotide sequence of two or more nucleic acid molecules or two or more nucleic acid or amino acid sequences is partially or completely identical. In certain embodiments the homologous nucleic acid or amino acid sequence has 30%, 40%, 50%, 60%, 70%, 80%, 90%, or 95% sequence similarity or identity to an nucleic acid encoding the amino acid sequence of SEQ ID NO:1 or SEQ ID NO:1, respectively.

"Homologs" can be naturally occurring, or created by artificial synthesis of one or more nucleic acids having related sequences, or by modification of one or more nucleic acid to produce related nucleic acids. Nucleic acids are homologous when they are derived, naturally or artificially, from a common ancestor sequence (e.g., orthologs or paralogs). If the homology between two nucleic acids is not expressly described, homology can be inferred by a nucleic acid comparison between two or more sequences. If the sequences demonstrate some degree of sequence similarity, for example, greater than about 30% at the primary amino acid structure level, it is concluded that they share a common ancestor. For purposes of the present invention, genes are homologous if the nucleic acid sequences are sufficiently similar to allow recombination and/or hybridization under low stringency conditions. In addition, polypeptides are regarded as homologous if their nucleic acid sequences are sufficiently similar to allow recombination or hybridization under low stringency conditions, and optionally they demonstrate membrane repair activity, and optionally they can be recognized by (i.e., cross-react with) an antibody specific for an epitope contained within the amino acid sequence of at least one of SEQ ID NOs: 1-6.

The term "cell" can mean, but is in no way limited to, its usual biological sense, and does not refer to an entire multicellular organism. The cell can, for example, be in vivo, in vitro or ex vivo, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The term "host cell" can mean, but is in no way limited to, a cell that might be used to carry a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce one or more of the polypeptide components of the complex of the invention.

The term "patient" or "subject" is used throughout the specification to describe an animal, preferably a human or a domesticated animal, to whom treatment, including prophylactic treatment, with the compositions according to the present invention is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present invention, the term patient refers to a human patient unless otherwise stated or implied from the context of the use of the term.

As used herein, "P140 peptides" can mean but is not limited to phosphorylated peptides derived from the spliceosome U1-70K protein, including those exemplified in SEQ ID NOs.: 1, 2, 4, and 5. In certain instances P140 is used to specifically refer to a peptide consisting of the amino acid sequence SEQ ID NO: 1, in which serine at position 10 is phosphorylated.

The term "therapeutically effective amount or dose" includes a dose of a drug that is capable of achieving a therapeutic effect in a subject in need thereof. For example, a therapeutically effective amount of a drug can be the amount that is capable of preventing or relieving one or more symptoms associated with a disease or disorder, e.g., tissue injury or muscle-related disease or disorder. The exact amount can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

A kit is any manufacture (e.g. a package or container) comprising at least one reagent, e.g. a probe, for specifically detecting a marker of the invention. The manufacture may be promoted, distributed, or sold as a unit for performing the methods of the present invention. The reagents included in such a kit comprise probes/primers and/or antibodies for use in detecting sensitivity and resistance gene expression. In addition, the kits of the present invention may preferably contain instructions which describe a suitable detection assay. Such kits can be conveniently used, e.g., in clinical settings, to diagnose patients exhibiting symptoms of cancer, in particular patients exhibiting the possible presence of a tumor.

All publications, patent applications, patents, and other references mentioned herein are incorporated by reference in their entirety. In the case of conflict, the present specification, including definitions, will control. In addition, the materials, methods, and examples are illustrative only and not intended to be limiting.

The following references, the entire disclosures of which are incorporated herein by reference, provide one of skill with a general definition of many of the terms used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991).

The present description provides therapeutic compositions and methods of using the same that are based on the surprising and unexpected discovery that chemically modified peptides as described herein are potent modulators of autophagy. In particular, the peptides and compositions described herein are surprisingly effective for reducing excess or hyper autophagy, including chaperone-mediated autophagy (CMA). As such, the description provides compositions and methods for treating hyper-autophagy, e.g., hyper-CMA, related diseases and disorders.

Autophagy is a lysosome-based physiological process, which in basal conditions occurs at low levels to continuously degrade unwanted cytoplasmic constituents and generate substrates for energy production. During oxidative stress, hypoxia or nutritional starvation, its level raises to allow cell survival. Autophagy represents therefore a major hub involved in cellular homeostasis (Awan and Deng, 2014; He and Klionsky, 2009; Mizushima, 2007; Okamoto, 2014; Ravikumar et al., 2010). It also plays a pivotal role in differentiation of many lineages, including adipocytes, erythrocytes and lymphocytes, and tissue remodelling (Cenci, 2014; Lee et al., 2014; Mizushima and Komatsu, 2011; Mizushima and Levine, 2010; Nedjic et al., 2008; Pampliega et al., 2013). Under specific environmental conditions, however, autophagy can also mediate cell death and it is mechanistically important to distinguish autophagic cell death, which refers to cell death "by" autophagy from cell death "with" autophagy (Kroemer and Levine, 2008; Marino et al., 2014; Ryter at al., 2014; Shen et al., 2012). Thus, recent studies suggest that autophagy and apoptosis processes are closely nested and share cross-talk between signal transduction elements. It has been shown in particular that certain autophagy-related (ATG) proteins play dual roles in autophagy and apoptosis regulation. This is the case of ATG5 and its binding partner ATG12, BCL-2 interacting myosin/moesin-like coiled-coil protein 1 (BECLIN1/beclin-1), the mammalian ortholog of yeast Atg6/vacuolar protein sorting (Vps)-30 that acts during the formation of autophagosomes by interacting with the class III PI3K pathway, and microtubule-associated-protein light chain 3 (MAP1LC3/LC3) a mammalian ortholog of yeast Atg8, for example (Kang et al., 2011; Konishi et al., 2012; Li et al., 2012; Marquez et al., 2012). Other forms of cell death are also interconnected with autophagy, such as necrosis, necroptosis (regulated Fas-dependent, caspase-independent non-apoptotic cell death), and pyroptosis (caspase-1-dependent cell death) (Ryter et al., 2014).

Three main types of autophagy have been identified and can be distinguished by both their physiological functions and the mechanisms they use to deliver cytoplasmic cargo to lysosomes (FIG. 1A). They are macroautophagy, microautophagy and chaperone-mediated autophagy or CMA (Cuervo, 2004; Feng et al., 2014, Kaushik and Cuervo, 2012; Okamoto, 2014). In fact, many more forms of autophagy have been described. Mention can be made, for example, of aggrephagy (for aggregated proteins), mitophagy (for mitochondria), ribophagy (for ribosomes), pexophagy (for peroxisomes), reticulophagy (for the endoplasmic reticulum, ER), and xenophagy (for pathogens). Thus, we now realize that while originally viewed as a nonselective (random) cytoplasmic degradation system, autophagy actually participates in a highly selective and tightly regulated process of substrate delivery.

Macroautophagy (commonly referred as "autophagy", which can in some cases create confusion in the literature) remains the major autophagic process through its ability to massively entrap macromolecules and entire organelles. The latter are captured into double-membrane autophagosomes where they are degraded. It therefore represents an alternative mechanism of proteasomal degradation, which rather treats short-lived intracellular proteins, although a cross-talk that is being increasingly understood, has been described to occur between the ubiquitin-proteasome system (UPS) and macroautophagy (Cuervo and Wong, 2014; Kirkin et al. 2009; Korolchuck et al., 2010; Lilienbaum et al., 2013; Ravikumar et al., 2010). The fusion of autophagosomes with lysosomes leads to the formation of autolysosomes in which engulfed cellular constituents—including lipid droplets and protein aggregates—are degraded by lysosomal glycosidases, proteases, lipases and sulfatases (FIG. 1B). Concerning the CMA process, proteins containing a specific peptide motif biochemically related to KFERQ are recognized by the HSPA8/HSC70 chaperone protein prior being internalized and degraded in lysosomes (FIG. 1A). By contrast, in microautophagy, cytosolic components are directly taken up by invaginations of the lysosomal membrane (FIG. 1A).

Autophagic pathways are genetically regulated by proteins belonging to the ATG gene family and are well characterized in yeast and mammals (Codogno et al., 2012; Klionsky and Emr, 2000; Lamb et al., 2013; Mizushima et al., 2011; Oshumi, 2014; Shibutani and Yoshimori, 2014). ATG proteins are evolutionary conserved and each of them has a specific function during autophagy. It is mainly through the discovery that certain ATG genes could be associated to autoimmune syndromes that further studies have been generated to understand the links existing between autophagy and autoimmunity. Genetic analyses effectively reported that some polymorphisms in ATG genes might confer susceptibility to different autoimmune disorders. Thus genome-wide association studies (GWAS) performed in SLE patients identified several single nucleotide polymorphisms (SNPs) located on ATG genes, which have been associated with the disease occurrence (Harley et al., 2008; Orozco et al., 2011). One SNP located in the intergenic region between ATG5 and PRDM1 was found to correlate with a greater expression of ATG5 mRNA (Zhou et al., 2011). The genetic association between ATG5 and susceptibility to SLE has been confirmed in individual studies, but not found in others (Järvinen et al., 2012). Interestingly, a recent meta-analysis in Asians showed strong association of SNPs on DRAM1 with SLE susceptibility (Yang et al., 2013). This gene encodes an activator of macroautophagy in response to p53-mediated stress signals. In patients with CD, a GWA study identified rs2241880, mapping to the ATG16L1 locus, as a susceptibility variant (Hampe et al., 2007). A statistically significant interaction with respect to CD risk between rs2241880 and the established CARD15/NOD2 (nucleotide-binding oligomerization domain containing 2) susceptibility variants was shown. Interestingly there was no association between rs2241880 and ulcerative colitis, another closely related inflammatory bowel disease. Recent data showed that Atg16L1 mutant mice are resistant to intestinal disease induced by the model bacterial pathogen *Citrobacter rodentium* (Marchiando et al., 2013). The hyperimmune phenotype and protective effects developed in these mice were lost in Atg16L1/Nod2 double-mutant mice, indicating that the susceptibility from Nod2-deficiency is dominant over the benefit of Atg16L1 deficiency. ATG16L1 is central in the autophagosome formation, being part of the ATG12-ATG5 complex, which is required for the recruitment of MAP1LC3 (Mizushima et al., 2011). Removal of ATG16L1 abrogates the ability of cells to form autophagosomes (Saitoh et al., 2008). More recently it was described that the variant protein that contains an Ala→Thr substitution at position 300 is highly sensitive to cleavage by caspase 3, which is activated during cell stress (Murthy et al., 2014). Destruction of ATG16L1T300A impaired autophagy and increased release of pro-inflammatory cytokines TNF-☐ and IL-1☐. Several SNPs have been described in association with CD, notably in the so called immunity-related GTPase family M (IRGM) gene (Glas et al., 2013; Lu et al., 2013). The results indicated that autophagy gene-IRGM polymorphisms confer susceptibility to CD but not ulcerative colitis, especially in Europeans. IRGM is a member of the interferon-inductible GTPase family conferring autophagic defence against intracellular pathogens like *M. Tuberculosis*. IRGM controls the latter by enhancing mycobacterial phagosome maturation (Singh et al., 2006).

Altogether these data argue for a strong impact of autophagy elements in several aspects of immunity, including protection to infectious agents and control of inflammatory and autoimmune responses, as well as in tumorigenesis and cancer. Paradoxically, it is only recently that experimental studies based on cellular and molecular investigation shed some light on the involvement of autophagy in immunity. A number of comprehensive review articles have been recently published on this topic with a particular emphasis on the role of autophagy in infection and inflammation (Cenci, 2014; Deretic, 2012; Deretic et al., 2013; Gros and Muller, 2014; Levine et al., 2011; Oliva and Cenci; 2014; Puleston and Simon, 2013; Ravikumar et al., 2010). The present review mainly focuses on autophagy in autoimmunity, in relation with possible manipulation of immune system by small molecules and peptides in order to divert deleterious immune responses and at least partly restore impaired tolerance to self.

Innate immune responses importantly influence the adaptive immunity in the induction and regulation of autoimmune diseases. In innate immunity, autophagy works at different levels, notably by controlling activation and release of certain cytokines and chemokines (Deretic 2012; Deretic et al., 2013; Gros and Muller, 2014; Jones et al., 2013; Saitoh and Akira, 2010). Autophagy would activate the secretion of TNFα, interleukin (IL)-6, IL-8 and type I interferon (IFN) while it controls the production of IL-1α and β (the latter by regulating inflammasome activation and by targeting pro-IL-1β for degradation), IL-18 and type I IFN. In turn, some secreted cytokines influence autophagy. Thus, T helper type 1 (Th1) and pro-inflammatory cytokines such as IFN-γ (via IRGM), TNFα, IL-1α, and β, IL-23, reactive oxygen species (ROS) and engagement of some TLRs (mechanisms that are still poorly understood) induce autophagy. TWEAK (the TNF-like weak inducer of apoptosis, in C2C12 myotubes), IL-2 in CD4+ T cells, IL-6 in peripheral blood mononuclear cells (PBMCs) and TGF-β in hepatocarcinoma cell lines also promote autophagy. Conversely, Th2 and regulatory cytokines such as IL-4, IL-13 and IL-10, via an effect on STAT-3 or -6 pathways and the serine/threonine-protein kinase (AKT) pathway were found to activate mammalian target of rapamycin (mTOR), which inhibits the serine/threonine protein kinase ULK1 and therefore autophagosome formation (Gutierrez et al., 2004; Jones et al., 2013). Via its effect on cytokine secretion, particularly in antigen-presenting cells (APCs), autophagy represents a pivotal regulator of immune responses (Cenci, 2014; Deretic et al., 2013; Gros and Muller, 2014; Levine et al., 2011; Nedjic et al., 2008; Ravikumar et al., 2010, Saitoh and Akira, 2010).

Although not yet recognized to such a level of crucial importance in current text books, autophagy in fact exerts profound effects on different aspects of adaptive immunity. It is a major player in thymic selection of T cells, affecting also T cell homeostasis, repertoire and polarization, survival of B cells, immune tolerance, and antigen presentation.

The discovery that autophagy is a key regulatory element for delivering self-antigens to major histocompatibility complex II (MHCII) molecules has been a critical turning point (Dengjel et al., 2005; Paludan et al., 2005; Zhou et al., 2005). At the time of this finding, it was established classically that MHC I molecules presented peptides from intracellular source proteins to T cells while MHCII molecules presented antigenic peptides from exogenous and membrane proteins. The overall picture of T cell activation by MHCII peptide was thus considerably reconsidered and new nexus between immune response and cellular stress, cell metabolism, cell nutrient and cell environment were suggested and analysed further. Incidentally, it is interesting to note that following experiments in which potent macroautophagy inhibitors acting on PI 3-kinase activity, i.e. wortmannin, LY294002 and 3-methyladenine (3-MA) were incubated with macrophage cell line BMC-2 transfected with E☐52-68-eGFP (a peptide fragment issued from transmembrane protein I-E☐) and shown to have no effect, it was concluded that macroautophagy was not a mechanism for cytoplasmic expressed proteins to gain access to the luminal peptide biding site of MHCII molecules (Dani et al., 2004). At that time conflicting data were published, which could result from the inherent properties of the antigen that was studied, its half-life and intracellular (vesicular or not) trafficking, and the type of APCs (Dörfel et al., 2005; Leung et al., 2010; Paludan et al., 2005).

More recent data have shown that in APCs that are less proteolytically active than other cells such as macrophages, cleavage by lysosomal cysteine proteases—generally known as cathepsins—of particles and proteins that finally reach autolysosomes give rise to protein fragments, which will constitute the major source of peptides for MHCII molecules (FIG. 1C). Lysosomes and autolysosomes have a pH of 4-4.5, which is optimum for cathepsins. Thus, and of importance in the context of autoimmunity, MHCII molecules can bind peptides generated from endogenous antigens that are generated by lysosomal proteolysis. Such endogeneous antigens can be from membranous, cytoplasmic (including vesicle components) or nuclear origin and can have trafficked into the endo-lysosomal network via several forms of autophagy for subsequent processing and presentation by MHCII molecules to promote CD4+ T cells priming (Blum et al., 2013; Münz, 2012). Interestingly, in their pioneer work, Stevanovic, Rammensee and coll. already demonstrated that the induction of autophagy by starvation altered the balance of active proteases in lysosomes (Dengjel et al., 2005), which as a matter of consequence, can change the quality of peptides that are loaded onto MHCII molecules.

Over the last decade, the role and regulation of specific proteases on the liberation and processing of self-antigens has been studied extensively (van Kasteren and Overkleeft, 2014; Villadangos et al., 1999) and it was shown in particular that a distinct set of cathepsins is at work in different APCs, e.g. dendritic cells (DCs) and B cells (Burster et al., 2004; Manoury et al., 2002). There are also multiple mechanisms (including gene up-regulation or down-regulation governed by the environment), that are involved for controlling proteases activity, even in individual endosomes, and strongly affect antigen presentation (Dengjel et al., 2005; van Kasteren and Overkleeft, 2014). Endo-lysosomal proteases are thus key players to generate antigens that in fine will be presented to T cells. Via a stepwise process involving asparagine endopeptidase (AEP) also known as legumain, cystatin C, specific cathepsins and other still unspecified proteases, endo-lysosomal proteases act for processing the invariant (Ii) chain linked to MHCII molecule into class-II associated invariant chain peptide (CLIP), thus generating peptide-receptive MHCII molecules in which the CLIP peptide is exchanged for a high affinity peptide by the enzyme HLA-DM (FIG. 1C) prior its transport to the cell surface of APCs for display to CD4+ T cells (Neefjes et al., 2011). Endo-lysosomal proteases, including AEP, also act to generate epitopes that will be presented by functional MHCII molecules (Colbert et al., 2009; Matthews et al., 2010; van Kasteren and Overkleeft, 2014).

In the many examples of antigens that have been examined so far, stability was found to be a determining factor that influences antigen presentation. Furthermore because the cleavage via cathepsins can liberate epitopes but also destroy some others, cathepsins regulation is even more strategic for defining the final panel of antigenic peptides that are delivered. Finally, another important role of endo-lysosomal proteases in antigen-presentation lies to their influence on TLR-receptor signaling. Initially claimed while observing the effect of chloroquine (CQ) on TLR9 signaling (Hong et al., 2004; Matsumoto et al., 2008), it has been demonstrated later that endo-lysosomal proteases also activate endosomal TLRs 3, 7, and 8 (Manoury, 2013) and that the mode of action was not the one proposed in the first studies. In fact, whether for TLR9 or for endosomal TLRs, endo-lysosomal proteases would act by converting the receptor from a non-signaling full-length form to a shorter form deleted from an N-terminal region (Ewald et al., 2008; Park et al., 2008). Although the precise mechanisms that are behind this effect—notably considering the specific proteases that are involved—are still a continuing matter of debates, it remains that such an effect can be strategic as TLR-signaling is central for DC maturation that dictates protease activity and consequently influences the quality of peptides that are presented onto MHCII molecules. These data highlight the importance of TLRs in autophagy processes in conjunction with both innate (see above; Xu et al., 2007) and adaptive immunity.

The importance of autophagy in immunity also came from experiments performed with mice or cells that have been manipulated to under-express ATG genes. Using this strategy, associated to our growing knowledge of genes that appear defective in some individuals, it has been possible to better approach the potential role of some ATG proteins and establish some links with human diseases (Choi et al., 2013; Jiang and Mizushima, 2014; Majai et al., 2014). Thus, using mice with a B-cell-specific deletion of Atg5, a gene implicated in the elongation of autophagosome membrane, it has been shown that in autophagy-deficient B-cell progenitors the transition from the pro-B to the pre-B cell stage in the bone marrow was defective (Miller et al., 2008). Studies of mice in which Atg5 was conditionally deleted in B lymphocytes revealed further that this gene is essential for plasma cells (PC) homeostasis (Conway et al., 2013). Class-switch did occur in these mice but antibody responses were strongly decreased after specific immunisation, parasitic infection and mucosal inflammation. These data and others (Pengo et al., 2013) highlight the importance of ATG5 not only in early B cell development but also in late B cell activation and PC differentiation. Conditional deletion of essential autophagy genes Atg5 (Stephenson et al., 2009), Atg7 (Pua et al., 2009; Jia and He, 2011), Atg3 (Jia and He, 2011) also showed that macroautophagy is critical to the survival of peripheral T cells. Some Atg genes are important in infection setting.

Thus, using mouse embryonic fibroblasts (MEFs) lacking human ATG16L1 or murine Atg7, Atg9a, or Atg14, Oshima et al. (2014) showed the importance of ATG16L1, ATG7 and ATG16L1, but not of ATG9A and ATG14, in the IFN-γ-induced recruitment of the immunity-related GTPases to the intracellular pathogen $T.$ $gondii$. A number of examples in different forms of autophagy processes, including macroautophagy, CMA, and mitophagy have been described in which autophagy genes have been deleted or over-expressed, in some cases in specific tissues. Examples are Pink1/parkin knockout (KO) mice, the Atg16L1 mutant and Atg16L1/Nod2 double-mutant mice described above, Sqstm1/p62/A170 (encoding SQSTM1 multifunctional protein, also known as signaling adaptor/scaffold protein) mutant mice, conditional deletion models invalidating Beclin-1 or Vps34, to quote just a few. Some mutations affecting binding partners of key elements of autophagy pathways were also introduced. Thus, deletion of the gene encoding lysosome-associated membrane protein-2 (LAMP-2A) in T cells was shown recently to cause deficient in vivo responses to immunization or infection with $L.$ $monocytogenes$ (Valdor et al., 2014). In these mice, CMA in T cells was found to be altered with age. It should be mentioned here that mice invalidated for HSPA8 are not viable, as are Beclin-1 KO mice that die in utero or Atg5 KO mice that die within 24 h after birth due at least in part to deficient amino acid production.

The close relationships between autophagy and immunity reported above easily explain that any deregulation of autophagy machinery can affect various aspects of immune responses and lead to autoimmunity development (Gros and Muller, 2014; Lleo et al., 2007; Pierdominici et al., 2012). Enhanced autophagy, allowing survival of self-reactive lymphocytes, can promote autoimmunity. Moreover, autophagy, which produces autoantigens through intracellular protein digestion can participate in the initiation or maintenance of autoimmunity. In addition to SNPs and susceptibility genes, a number of studies have highlighted that expression of some genes related to autophagic process is modified during autoimmunity. In rheumatoid arthritis (RA), it has been shown that both ATG7 and BECLIN-1 gene expression is increased in osteoclasts from patients (Lin et al., 2013). Atg7 expression was found to be increased by pro-inflammatory cytokine TNF-α, a critical element for the pathogenesis through the regulation of synovial inflammation. Other studies have also demonstrated that in autoimmune demyelination syndrome and in multiple sclerosis (MS), ATG5 gene expression is also significantly elevated compared to healthy controls (Alirezaei et al., 2009).

Based on genetic evidences, potential links between autophagy and autoimmunity have been suggested for a decade. In general, however, experimental arguments at the cellular and molecular level showing a role of autophagy in the initiation and/or progression of autoimmune diseases are still scarce (Table 1). In SLE patients and two genetically unrelated mouse models of lupus, namely MRL/lpr and (NZB×NZW)F1 (NZB/W) mice, we showed in a seminal report that autophagy is deregulated in T lymphocytes (Gros et al., 2012). Autophagic vacuoles were found to be over-represented in T cells indicating that autophagy is hyperactivated. This deregulation was even more obvious when T cells were stimulated by chemical activators of T cell receptor (TCR)-related signaling pathways. The elevated autophagic compartment was not found in all T cells but was restricted to a subset of them. As autophagy is known to be involved in cell survival, these results suggest that autophagy could promote the survival of autoreactive T cells during the disease. Alessandri et al. (2012) showed an increase of the autophagosome-associated MAP1LC3-II isoform in T cells, which mainly occurred in naïve CD4 T cells isolated from SLE patients. These results, which confirm our own data, suggest that there is an intrinsic deregulation of autophagic activity in SLE T cells. The authors proposed another interpretation in concluding that SLE T cells are resistant to macroautophagy induction and could thus become more prone to apoptosis. They came to this conclusion by re-stimulating T cells with rapamycin or with autologous (pro-autophagic) serum. It is possible, however, that SLE T cells are already at the maximum level of autophagosome loading and that re-exposure to their own serum had no further effect on autophagic activity. In any case, these data confirm the pro-autophagic role of SLE serum on normal T cells. Pierdominici and her colleagues also observed that the increase of autophagy was correlated with disease activity scores, important information that could be exploited in future therapeutic strategies (Alessandri et al., 2012; Pierdominici et al., 2012; 2014).

More recent studies have reinforced and extended the pioneered works described above. Thus, for the first time, Clarke et al. (2014) showed in NZB/W mice that macroautophagy activation also occurs in B cells, and more particularly in early developmental and transitional stages of B cell development (before disease onset). In patients with lupus, autophagy was also activated compared to healthy individuals, and again this activation occurred mainly in naïve B cells. When autophagy inhibitors such as 3-MA, bafilomycin A1 or CQ were used, plasmablast differentiation and survival hardly occurred. These findings must be related to the overproduction of autoantibodies in the serum of lupus prone mice and patients with lupus. In their study, the authors confirmed that in addition to B cells, autophagy was increased in T cells from lupus patients, and that in both cases, this activation could be correlated to disease activity. Li et al. (2014) also described convincing results demonstrating that compared to controls, autophagy was significantly activated in the macrophages collected from an induced mouse model of lupus (BALB/c mice that develop a lupus-like disease after administration in Freund's adjuvant of homologous activated lymphocyte-derived DNA) and in the PBMCs of patients with lupus. Adoptive transfer of Beclin-1 KO macrophages significantly ameliorates the clinical conditions of recipient mice (decrease of proteinuria levels, reduction of typical renal complex deposition, amelioration of glomerulonephritis) as well as the biological features (decrease of serum anti-dsDNA antibody levels and circulating proinflammatory cytokines IL-6 and TNF-α as measured by ELISA).

A few studies have highlighted the role of autophagy in other autoimmune diseases, notably in human RA (Lin et al., 2013; Kato et al., 2014; Xu et al., 2013) and in experimental autoimmune encephalomyelitis, a model of MS (Bhattacharya et al., 2014). Autophagy appears to be activated in osteoclasts from patients with RA and regulates osteoclasts differentiation (Lin et al., 2013). This increased autophagic process, also found in RA synovial fibroblast compared to osteoarthritis synovial fibroblast by Kato et al. (2014) correlates with a reduced apoptosis level in RA synovial tissues (Xu et al., 2013). It was concluded from these observations that the activation of autophagy induced by overproduced TFN-α leads to the reduction of apoptosis in joints and more importantly causes the survival of synovial fibroblasts, which are responsible for the pathology. This again highlights the dual effect of autophagy, which is cytoprotective when it eliminates misfolded or too abundant cellular components, but in excess, can become deleterious and generate negative effects.

A number of recent findings underlined the pivotal role of macroautophagy in the control of muscle mass, and misregulation of autophagy has been described in myopathies and muscular dystrophies (Sandri et al., 2013). Information in relation to possible autophagy process dysfunction is scarce, however, regarding patients with fibromyalgia, for example, or with polymyositis (Temiz et al., 2009; Lloyd, 2010), a rare disease with an autoimmune component which is characterized by inflammation and degeneration of the muscles. On the other hand, autophagy defects have been observed (or suspected) in several autoimmune settings, including CD, SLE, possibly RA and MS (Table 1), as well as in inflammatory syndromes, notably in pulmonary diseases (Mizumura et al., 2012). It is strongly anticipated that in all these situations, modulation of autophagy, in order to re-establish a proper flux regulation in particular, might rescue alterations and improve the clinical status of treated patients.

As underlined recently (Gros and Muller, 2014), some molecules used for years to treat inflammatory and autoimmune diseases have been found much later to target one or another type of autophagy processes. Nowadays, in fact, there are very few specific compounds targeting precise steps of autophagy pathways, and even a single pathway in particular (Anguiano et al., 2013), and quite surprisingly, the targets of some autophagy regulators that are widely prescribed to patients are not really known. This is the case, in particular, of CQ and hydroxychloroquine (HCQ) or of dexamethasone, which mode of action (MOA) is still being debated (see below).

A number of comprehensive review articles have recently exhaustively covered various aspects, structural and functional, of families of compounds, activators and inhibitors, which have been generated to modulate autophagy directly or indirectly (Baek et al., 2012; Cheong et al., 2012; Fleming et al., 2011; Gros and Muller, 2014; Jiang and Mizushima, 2014; Renna et al., 2010; Rubinsztein et al., 2012; van Kasteren and Overkleeft, 2014; Vidal et al., 2014). Evaluated in rigorously calibrated assays performed both in vitro and in vivo (Mizushima et al., 2010; Klionsky et al., 2012), some of these small molecules might prove to be relevant to modulate autoimmune diseases in appropriate settings. In the examples shown in the next section we will limit ourselves to a few pharmacological regulators of autophagy with established or promising clinical efficacy in autoimmune diseases.

Pharmacological small molecules and peptides display a number of advantageous properties that makes them excellent therapeutics, notably for autoimmune diseases. In addition to their synthesis and production that can be highly optimized, and in some cases remarkably simple in comparison to some biologics, and automatable, small molecules and peptides selected as active components of pharmaceutical compositions are characterized by their stability and robustness, easy handling, the relatively low doses that have to be administered to patients and their cost, which remains reasonable with regard to most biologics. Small molecules and short peptides are not immunogenic per se, which is another considerable advantage for treating patients with chronic autoimmune diseases (Schall and Muller, 2014).

The present description provides therapeutic compositions and methods of using the same that are based on the surprising and unexpected discovery that chemically modified peptides as described herein are potent modulators of autophagy. The chemically modified peptides, for example, P140 peptides, as described herein are derived from the U1-70K spliceosomal protein. The described peptides and compositions comprising effective amounts of the same are effective for treating, preventing and/or ameliorating the symptoms of diseases characterized by an increased autophagy flux; i.e., hyper autophagy-related such as hyper-CMA autoimmune disorders. Accordingly, in certain additional aspects, the disclosure provides methods of making and using the described peptides and compositions comprising the same for the treatment, prevention and/or amelioration of the symptoms of diseases characterized by an hyper-autophagy, e.g., hyper-CMA, flux.

Thus, in one aspect the present description provides chemically modified peptides of SEQ ID NOs: 1, 2, 4 and 5, including derivatives, analogs and salt forms thereof.

In certain embodiment, the description provides an isolated peptide comprising or consisting of the amino acid sequence of SEQ ID NO: 1: RIHMVYSKRSGKPRG-YAFIEY [SEQ ID NO: 1], or

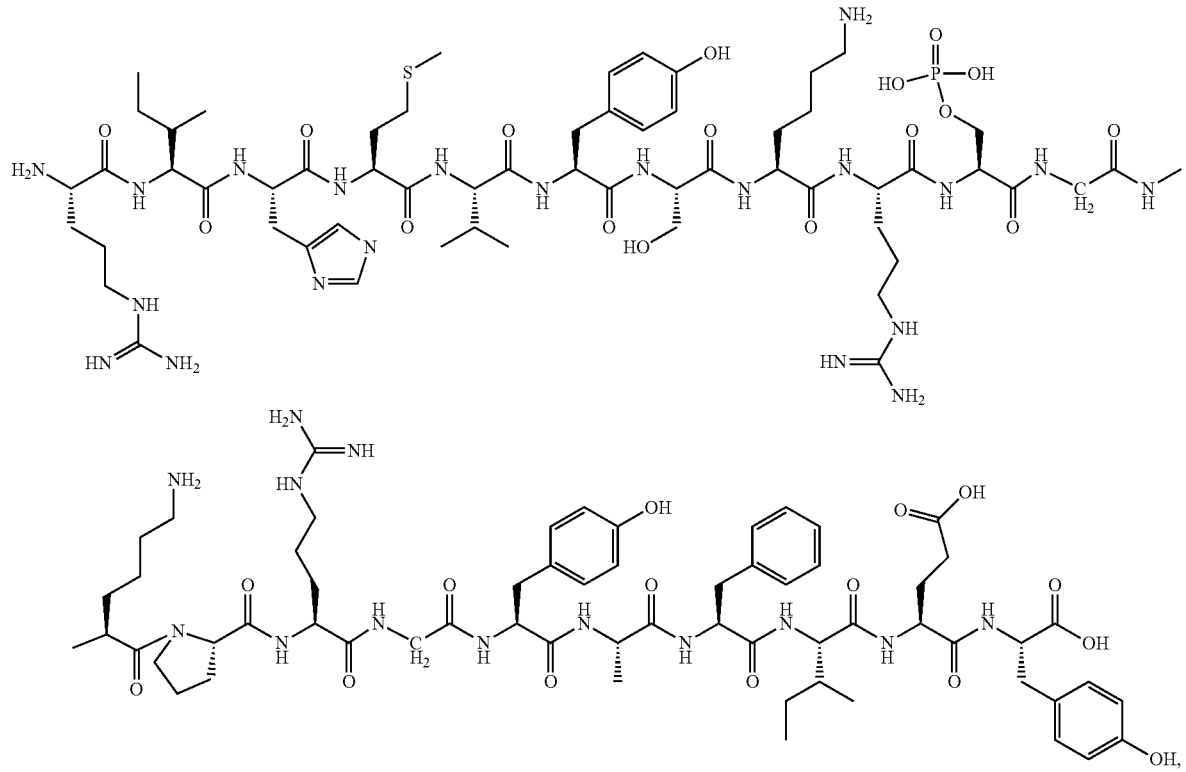

or salt thereof, having at least one post-translational modification selected from the group consisting of phosphorylation of a serine residue, oxidation of a methionine residue, and acetylation of a lysine residue, and combinations thereof. In an embodiment of this aspect, the description provides a composition comprising an isolated and/or chemically modified peptide (recombinant or synthesized) having or consisting of the amino acid sequence of SEQ ID NO: 1, or salt thereof, wherein the peptide comprises a phosphoserine at position 10. In certain embodiments, the description provides an isolated and/or chemically modified peptide (recombinant or synthesized) having or consisting of the amino acid sequence of SEQ ID NO: 1, or salt thereof, wherein the peptide comprises a phosphoserine at position 10, and an oxidized Methionine residue at position 4.

In certain additional embodiments, the peptide of SEQ ID NO:1 also comprises an acetylated lysine residue. In particular, said peptide of SEQ ID NO: 1 comprises a phosphoserine at position 10, and an oxidized Methionine residue at position 4, and an acetylation of one or both of the lysine at position 8 and 12, and more particularly further comprises a phosphoserine at position 7.

In certain embodiments, the description provides an isolated and/or chemically modified peptide (recombinant or synthesized), or a salt thereof, comprising or consisting of the amino acid sequence: IHMVYSKRSGKPRGYAFIEY [SEQ ID NO: 2], in which the Serine (S) at position 9 is phosphorylated, and the Methionine (M) at position 3 is oxidized.

In certain embodiments, the description provides a peptide of compound I having the following formula:

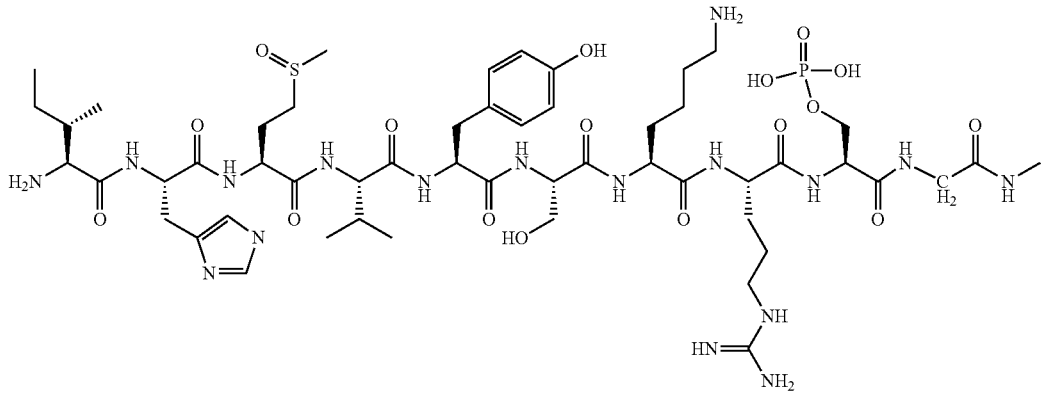

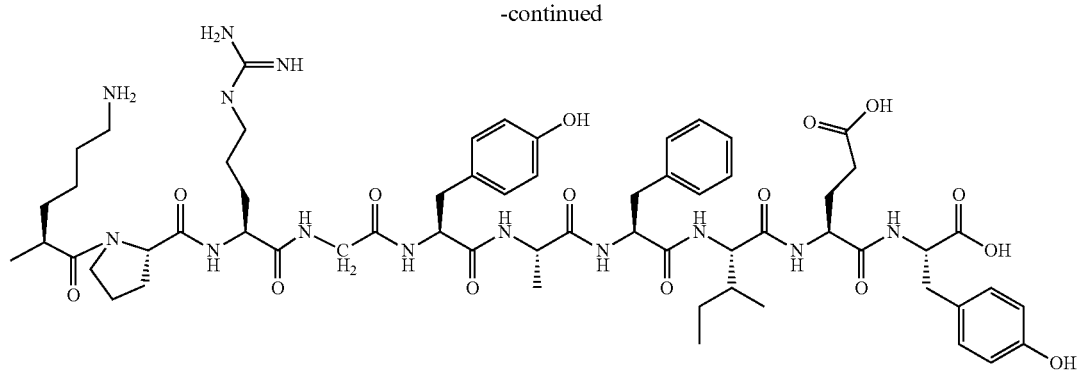

compound I can also be represented by:

[SEQ ID NO: 5]
IHM(O)VYSKRS(PO₃H₂)GKPRGYAFIEY in which "M(O)" represents oxidized methionine, and "S(PO₃H₂)" represents phosphoserine.

These peptides are derived from the human U1 snRNP 70 kDa protein (SEQ ID NO: 3), and correspond to the region delimited by the amino acid segment extending from the residue 132 to the residue 151 of SEQ ID NO: 3. Formally, the residue which is phosphorylated corresponds to the amino acid at the position 140 from the first methionine of SEQ ID NO: 3, and the residue which is oxidized corresponds to the amino acid at the position 134 from the first methionine of SEQ ID NO: 3.

In certain aspects, the description provides an isolated and/or chemically modified peptide (recombinant or synthesized) comprising or consisting of the amino acid sequence of SEQ ID NO: 1, or salt thereof, having at least one post-translational modification selected from the group consisting of phosphorylation of a serine residue, oxidation of a methionine residue, and acetylation of a lysine residue, and combinations thereof. In an embodiment of this aspect, the description provides a composition comprising an isolated peptide having or consisting of the amino acid sequence of SEQ ID NO: 1, or salt thereof, wherein the peptide comprises a phosphoserine at position 10. In certain embodiments SEQ ID NO:1 also an oxidized Methionine residue at position 4. In certain additional embodiments, the peptide of SEQ ID NO:1 also comprises an acetylated lysine residue.

In additional aspects, the description provides an isolated and/or chemically modified peptide (recombinant or synthesized) comprising or consisting of the amino acid sequence of SEQ ID NO: 2, or salt thereof, having at least one post-translational modification selected from the group consisting of phosphorylation of a serine residue, oxidation of a methionine residue, and acetylation of a lysine residue, and combinations thereof. In an embodiment of this aspect, the description provides a composition comprising an isolated and/or chemically modified peptide (recombinant or synthesized) having or consisting of the amino acid sequence of SEQ ID NO: 2, or salt thereof, wherein the peptide comprises a phosphoserine at position 9, and an oxidized Methionine residue at position 3. In certain additional embodiments, the peptide of SEQ ID NO:2 also comprises an acetylated lysine residue.

In certain embodiments, the description provides a peptide of compound II having the following formula:

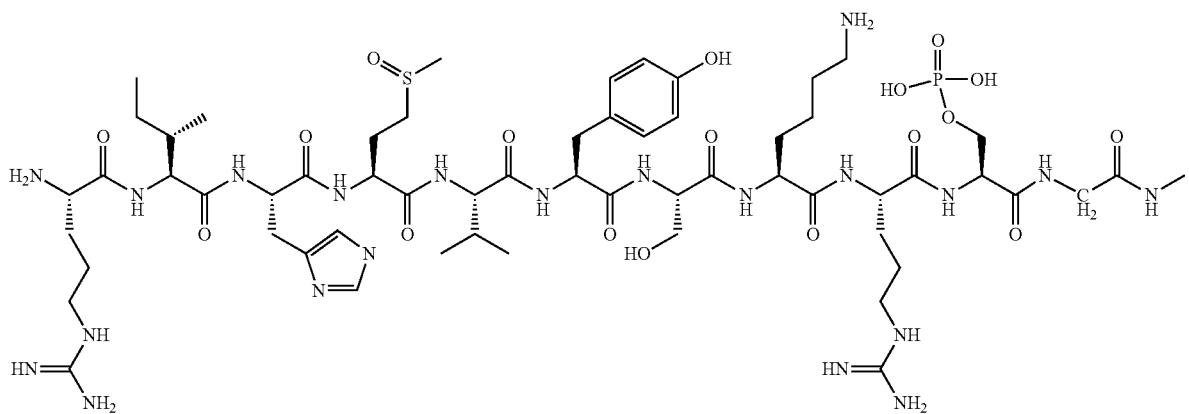

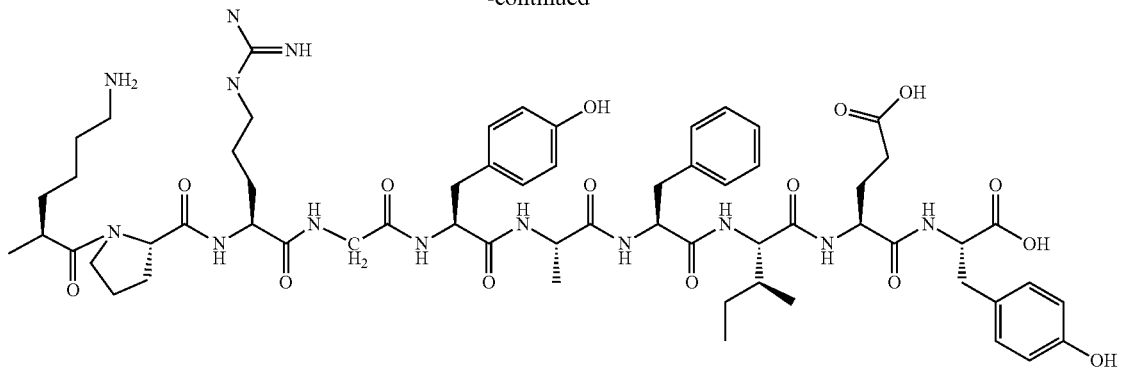

Compound II can also be represented by:

RIHM(O)VYSKRS(PO₃H₂)GKPRGYAFIEY [SEQ ID NO: 4]

in which M(O) represents oxidation of methionine, and S(PO₃H₂) represents the phosphorylation of serine.

Thus, the description provides peptides, or a salt thereof, comprising or consisting of the amino acid sequence chosen among the group consisting of SEQ ID NO: 4 and SEQ ID NO: 5.

In an additional embodiment, the description provides a composition comprising an effective amount of at least one peptide, or salt thereof, selected from the group consisting of the amino acid sequence SEQ ID NO: 2, comprising a phosphoserine at position 9, and oxidized Methionine at position 3; amino acid sequence of SEQ ID NO: 1, or salt thereof, wherein the peptide comprises a phosphoserine at position 10; the amino acid sequence SEQ ID NO: 1, comprising a phosphoserine at position 10, and an oxidized Methionine at position 4; and a combination thereof.

The description provides peptides, and/or salts thereof, comprising or consisting of the amino acid sequence chosen among the group consisting of SEQ ID NO: 1, 2, 4, 5 and combinations thereof, as well as compositions comprising the same.

In certain embodiments, the description provides an isolated and/or chemically modified peptide (recombinant or synthesized) having the amino acid sequence of SEQ ID NO: 1, comprising a phosphoserine at position 10. In certain embodiments, the P140 peptides also comprises an oxidized methionine at position 4 (e.g., SEQ ID NO: 4) (herein, also referred to as Compound II or P140(MO)). In certain embodiments, the description provides the peptide having the amino acid sequence as set forth in SEQ ID NO: 1, comprising a phosphoserine at position 10 and an oxidized methionine at position 4, or salt thereof, and a carrier, e.g., a pharmaceutically acceptable carrier. In certain additional embodiments, the description provides a composition, e.g., a therapeutic composition, comprising an effective amount of a peptide having the amino acid sequence as set forth in SEQ ID NO: 1, comprising a phosphoserine at position 10 and an oxidized methionine at position 4, or salt thereof, and a carrier, e.g., a pharmaceutically acceptable carrier.

According to the present description, the isolated and/or chemically modified peptide (recombinant or synthesized) having the amino acid sequence of SEQ ID NO: 1, 2, 4 or 5, respectively, is modified by at least one post-translational modification (modifications that occur after the synthesis of the peptides). In certain embodiments, the post-translational modification is selected from the group consisting of posphorylation (addition of a phosphate PO₃H₂), e.g., phosphorylation of a serine residue; oxidation, e.g., oxidation of a methionine residue; acetylation, e.g., acetylation of a lysine residue; and combinations thereof. In certain embodiments, the isolated and/or chemically modified peptide (recombinant or synthesized) having the amino acid sequence of SEQ ID NO: 1, 2, 4 or 5, respectively, is modified by at least two post-translational modifications.

In a preferred embodiment, the description provides an isolated and/or chemically modified peptide (recombinant or synthesized) having the amino acid sequence as set forth in SEQ ID NO: 2 comprising a phosphoserine at position 9 and an oxidized methionine at position 3, or salt thereof. In certain embodiments, the description provides the peptide having the amino acid sequence as set forth in SEQ ID NO: 2, comprising a phosphoserine at position 9 and an oxidized methionine at position 3, or salt thereof, and a carrier, e.g., a pharmaceutically acceptable carrier. In certain additional embodiments, the description provides a composition, e.g., a therapeutic composition, comprising an effective amount of a peptide having the amino acid sequence as set forth in SEQ ID NO: 2, comprising a phosphoserine at position 9 and an oxidized methionine at position 3, or salt thereof, and a carrier, e.g., a pharmaceutically acceptable carrier.

In another embodiment, the description provides an isolated and/or chemically modified peptide (recombinant or synthesized) having the amino acid sequence as set forth in SEQ ID NO: 4 comprising a phosphoserine at position 10, and an oxidized methionine at position 4, or salt thereof. In certain embodiments, the description provides the peptide having the amino acid sequence as set forth in SEQ ID NO: 4 comprising a phosphoserine at position 10, and an oxidized methionine at position 4, or salt thereof, and a carrier, e.g., a pharmaceutically acceptable carrier. In certain additional embodiments, the description provides a composition, e.g., a therapeutic composition, comprising an effective amount of a peptide having the amino acid sequence as set forth in SEQ ID NO: 4 comprising a phosphoserine at position 10, or salt thereof, and an oxidized methionine at position 4, and a carrier, e.g., a pharmaceutically acceptable carrier.

In another embodiment, the description provides an isolated and/or chemically modified peptide (recombinant or synthesized) having the amino acid sequence as set forth in SEQ ID NO: 5 comprising a phosphoserine at position 9 and an oxidized methionine at position 3, or salt thereof. In certain embodiments, the description provides the peptide having the amino acid sequence as set forth in SEQ ID NO: 5 comprising a phosphoserine at position 9 and an oxidized methionine at position 3, or salt thereof, and a carrier, e.g., a pharmaceutically acceptable carrier. In certain additional embodiments, the description provides a composition, e.g., a therapeutic composition, comprising an effective amount of a peptide having the amino acid sequence as set forth in SEQ ID NO: 5 comprising a phosphoserine at position 9 and an oxidized methionine at position 3, or salt thereof, and a carrier, e.g., a pharmaceutically acceptable carrier.

Surprisingly and unexpectedly, it was discovered that the peptides as described herein are more stable in vitro compared to the non-oxidized counterpart. The stability is measured as disclosed in the example section. The phosphorylated-oxidized peptide is less spontaneously degraded in solution compared to the non-oxidized counterpart, said stability enhancing its biological properties. In addition, the inventors have surprisingly identified that the methionine oxidation enhances the peptide stability, without affecting the biological effect of such peptide, contrary to the teaching of the prior art. Indeed, it is largely reported in the art that proteins or peptides containing oxidized methionine have disruptions in their three-dimensional structure and/or bioactivity. The modified peptides as described herein have an affinity for HSC70 protein essentially identical to the non-oxidized counterpart as disclosed in the example section.

In certain embodiments, the oxidation occurs in the Methionine (M) at position 9 of SEQ ID NO: 2, or at position 10 of SEQ ID NO: 1, which are the equivalent positions to the position 134 of SEQ ID NO: 3. The sulfur atom is oxidized as illustrated below:

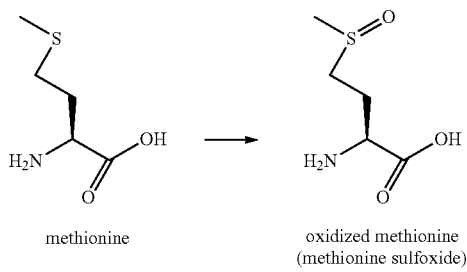

methionine → oxidized methionine (methionine sulfoxide)

The above peptides (SEQ ID NO: 1, 2, 4 and 5) can be synthesized by techniques commonly used in the art, such as biological synthesis or chemical synthesis. Biological synthesis refers to the production, in vivo, in vitro or ex vivo, of the peptide of interest, by the transcription and translation of a nucleic acid molecule coding for said peptides.

For instance the nucleic acid sequence:

[SEQ ID NO: 6]
MGNATHCAYATGGTNTAYWSNAARMGNWSNGGNAARCCNMGNGGNT
AYGCNTTYATHGARTAYTRR is transcribed and translated either in an in vitro system, or in a host organism, in order to produce the peptide SEQ ID NO: 1. The produced peptide is thus purified according to well known techniques.

Chemical synthesis consists to polymerize the desired peptide by adding the required amino acids. A method is disclosed in the example section.

It is possible to chemically synthesize the peptides SEQ ID NO: 1 and 2 by classical Fmoc (N-[9-fluorenyl] methoxycarbonyl) solid-phase chemistry and purified by reversed-phase high-performance liquid chromatography (HPLC; Neimark and Briand, 1993; Monneaux et al., 2003, Eur. J. Immunol. 33,287-296; Page et al., 2009, PloS ONE 4,e5273).

It is also possible to directly synthesize the peptides SEQ ID NO: 1 and 2, in which respective residues at position 10 and 9 are phosphorylated. For this purpose, during the peptide synthesis a Fmoc-Ser(PO(Obz)OH)—OH-type serine derivative was used, at the desired position.

Phosphate group (—$PO_3H_2$) can also be added after the synthesis of the peptide, according to protocols well known in the art.

Serine can be phosphorylated by incubating the peptides SEQ ID NO: 1 or 2 with specific serine kinase chosen among Protein Kinase A or C (PKA or PKC) or casein kinase II, in presence of adenosine triphosphate (ATP). The peptides are thus phosphorylated in one serine (at position 6 or 9 of SEQ ID NO: 2, or at position 7 or 10 of SEQ ID NO: 1), or both serine. The desired phosphorylated peptide is separated from the others for instance by chromatography.

A chemical addition of —$PO_3H_2$ can also be added at the specific position (at position 9 of SEQ ID NO: 2, or at position 10 of SEQ ID NO: 1), by using specific protective group, that the skilled person can easily choose according to his common knowledge.

Any other techniques known in the art, allowing the specific phosphorylation of serine, can be used.

In certain embodiments, the oxidation of Methionine is performed according to the following process:

treating with either with $H_2O_2$, 20 mM, at 37° C. for 4 hours, or in a solution of dimethylsulfoxyde (DMSO; $Me_2SO$), 0.1M plus HCl 0.5 M, at 22° C. for 30 to 180 min.

Any other techniques known in the art, allowing the specific oxidation of methionine, can be used.

In any of the aspects or embodiments described herein, the peptide(s) provided by the description can be present in a form of a salt known to a person skilled in the art, such as, e.g., sodium salts, ammonium salts, calcium salts, magnesium salts, potassium salts, acetate salts, carbonate salts, citrate salts, chloride salts, sulphate salts, amino chlorhydate salts, borhydrate salts, benzensulphonate salts, phosphate salts, dihydrogenophosphate salts, succinate salts, citrate salts, tartrate salts, lactate salts, mandelate salts, methane sulfonate salts (mesylate) or p-toluene sulfonate salts (tosylate). This list is provided by way of example and is not meant to be limiting on the present invention. For example, the skilled person can easily determine, according to his knowledge, the appropriate salt.

In an additional embodiment, the description provides a peptide comprising or consisting of the amino acid sequence:

[SEQ ID NO: 1]
RIHMVYSKRSGKPRGYAFIEY, comprising a phosphoserine at position 10. In certain embodiments, the phosphorylated peptide further comprises an oxidized Methionine at position 4, or salt thereof. In one advantageous embodiment, the invention relates to the peptide as defined above, consisting of the amino acid sequence SEQ ID NO: 4, or salt thereof.

Pharmaceutical Compositions

In another aspect the present description provides compositions comprising an effective amount of one or more of the peptides as described herein, and an excipient or carrier. Thus, in additional embodiments, the description also provides pharmaceutical compositions comprising at least a peptide as described herein, or a combination product as described above, further including a pharmaceutically acceptable carrier.

The peptides (also referred to herein as "active compounds") as described herein can be incorporated into pharmaceutical compositions suitable for administration. Such compositions typically comprise peptide and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The description provides methods for preparing pharmaceutical compositions. Such methods comprise formulating a pharmaceutically acceptable carrier with a peptide as described herein. Such compositions can further include additional active agents as described above. Thus, the invention further includes methods for preparing a pharmaceutical composition by formulating a pharmaceutically acceptable carrier with a peptide as described herein, and one or more additional active compounds.

A pharmaceutical composition of the invention is formulated to be compatible with its intended route of administration. Examples of routes of administration include parenteral, e.g., intravenous, intradermal, subcutaneous, oral, nasal (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol; antioxidants such as ascorbic acid or sodium bisulfate; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, chlorobutanol, phenol, ascorbic acid, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In certain embodiments of the methods provided herein, the method includes the step of administering a dosage from about 100 ng to about 5 mg of a therapeutic or pharmaceutical composition as described herein. In certain embodiments, e.g., in human, the pharmaceutical composition as described herein may contain mannitol as carrier, and the composition is administered from 10 μg to 500 μg, preferably 200 μg, in a single administration.

In certain additional aspects, the dosage regimen can be reproduced from 1 to 3 times/week, every week to every four week for as long as needed with therapeutic windows and thus for several years. In a preferred embodiment, the dosage regimen is once every 4 weeks of treatment but can be repeated twice a year for several years. An example of administration is: one injection of 200 μg of peptide, every 4 weeks, for 12 weeks (i.e. 3 injections separated from each other by 4 weeks). The treatment can be prolonged by administration every 6 months.

Preferred pharmaceutically acceptable carriers can comprise, for example, xanthan gum, locust bean gum, galactose, other saccharides, oligosaccharides and/or polysaccharides, starch, starch fragments, dextrins, British gum and mixtures thereof. Advantageously, the pharmaceutically acceptable carrier is of natural origin. The pharmaceutically acceptable carrier can be, or can further comprise, an inert saccharide diluent selected from a monosaccharide or disaccharide. Advantageous saccharide is mannitol.

Advantageously, the invention relates to a pharmaceutical composition as defined above, which is in the form of a liposome, or nano particles, or in the form of a solution. An advantageous solution is a solution comprising from 1 to 15%, in particular about 10% of mannitol. The solution should be iso-osmolar.

The invention also relates to a drug comprising a combination product as defined above, for a simultaneous, separate or sequential use.

Therapeutic Methods

In an additional aspect, the present description provides methods for treating, preventing or ameliorating the symptoms of an autoimmune disease or chronic inflammatory disease or disorder comprising administering an effective amount of a therapeutic composition as described herein to a subject in need thereof, wherein the composition is effective for treating, preventing and/or ameliorating at least one symptom of a chronic inflammation-related disease or disorder.

In an additional aspect, the present description provides methods for treating, preventing or ameliorating the symptoms of a hyper autophagy-related immune system disease or disorder, e.g., a hyper-CMA-related autoimmune disease, comprising administering an effective amount of a therapeutic composition as described herein to a subject in need thereof, wherein the composition is effective for treating, preventing and/or ameliorating at least one symptom of the hyper-autophagy, e.g., hyper-CMA-related disease or disorder. (e.g., Table 3, below).

In certain embodiments, the disease or disorder is a disease or disorder related to excessive or increased autophagy, e.g., CMA, for example at least one of rheumatoid arthritis (RA), multiple sclerosis (MS), myopathies, muscular dystrophy (MD), Crohn's disease (CD), Chronic obstructive pulmonary disease (COPD) fibromyalgia, polymyositis, pulmonary disease, chronic immune thrombocytopenia (ITP), neuropsychiatric lupus, Gougerot-Sjögren syndrome, rheumatoid arthritis, Guillain-Barré disease (chronic/CIDP), asthma (chronic), eosinophilic airway inflammation, irritable bowel syndrome (IBS or IBD), chronic inflammatory demyelinating polyradiculoneuropathy (CIDP), type II diabetes, regeneration of fat tissue, scleroderma, psoriasis, Alzheimer's, or Parkinson's.

In certain embodiments, the autoimmune disease is chosen among: autoimmune pathologies of the family of connective tissue diseases (non-specific systemic organ diseases), e.g., systemic lupus erythematosus (SLE), rheumatoid arthritis, mixed connective tissue disease, Sjögren's syndrome, or chronic juvenile arthritis; and/or organ-specific autoimmune pathologies, e.g., multiple sclerosis, insulin-dependent diabetes, Crohn's disease, or bullous diseases. In a preferred embodiment, the autoimmune disease is SLE.

In an additional aspect, the description also provides methods of treating an autoimmune disease, comprising the step of administering to a subject (e.g., a patient such as a mammal, e.g., a human) in need of such treatment an effective amount of a pharmaceutical composition as described herein, wherein the composition is sufficient to effectuate said treatment. In another aspect, the description provides a composition as described herein for use in a method for treating an autoimmune disease comprising the step of administering to a patient in need thereof, an effective amount of a pharmaceutical composition as described herein, wherein the composition is sufficient to effectuate said treatment.

In certain embodiments, the autoimmune disease is chosen among: autoimmune pathologies of the family of connective tissue diseases (non-specific systemic organ diseases), e.g., rheumatoid arthritis, mixed connective tissue disease, Sjögren's syndrome, or chronic juvenile arthritis; and/or organ-specific autoimmune pathologies, e.g., multiple sclerosis, Crohn's disease, or bullous diseases. In a preferred embodiment, the autoimmune disease is SLE.

The description also provides a drug comprising a peptide as described herein, and/or a combination as described herein, for its use as drug, in particular for the treatment of autoimmune diseases.

Without being bound by any particular theory, the inventors hypothesize that HSC70 binding is important for mediating the phosphopeptide binding and internalization, and therefore, mediates the therapeutic effects of the peptides as described herein. Accordingly, the description also provides a method of treating or ameliorating a condition caused by overexpression of HSC70 at the cell surface comprising the steps of administering an effective amount of a phosphopeptide, e.g., a modified peptide as described herein, to a patient in need thereof, wherein the peptide treats or effectuates the amelioration of at least one symptom of the condition.

The peptide consisting of the amino acid sequence SEQ ID NO: 1, in which the Serine at position 10 is phosphorylated corresponds to the below Compound III:

EXAMPLES

Example 1: Chemical Synthesis of the Peptides

P140 peptide and P140(MO) were synthesized using classical Fmoc (N-[9-fluorenyl] methoxycarbonyl) solid-phase chemistry and purified by reversed-phase high-performance liquid chromatography (HPLC; Neimark and Briand, 1993; Monneaux et al., 2003, Eur. J. Immunol. 33,287-296; Page et al., 2009, PloS ONE 4,e5273). Their homogeneity was checked by analytical HPLC, and their identity was assessed by LC/MS on a Finnigan LCQ Advantage Max system (Thermo Fischer Scientific). After completion of the reaction, the peptides were purified by HPLC.

In order to introduce the phosphorylation at the serine residue equivalent to the residue 140 of SEQ ID NO: 3, an Fmoc-Ser(PO(Obz)OH)—OH-type serine derivative was used. The coupling time is increased to 30 minutes and a second coupling is carried out systematically. After cleavage in acid medium, each peptide is precipitated by cold ether, solubilized in a solution of water and acetonitrile and finally lyophilized. The peptides are then purified by RP-HPLC, their integrity and their purity has been analyzed by analytic HPLC and by mass spectrometry (Maldi-TOF). Oxidation is introduced as mentioned above.

Example 2: Stability of the Peptides

The stability of the peptide SEQ ID NO: 1 in which the serine at position 10 is phosphorylated and the methionine at position 4 is oxydized (P140(MO)), and the peptide SEQ ID NO: 1 in which the serine at position 10 is phosphorylated (P140) was measured at 37° C., in a solution of 10% (v/v) mannitol. For each peptide, 3 concentrations have been tested: 200, 100 and 50 µg/mL.

At the indicated time, the integrity of P140 and P140(MO) peptides was measured in saline by high-performance liquid chromatography from the area of the peak corresponding to the intact peptide.

Figure 3:
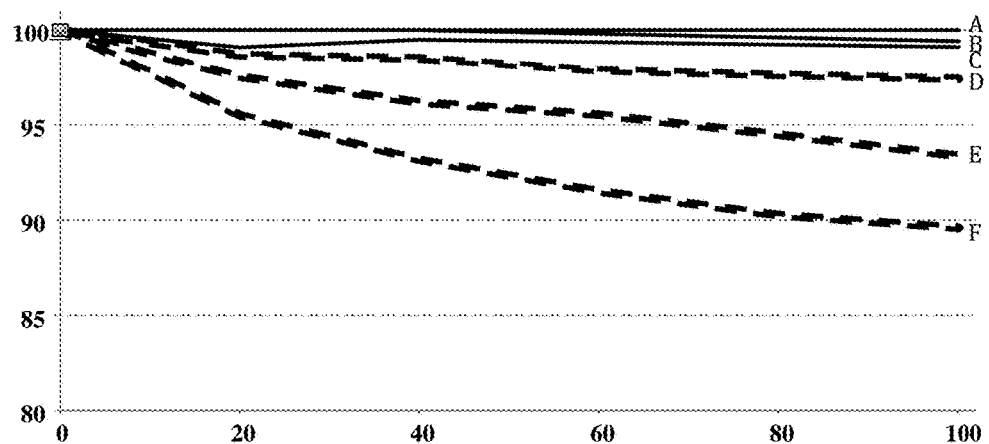
FIG. 3. Demonstrates the stability at 37° C. of the peptide according to the invention (Compound II) compared to the stability of the peptide consisting of SEQ ID NO: 1, in which serine at position 10 is phosphorylated. The graph represents the percentage of stability over the time (expressed in days). Curves A-C represent the stability of Compound II at a concentration of 200, 100 and 50 μg/ml, respectively. Curves D-F represent the stability of the peptide consisting of SEQ ID NO: 1, in which serine at position 10 is phosphorylated at a concentration of 200, 100 and 50 μg/ml, respectively.

Results are shown in FIG. 3.

The following tables 1 and 2 summarize the results:

TABLE 1

| | | P140(MO) | | | P140 | | |
|---|---|---|---|---|---|---|---|
| | Days | 200 µg/mL | 100 µg/mL | 50 µg/mL | 200 µg/mL | 100 µg/mL | 50 µg/mL |
| Stability (%) | 0 | 100 | 100 | 100 | 100 | 100 | 100 |
| | 20 | 100 | 99.1 | 100 | 98.7 | 97.5 | 95.5 |
| | 40 | 100 | 99.5 | 100 | 98.5 | 96.2 | 93.2 |
| | 60 | — | — | — | 97.9 | 95.5 | 91.5 |
| | 80 | — | — | — | 97.6 | 94.5 | 90.3 |
| | 100 | 100 | 99.1 | 99.4 | 97.4 | 93.4 | 89.6 |

TABLE 2

| | Days | P140(MO) 200 µg/mL | P140(MO) 100 µg/mL | P140(MO) 50 µg/mL | P140 200 µg/mL | P140 100 µg/mL | P140 50 µg/mL |
|---|---|---|---|---|---|---|---|
| Stability (%) | Linear equation | y = 100 | y = −0.0064x + 100.11 | y = −0.0064x + 99.677 | y = −0.0238x + 99.535 | y = −0.0612x + 99.25 | y = −0.099x + 98.299 |
| | Correlation coefficient | N/A | $R^2 = 0.8571$ | $R^2 = 0.4157$ | $R^2 = 0.8854$ | $R^2 = 0.9538$ | $R^2 = 0.9065$ |
| | 95% of stability (predicted) | ∞ | 2 years + 2 months | 2 years | 6 months | 2 months | 1 months |

Stability is measured by using the HPLC peak surface.

P140 M(O) stability remains unchanged (100%, 99.1% and 99.4%) over 100 days at 37° C., for each of the tested concentrations (50 to 200 µg/ml).

P140 stability decreases over the time and is reduced after 100 days at 37° C. (97.4%, 93.4% et 89.6%) for each of the tested concentrations (50 to 200 µg/ml).

These data demonstrate that the oxidation of the methionine in the peptide P140 enhance the stability of the peptide. P140(MO) is stable at all the tested concentration over 100 days.

Example 3: Therapeutic Effect of the Peptides in MRL/Lpr Mice

MRL/lpr mouse strain is a mouse substrain that is genetically predisposed to the development of systemic lupus erythematosus-like syndrome, which has been found to be clinically similar to the human disease. It has been determined that this mouse strain carries a mutation in the fas gene. Also, the MRL/lpr is a useful model to study behavioural and cognitive deficits found in autoimmune diseases and the efficacy of immunosuppressive agents [Monneaux et al., 2003, Eur. J. Immunol. 33,287-296].

2.1-Survival Analysis

Five-week-old female MRL/lpr mice received P140 or peptide P140(MO) intravenously as described (Monneaux et al., 2003, Eur. J. Immunol. 33,287-296). All experimental protocols were carried out with the approval of the local Institutional Animal Care and Use Committee (CREMEAS). As control, mice were injected with NaCl.

Twenty mice were used for each peptide or NaCl.

Figure 4:
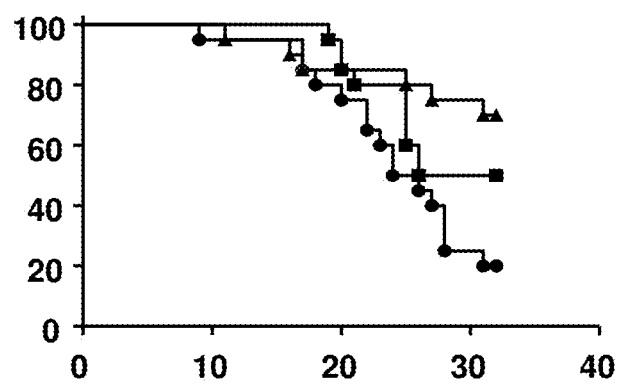
FIG. 4. Kaplan-Meier graph representing the cumulative survival rate (in percent) over the time (expressed in weeks) of mice injected with NaCl (line with circles), the peptide consisting of SEQ ID NO: 1, in which serine at position 10 is phosphorylated (line with squares) and compound II according to the invention (lines with triangles).

The results are shown in FIG. 4.

A Log-rank (Mantel-Cox) Test has been applied and the results are the following: NaCl vs P140 p=0.0686, NaCl vs P140(MO) p=0.0026, P140 vs P140 M(O) p=0.2366.

The Median survival of mice is NaCl=25 weeks, P140=29 weeks and P140 (MO)>40 weeks. These results demonstrate the efficacy of the P140(MO) peptide in vivo in the treatment of lupus, in mice.

2.2-Proteinuria Analysis

Proteinuria of the above mice was measured in fresh urine using Albustix (Bayer Diagnostics) and was semi-quantitatively estimated according to a 0-4 scale recommended by the manufacturer (no proteinuria=0; traces=1; 1+=2; 2+=3; 3+=4; 4+=5).

Figure 5:
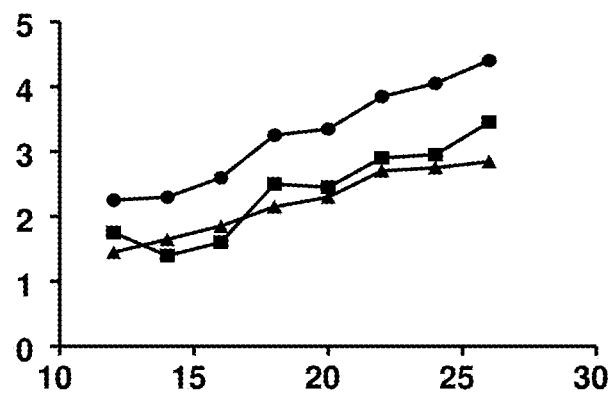
FIG. 5. Proteinuria score over the time (expressed in weeks) of mice injected with NaCl (line with circles), the peptide consisting of SEQ ID NO: 1, in which serine at position 10 is phosphorylated (line with squares) and compound II according to the invention (lines with triangles).

The results are shown in FIG. 5.

In this figure, it is observed that the proteinuria is less important and appears lately in P140 M(O)-treated mice compared to the untreated mice.

2.3-Cellularity Analysis

Figure 6:
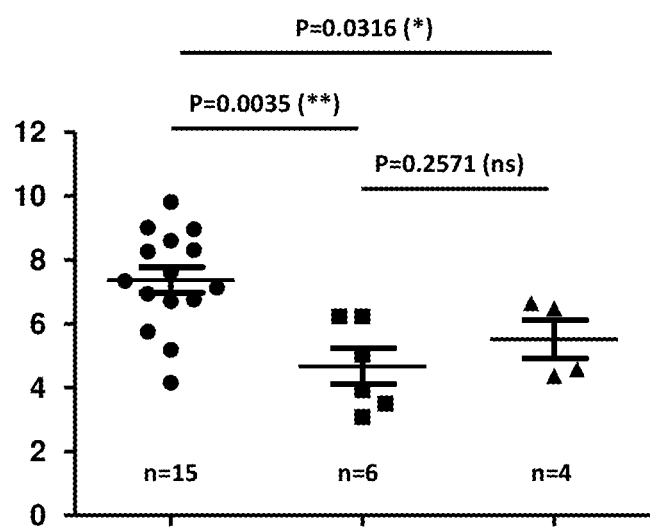
FIG. 6. Measure of the hypercellularity of MRL/lpr mice cells. Y-axis represents the number of cells/mL of blood ($\times 10^6$), in mice treated with NaCl (circles), the peptide consisting of SEQ ID NO: 1, in which serine at position 10 is phosphorylated (squares) and compound II according to the invention (triangles).

MRL/lpr mice were injected with 100 µg/100 µL of P140 or P140(MO) and cellularity (preipheral blood) was studied 5 days after this unique injection. The count includes all the leucocytes. In view of the low number of tested mice, a non parametric statistical test has been realised Mann-Whitney). The results are shown in FIG. 6.

Thus, in an acute murine model of lupus, peptide of SEQ ID NO: 4 was able to decrease peripheral hypercellularity and delays biological and clinical signs of the disease with an efficacy at least similar to that of P140, or better.

Statistics

Statistical tests were performed using GraphPad Prism version 5.0. The two-way ANOVA test was used to analyze statistical significance of proteinuria differences between control and peptide-treated groups of mice. Survival of control and P140 analogue-treated female MRL/lpr mice was analyzed by the Kaplan-Meier method, and the significance of differences was determined by the log-rank test. For the other variables, statistical significance was assessed using the Student's t-test. p values less than 0.05 were considered significant.

Example 4: Affinity of the Peptides for HSC70 Protein

BIAcore 3000 system (Biacore AB) was used to evaluate the binding of P140 peptides to HSC70 protein (Page et al., 2009, and 2011). Sensor chip CMS, surfactant P20, amine coupling kit containing N-hydroxysuccinimide (NHS) and N-ethyl-N'-dimethylaminopropyl carbodiimide (EDC), 2-(2-pyridinyldithio)ethaneamine (PDEA) and ethanolamine were from Biacore AB. Biosensor assays were performed with HBS-EP buffer as running buffer (10 mM HEPES, 150 mM NaCl, 3 mM EDTA, 0.005% surfactant P20, pH 7.4). The compounds were diluted in the running buffer. The sensor chip surface was regenerated after each experiment by injecting 10 µL of 10 mM HCl. Recombinant bovine HSC70 (Stressgen) was immobilized on flow cells of a CMS sensor chip through its thiol groups using 35 µL PDEA in 50 mM borate buffer, pH 8.3 on the NHS/EDC-activated matrix. Then, 35 µL of HSC70 (100 µg/mL in formate buffer, pH 4.3) were injected until a response of 13,000 response units (RU) corresponding to 13 ng/mm² of HSC70 was immobilized. Twenty µL of a 50 mM cysteine/1 M NaCl solution was used to saturate unoccupied sites on the chip. The direct binding measurement of P140 peptides to HSC70 was carried out at 25° C. with a constant flow rate of 20 µL/min. P140 peptide and analogues were injected in the flux at different concentrations for 3 min, followed by a dissociation phase of 3 min. The kinetic parameters were calculated using the BIAeval 3.1 software on a personal computer. Analysis was performed using the simple 1:1 Langmuir binding model. The specific binding profiles were obtained after subtracting the response signal from the control empty channel and from blank-buffer injection. The fitting to each model was judged by the $\chi^2$ value and randomness of residue distribution compared to the theoretical model.

Figure 7:
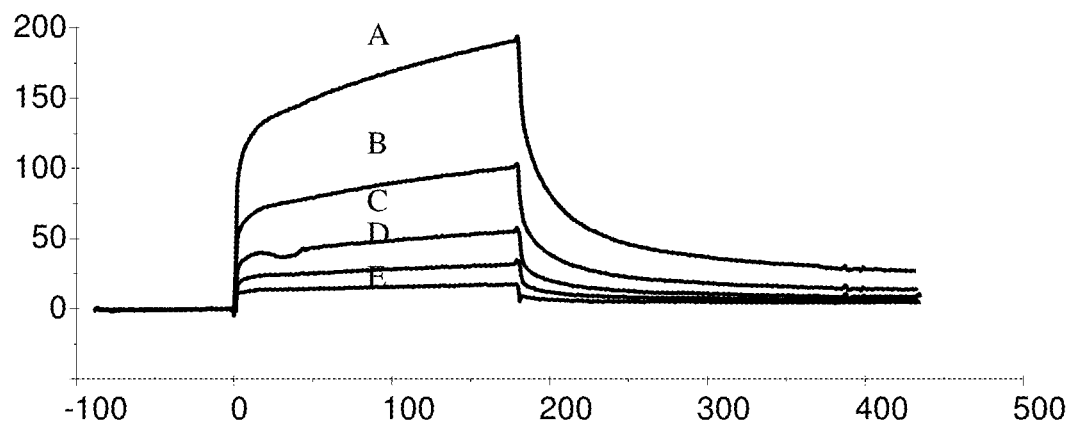
FIG. 7. Measure of the affinity for the HSC70 protein of the peptide consisting of SEQ ID NO: 1, in which serine at position 10 is phosphorylated. Curves corresponds to the Biacore response over the time (expressed in seconds) by using the peptide consisting of SEQ ID NO: 1, in which serine at position 10 is phosphorylated at a concentration of 25 μM(A), 12.5 μM(B), 6.25 μM(C), 3.12 μM(D) and 1.56 μM (E).
Figure 8:
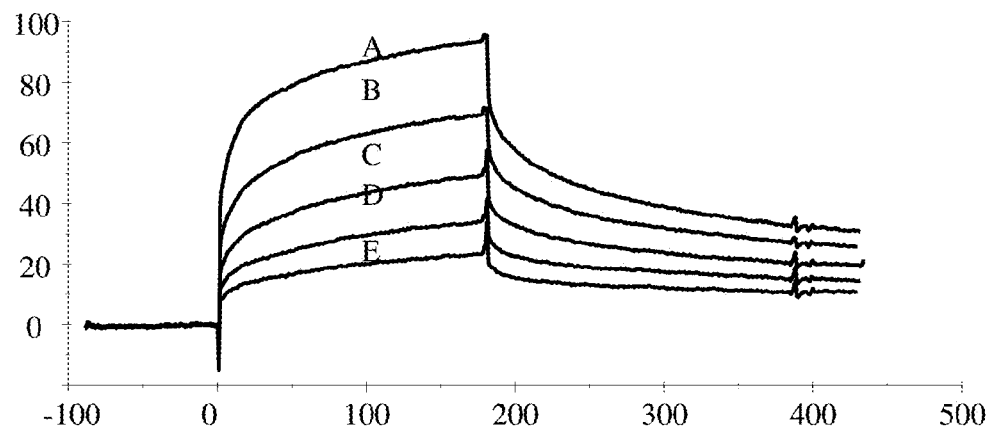
FIG. 8. Measure of the affinity of the compound II according to the invention, for the HSC70 protein. Curves correspond to the Biacore response over the time (expressed in seconds) by using the compound II at a concentration of 25 μM(A), 12.5 μM(B), 6.25 μM(C), 3.12 μM(D) and 1.56 μM (E).

Results are shown in Tables 3 and 4, and in FIGS. 7 and 8

These tables demonstrate that the affinity for HSC70 is not statistically different between P140 and P140 M(O) peptides.

Thus, these two peptides bind with the same efficiency HSC70.

Example 5: Effect of P140 Peptide in RA

In this example, a P140 peptide (21-mer linear peptide) encompassing the sequence 131-151 of the spliceosomal U1-70K protein and containing a phosphoserine residue at position 140, was tested. After P140 treatment, an accumulation of autophagy markers SQSTM1 and MAP1LC3 was observed in MRL/lpr B cells, consistent with a down-regulation of autophagic flux (Page et al., 2011). Chaperone-mediated autophagy (CMA) was also found to be a target of P140 peptide and it was demonstrated that P140 peptide inhibitory effect on CMA is likely tied to its ability to interact with HSPA8 chaperone protein (Page et al., 2009) and to alter the composition of HSPA8 heterocomplexes (Macri et al., in press). Expression of both HSPA8 and the limiting CMA component LAMP-2A, which is increased in MRL/lpr B cells, is down-regulated after treating mice with P140 peptide (Page et al., 2011; Macri et al., in press). It was shown further that P140, but not the non-phosphorylated peptide that is not protective against disease development in mice (Monneaux et al., 2003), uses the clathrin-dependent endo-lysosomal pathway to enter into MRL/lpr B lymphocytes and accumulates in the lysosomal lumen where it may directly hamper lysosomal HSPA8 chaperoning functions, and also destabilize LAMP-2A in lysosomes as a result of its effect on HSP90 (Macri et al., in press). This dual effect may interfere with the endogenous (auto)antigen processing and loading to MHCII molecules and as a consequence, lead to the lower activation of autoreactive T cells that was previously shown experimentally (Monneaux et al., 2004; Monneaux et al., 2007).

Recent research suggests that autophagy is potentially increased in RA, as well as in other autoimmune diseases (Table 3; Wilhelm & Muller, submitted). This activation has been proposed for Crohn's disease (CD), RA, polymyositis (PM) and multiple sclerosis (MS), but not in autoimmune diabetes where, in contrast, autophagy might be decreased.

TABLE 3

List of autoimmune diseases with autophagy failures

| Autoimmune diseases | Associated genes | Cellular dysfunctions | References |
|---|---|---|---|
| CD[(1)] | ATG16L1 | | Hampe et al. 2007 |
| | IRGM | | Glas et al. 2003; Lu et al. 2013 |
| SLE | ATG5 | | Harley et al. 2008; Zhou et al. 2011 |
| | DRAM1 | | Yang et al. 2013 |
| | PRDM1 | | Zhou et al. 2011 |
| | | MaA increased in T cells from MRL/lpr and NZB/W mice and from patients: autophagic vacuoles over-represented (WB, EM)[(2)] | Gros et al. 2012 |
| | | MaA deregulated in naive CD4+T cells from patients: autophagosome-associated marker MAP1LC3 increased (WB) | Alessandri et al. 2012 |
| | | MaA hyper-activated in B cells from NZB/W mice and naive B cells of patients; autophagosomes number increased (FACS, FM) | Clarke et al. 2014 |
| | | MaA activated in macrophages from lupus-prone mice and patients: ATG5, ATG12 and BECN1 expression increased | Li et al. 21014 |
| | | Increased HSPA8 expression in B and T cells of MRL/lpr mice (WB, FACS, PCR) | Page et al. 2011 |
| | | Increased LAMP-2A and CTSD expression in B cells of MRL/lpr mice; lysosomes are defective in MRL/lpr mice (WB, FACS, Q-PCR, in vitro assay for CMA) | Macri et al., in press |
| RA | ATG5 | | Orozco et al. 2011 |
| | ATG7 | | Lin et al. 2013 |
| | BECN1 | | Lin et al. 2013 |
| | | MaA activated in osteoclasts from patients: BECN1 and ATG7 expression increased (WB) | Lin et al. 2013 |
| | | Autophagic process increased in synovial fibroblast: p62 and MAP1LC3 expression increased (WB, FM) | Kato et al. 2014 |
| PM | | MaA activated in muscle fiber: MAP1LC3, CTSD and CTSB expression increased (WB) | Nogalska et al. 2010 |
| MS | ATG5 | | Mayes et al. 2014, Alirezaei et al. 2009 |
| | | MaA deregulated in T cells: ATG5 expression increased (WB, PCR) | Alirezaei et al. 2009 |
| Type 1 diabetes | | MaA diminished in diabetic mouse heart: MAP1LC3 and ATG5/12 expression reduced (WB, FM) | Xu et al. 2013; Yamahara et al. 2013 |

(1) Abbreviations: ATG, autophagy related-gene; BECN1, beclin-1; CD, Crohn's disease; CMA, chaperone-mediated autophagy; CTSB, cathepsins B; CTSD, cathepsins D; DRAM1, damage-regulated autophagy modulator; EM, electron microscopy; FM, fluorescence microscopy; HSPA8, heat shock protein 8; IRGM, Immunity-related GTPase family M protein; LAMP-2A, lysosomal-associated membrane protein 2A; MaA, macroautophagy, MAP1LC3, microtubule-associated protein light chain 3; MS, multiple sclerosis; PCR, polymerase chain reaction; PM, polymyositis; PRDM1, positive regulatory domain I-binding factor 1; RA, rheumatoid arthritis; SLE, systemic lupus erythematosus; WB, Western blot. (2) The method used to evaluate these changes is given in parentheses.

Ex vivo, P140 does not induce proliferation of peripheral T cells from lupus patients (in contrast to the non-phosphorylated form that does and in contrast to the data shown ex vivo in MRL/lpr context) but generates secretion of high levels of regulatory cytokine IL-10 in cell cultures (Monneaux et al., 2005). No proliferation and no IL-10 production were observed in the cultures when T cells from patients with other autoimmune diseases were tested (Monneaux et al., 2005). Patients (n=27) with rheumatoid arthritis (RA), primary Sjögren's syndrome, autoimmune deafness, polymyositis, primary billiary cirrhosis and autoimmune hepatitis were evaluated, as well as 4 patients hospitalized for non-autoimmune or infectious diseases.

These data (raised with small groups of patients) led us to conclude that most likely peptide P140 very specifically stimulates peripheral lupus CD4$^+$ T cells but not T cells from patients with other pathophysiological conditions (Monneaux et al., 2005). These data were also against the potential effect of P140 peptide as a possible regulator of autophagy defects in these diseases.

Next, P140 peptide was administered in a model of mice that develop a RA-like disease (we anticipated to use this mouse model as a negative control of MRL/lpr-lupus prone mice). This model, called collagen-induced arthritis (CIA) mouse model, is the most commonly studied autoimmune model of RA. In this model, autoimmune arthritis is induced by immunizing DBA/1 mice with an emulsion of complete Freund's adjuvant (CFA) and type II collagen (CII), and typically, the first signs of arthritis appear in 21-28 days after immunization (Brand et al., 2007). CIA shares several pathological features with human RA, and CII is a major protein in cartilage, the target tissue of RA. Pathological features include synovial hyperplasia, mononuclear cell infiltration, and cartilage degradation. Susceptibility in these mice is linked to the expression of specific MHC class II genes, DBA/1 have H-2$^q$ haplotype.

P140 peptide was thus administered intravenously to DBA/1 mice at day −1, +7, +14 and +20 in a setting close to the one we used in MRL/lpr mice (100n/injection/mouse). CII in CFA was injected at days +1 and +21 (200 μg, intradermal route). Mouse weight and their clinical score were followed using very classical procedure. Biological parameters were also evaluated (i.e. T cell response, antibody response, joint histology, etc).

Figure 9:
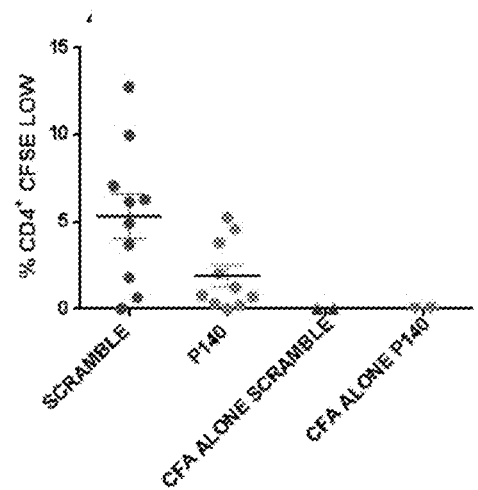
FIG. 9. CD4+ T splenocytes proliferation in the presence of 100 μg CII/mL in the cultures.

The results obtained in this experiment show that CD4$^+$ T splenocytes from mice that receive the scrambled peptide ScP140 proliferate normally ex vivo in the presence of CII added to the cultures (FIG. 9; 100 μg CII/mL; measured using the CFSE assay by FACS). In sharp contrast, however, proliferation was strongly diminished when CD4 T cells were collected from the spleen of mice that receive P140 peptide (p=0.0539 between ScP140 and P140).

No effect was observable when CD8$^+$ T cells were tested in the same conditions. Further results are awaited that will characterize this response in much more details. Histology will also complete these cellular data.

In any case, these results, which could not be anticipated, suggest an operational scheme that could mimic in RA the one found when we tested CD4$^+$ T cells from P140-treated MRL/lpr lupus-prone mice. In MRL/lpr mice, P140 induces a significant decrease of MHCII expression at the B cells surface (via its effect on CMA), lowering therefore the presentation of antigenic peptide by antigen-presenting cells, which, as a matter of consequences, leads to a decreased reactivity of peripheral autoreactive T cells and improvement of disease condition. Thus, the data show that P140 peptides can be effective in a variety of other pathological conditions in which reduction of CMA activity would be desired.

Nowadays, there is no available data showing at the cellular level that CMA is altered in RA. No information exists regarding the properties of lysosomes in this pathology. Future investigation should be focused on the possible demonstration that autophagic flux is increased in mice with RA and B cells from RA patients, and CMA altered in this setting.

Other pathophysiological settings will be tested to accumulate pertinent data, notably in CD, PM, scleroderma (SSc) and MS. Established murine models are available for CD (e.g. IL-10 KO mice, SAMP1/YitFc mice, or the peptidoglycan-polysaccharide model using inbred rats) and MS (mouse and rat models of experimental autoimmune encephalomyelitis, EAE). Nowadays, however, good animal models do not exist for PM and SSc.

Example 6: Endocytosis of P140 Particles

Figure 10:
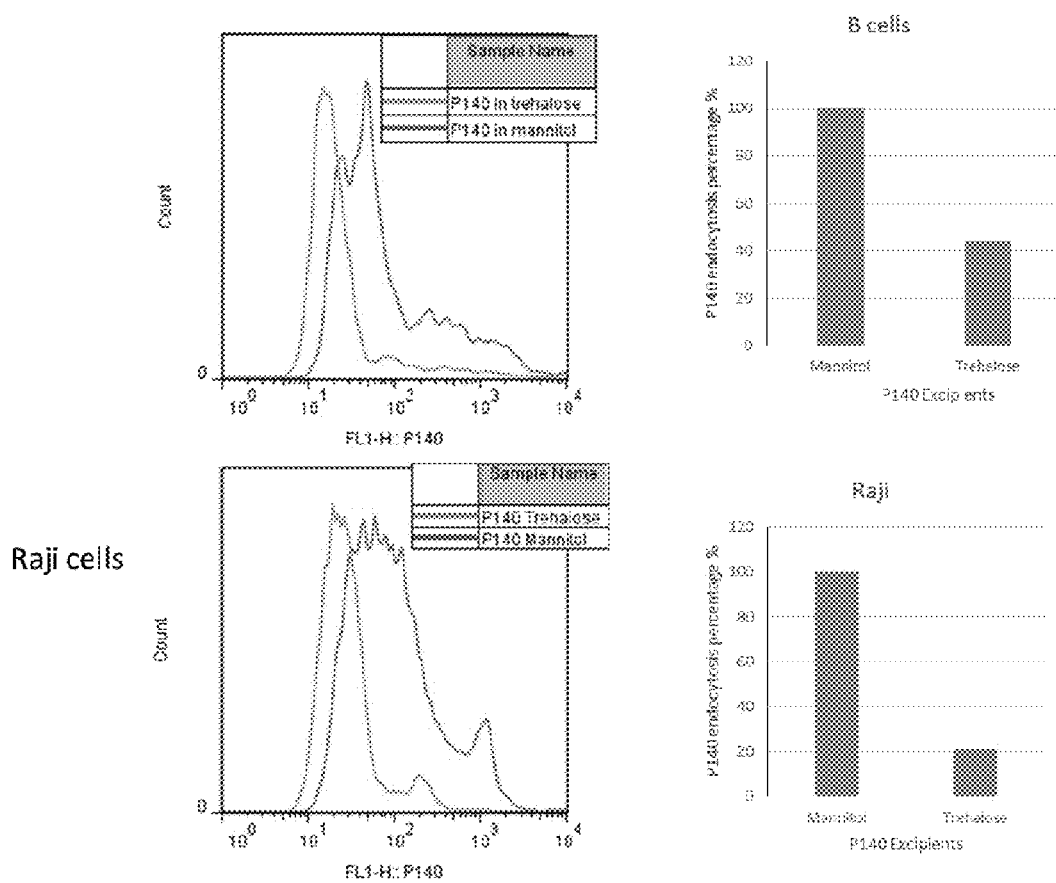
FIG. 10. Cellular uptake of fluorescent P140 peptide in 5.4% mannitol or 10% trehalose in MRL/lpr B cells and Raji cells as visualized by flow cytometry. B cells were from 12-14 week-old MRL/lpr mice (primary cells); Raji cells are an established cell line derived in 1963 from B-lymphocyte of a patient with Burkitt's lymphoma. Much less cellular uptake of P140 in both MRL/lpr B cells and Raji cells when the peptide is diluted in trehalose than in mannitol.
Figure 11:
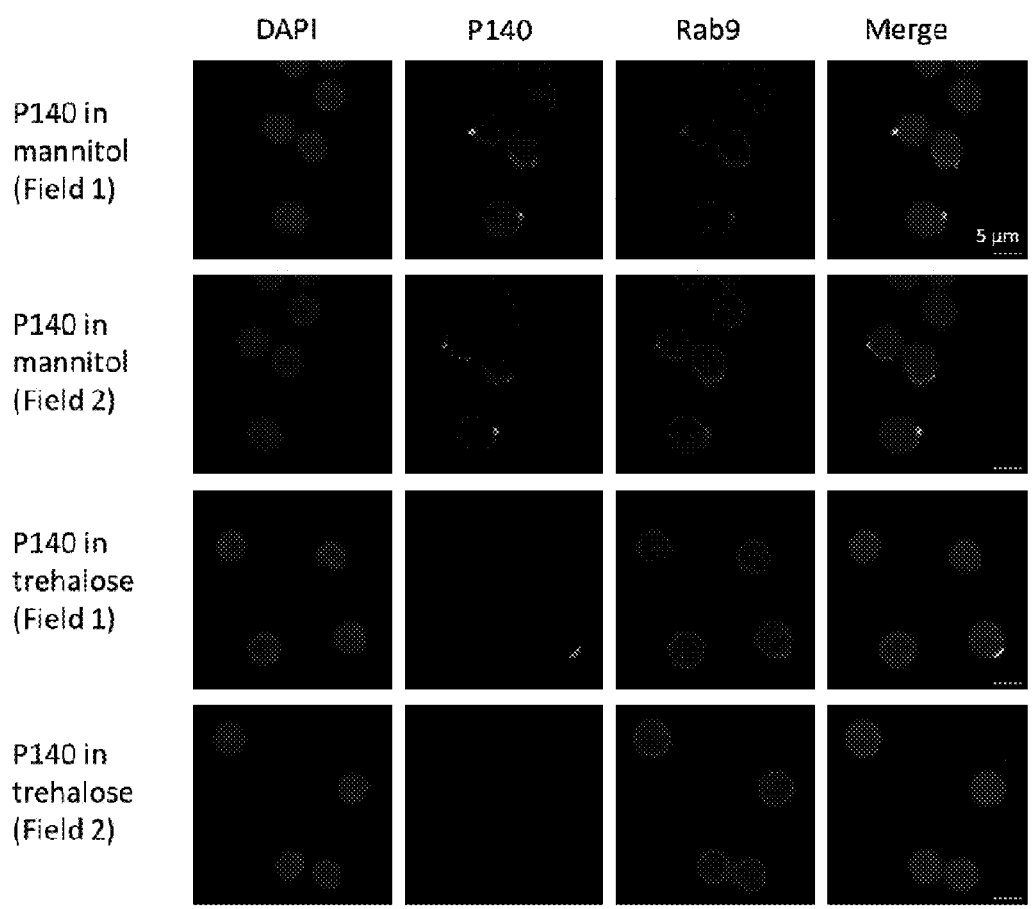
FIG. 11. Confocal images of B cells of FIG. 10. All confocal images were taken in the same microscopic settings. Rab9 (red) identifies the late ensosomal compartment where P140 localizes before homing into lysosomes DAPI (blue) identifies DNA. The results confirm the flow cytometry results that when in trehalose, P140 peptide (in green) enters B cells much less.

For P140 peptide activity, HSC70 binding and endocytosis appear to be important. It is believed that endocytosis must occur through the clathrin route. This implies that peptide+excipient should have a size in the range of 30 to 500 nm in diameter. For example P140+mannitol are in the 100 nm region whereas P140+trehalose are below 10 nm and therefore not effective binding to HSC70. For example, FIG. 10 shows cellular uptake of fluorescent P140 peptide in 5.4% mannitol or 10% trehalose in MRL/lpr B cells and Raji cells as visualized by flow cytometry. B cells were from 12-14 week-old MRL/lpr mice (primary cells); Raji cells are an established cell line derived in 1963 from B-lymphocyte of a patient with Burkitt's lymphoma. Much less cellular uptake of P140 in both MRL/lpr B cells and Raji cells when the peptide is diluted in trehalose than in mannitol. This result was confirmed using confocal microscopy (FIG. 11). The confocal images show the late endosomal compartment where P140 localizes before homing into lysosomes; DAPI identifies DNA. The results confirm the flow cytometry results that when in trehalose, P140 peptide enters B cells much less (See Tables 4 and 5).

TABLE 4

P140 on HSC70

| Peptide - concentration | ka (1/Ms) | kd (1/s) | Rmax (RU) | RI (RU) | Conc of analyte | KA (1/M) | KD (M) | Req (RU) | kobs (1/s) | Chi2 |
|---|---|---|---|---|---|---|---|---|---|---|
|  | 450 |  | 83.3 |  |  |  |  |  |  | 3.17 |
| P140- 1.56 μM |  | 3.12E−03 |  | 12.1 | 1.56 u | 1.44E+05 | 6.94E−6 | 15.3 | 3.82E−03 |  |

TABLE 4-continued

P140 on HSC70

| Peptide - concentration | ka (1/Ms) | kd (1/s) | Rmax (RU) | RI (RU) | Conc of analyte | KA (1/M) | KD (M) | Req (RU) | kobs (1/s) | Chi2 |
|---|---|---|---|---|---|---|---|---|---|---|
| P140- 3.12 µM | | 3.12E−03 | | 20.9 | 3.12 u | 1.44E+05 | 6.94E−6 | 25.8 | 4.52E−03 | |
| P140- 6.25 µM | | 3.12E−03 | | 33.8 | 6.25 u | 1.44E+05 | 6.94E−6 | 39.5 | 5.93E−03 | |
| P140- 12.5 µM | | 3.12E−03 | | 62.5 | 12.5 u | 1.44E+05 | 6.94E−6 | 53.6 | 8.74E−03 | |
| P140- 25 µM | | 3.12E−03 | | 118 | 25 u | 1.44E+05 | 6.94E−6 | 65.2 | 0.0144 | |

TABLE 5

P140(MO) on HSC70

| Peptide - concentration | ka (1/Ms) | kd (1/s) | Rmax (RU) | RI (RU) | Conc of analyte | KA (1/M) | KD (M) | Req (RU) | kobs (1/s) | Chi2 |
|---|---|---|---|---|---|---|---|---|---|---|
| | 1.15E+3 | | 39 | | | | | | | 1.18 |
| P140(MO)- 1.56 µM | | 2.20E−3 | | 14 | 1.56 u | 5.24E+5 | 1.91E−6 | 17.6 | 4.00E−03 | |
| P140(MO)- 3.12 µM | | 2.20E−3 | | 18.7 | 3.12 u | 5.24E+5 | 1.91E−6 | 24.2 | 5.80E−03 | |
| P140(MO)- 6.25 µM | | 2.20E−3 | | 25.9 | 6.25 u | 5.24E+5 | 1.91E−6 | 29.9 | 9.40E−03 | |
| P140(MO)- 12.5 µM | | 2.20E−3 | | 36.9 | 12.5 u | 5.24E+5 | 1.91E−6 | 33.9 | 0.0166 | |
| P140(MO)- 25 µM | | 2.20E−3 | | 53.4 | 25 u | 5.24E+5 | 1.91E−6 | 36.3 | 0.031 | |

Example 7. Anti-Inflammatory Effect of the P140 Phosphopeptide in a 15-Day Model of Eosinophilic Airway Inflammation Induced by Ovalbumin in Mice The anti-inflammatory effect of the P140 phosphopeptide was evaluated when administered locally (intranasally) or systemically (intravenously) in a 15-day model of hypereosinophilic airway inflammation in mice.

The P140 phosphopeptide was solubilized in sterile water (Braun) and 10× concentrate sterile saline was added to adjust osmolarity to 300 mosm. Osmolarity was controlled with a micro osmometer (Loser, type 15) and validated (302 mosm).

The P140 phosphopeptide was used in vivo at the dose of 4 mg/kg by intranasal (i.n.) and intravenous (i.v.) routes. Control animals received equivalent volumes (1 ml/kg for i.n. and 2 ml/kg for i.v.) of saline (Table 6).

Figure 12:
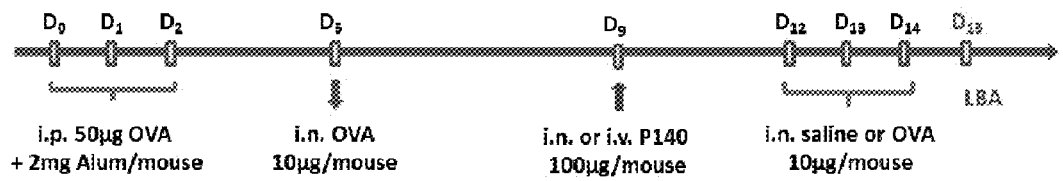
FIG. 12. The anti-inflammatory effect of a P140 phosphopeptide was evaluated when administered locally (intranasally) or systemically (intravenously) in a 15-day model of hypereosinophilic airway inflammation in mice. Briefly, nine-week-old male Balb/c mice were sensitized by intraperitoneal (i.p.) injections of a mixture containing 50 µg OVA and 2 mg alum in 0.1 ml saline. Mice were challenged by i.n. administration of 25 µl of OVA on day 5, then 25 µl of OVA and/or saline on day 12, 13 and 14. Mice were treated by i.v. injection (2 ml/kg) or i.n. administration (1 ml/kg) of P140 or solvent on day 9.

Nine-week-old male Balb/c mice were sensitized by intraperitoneal (i.p.) injections of a mixture containing 50 µg OVA (Sigma-Aldrich) and 2 mg alum (Sigma-Aldrich) in 0.1 ml saline. Mice were challenged by i.n. administration of 25 µl of OVA on day 5, then 25 µl of OVA and/or saline on day 12, 13 and 14. Mice were treated by i.v. injection (2 ml/kg) or i.n. administration (1 ml/kg) of P140 or solvent on day 9 (See FIG. 12).

TABLE 6

| Group Number | Number of Mice | Treatment | Challenge |
|---|---|---|---|
| 1 | 1 | Solvent | Saline |
| 2 | 2 | P140 (i.n.) | Saline |
| 3 | 2 | P140 (i.v.) | Saline |
| 4 | 5 | Solvent | OVA |
| 5 | 6 | P140 (i.n.) | OVA |
| 6 | 6 | P140 (i.v.) | OVA |

BAL was performed twenty-four hours after LPS challenge as described (Daubeuf, F. and Frossard, N. 2012. Performing Bronchoalveolar Lavage in the Mouse. *Curr Protoc Mouse Biol* 2:167-175). Mice were anaesthetized IP (Ketamine 150 mg/kg—Xylasine 10 mg/kg). Blood was collected from the heart, centrifuged at 10,000 g for 2 min and serum stored at −20° C. After semi-excision of the trachea, a plastic cannula was inserted, and airspace washed with 0.5 ml of 0.9% NaCl injected with a 1 ml syringe. This procedure was performed 10 times. The initial concentrated supernatant of the 2 first lavages (volume=2×0.5 ml administered, ~0.5 ml recovered) was collected for cytokine measurements. The remaining BAL fluid was centrifuged (300 g for 5 min, 4° C.), and cell pellets pooled. The cell pellet was suspended in 500 µl of 0.9% NaCl and used for total cell counts evaluated on a Muse® Cell Analyser. Differential cell counts were assessed by flow cytometry (LSRII® cytometer, BD Bioscience). BAL cells were added with FCblock (0.5 µl, 553142, BD Bioscience) in a black microplate, incubated for 20 min at room temperature. Then, marker antibodies were added: CD11c-FITC (557400, BD bioscience), Gr-1-Pe-eFluor610 (61-5931-82, eBioscience), CD11b-APC-Cy7 (557657, BD bioscience), CD45-AlexaFluor700 (103128, BioLegend), CD3-BV605 (564009, BD bioscience), CD19-PE-Cy7 (552854, BD bioscience). Antibodies were incubated with BAL cells for 30 min at room temperature before DAPI (5 µl, BD bioscience) addition, and flow cytometry was performed immediately.

Data are presented as means±SEM. Differences between groups were tested for statistical significance using one-way ANOVA followed by Tukey's post-test. For statistical analysis, control groups 1, 2 and 3 were pooled. Data were considered significantly different when p≤0.05.

Analysis of airway cells recovered in BAL fluid in control mice challenged with saline shows that the P140 phosphopeptide administered i.n. or i.v. has little effect per se on the number of cells recovered in BAL fluid as compared to vehicle (saline), and in particular has no pro-inflammatory effect. (See Table 7).

TABLE 7

|  | Mice | Total cells | Macrophages | Eosinophils | Neutrophils | T cells | B cells |
|---|---|---|---|---|---|---|---|
| Ctrl | NL415-2_1 | 333 568 | 328 362 | 149 | 223 | 4 834 | 149 |
| P140-IN | NL415-2_2 | 392 461 | 388 102 | 168 | 56 | 4 135 | 112 |
| P140-IN | NL415-2_8 | 438 573 | 434 029 | 103 | 61 | 4 180 | 242 |
| P140-IV | NL415-2_4 | 341 738 | 335 658 | 110 | 259 | 5 311 | 70 |
| P140-IV | NL415-2_15 | 340 389 | 335 200 | 166 | 133 | 4 790 | 266 |
| OVA | NL415-2_3 | 1 658 393 | 563 095 | 888 525 | 78 637 | 128 136 | 21 766 |
| OVA | NL415-2_5 | 1 098 900 | 331 150 | 626 131 | 45 797 | 95 822 | 25 365 |
| OVA | NL415-2_9 | 1 546 822 | 388 693 | 1 022 052 | 68 833 | 67 243 | 25 216 |
| OVA | NL415-2_14 | 1 468 429 | 418 191 | 833 452 | 95 942 | 120 843 | 15 380 |
| OVA | NL415-2_19 | 1 064 136 | 302 118 | 624 692 | 80 691 | 56 635 | 24 624 |
| P140-IN | NL415-2_6 | 862 995 | 271 110 | 490 306 | 57 542 | 44 036 | 25 606 |
| P140-IN | NL415-2_7 | 942 875 | 322 340 | 497 948 | 60 787 | 61 800 | 32 251 |
| P140-IN | NL415-2_10 | 1 120 576 | 247 391 | 737 671 | 62 354 | 73 159 | 26 562 |
| P140-IN | NL415-2_11 | 1 592 328 | 538 954 | 839 841 | 95 173 | 118 360 | 23 383 |
| P140-IN | NL415-2_16 | 1 377 755 | 436 210 | 792 249 | 47 346 | 101 951 | 33 156 |
| P140-IN | NL415-2_20 | 1 028 339 | 286 509 | 615 171 | 65 366 | 61 293 | 13 236 |
| P140-IV | NL415-2_12 | 949 720 | 439 265 | 425 928 | 42 783 | 41 744 | 10 219 |
| P140-IV | NL415-2_13 | 780 142 | 442 055 | 272 763 | 21 442 | 43 881 | 15 209 |
| P140-IV | NL415-2_17 | 809 921 | 244 523 | 473 105 | 59 616 | 32 677 | 14 027 |
| P140-IV | NL415-2_18 | 895 467 | 293 070 | 470 027 | 76 867 | 55 502 | 17 417 |
| P140-IV | NL415-2_21 | 738 452 | 342 134 | 327 186 | 40 275 | 28 857 | 11 003 |
| P140-IV | NL415-2_22 | 885 821 | 379 565 | 429 469 | 31 756 | 45 030 | 10 922 |

Figure 13:
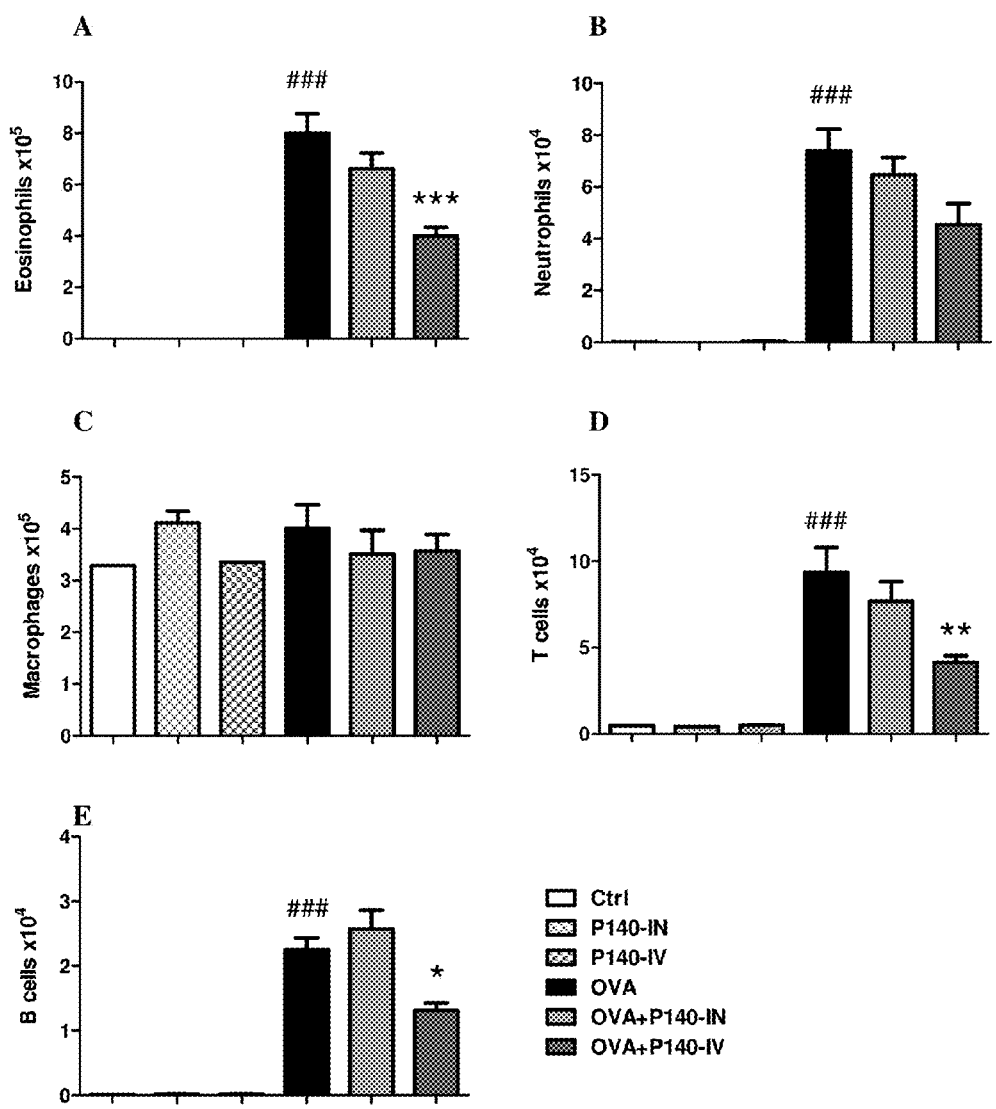
FIG. 13. Effect of the P140 phosphopeptide on airway inflammatory cell recruitment in an ovalbumin-induced airway hypereosinophilia model in Balb/c mice. Balb/c mice were immunised to OVA (day 0, 1 and 2) and challenged with OVA (day 5) and OVA or saline (day 12, 13 and 14). P140 was administered i.n. (P140-IN) or i.v. (P140-IV) at the dose of 4 mg/kg on day 9. Absolute numbers of A) eosinophils, B) neutrophils, C) macrophages, D) T cells, and E) B cells in BAL are shown. Blocks are means and bars are SEM values (n=1 or 6 per group). ### p≤0.001 vs control group and * p≤0.05,  p≤0.01 and * p≤0.001 vs OVA group.

In ovalbumin-challenged mice, the total number of inflammatory cells recovered in BAL fluid increases significantly. This effect is related to significant increased influx of eosinophils, neutrophils, T and B cells (### $p<0.001$; FIG. 13).

The P140 phosphopeptide administered i.v. (4 mg/kg) significantly decreases eosinophil (−50%, * $p<0.001$), T cells (−66%,  $p<0.01$) and B cells (−42%, * $p<0.05$) recruitment, as well as neutrophils recruitment (−38%) although not below the significance cutoff. By contrast, administered locally by i.n. route, the P140 phosphopeptide shows little effect on inflammatory cell recruitment in BAL, suggesting P140 is acting through a systemic effect.

The project aimed at studying whether the P140 phosphopeptide could have an anti-inflammatory effect administered locally by i.n. or systemically by i.v. in a 15-day airway hypereosinophilia model in Balb/c mice sensitized and challenged with ovalbumin. We compared the effect of P140 administered i.n. or i.v. 2 days before OVA or saline challenge, i.e. 6 days before airway inflammatory cell recovery by bronchoalveolar lavage.

Thus, i.v. administration (4 mg/kg) of P140 shows anti-inflammatory effect in this airway hypereosinophilia model to OVA in Balb/c mice, whereas i.n. administration remains without substantial effect. This suggests the anti-inflammatory activity of P140 is a systemic (e.g., spleen, lymphoid organs, bone marrow) rather than a local effect.

Example 8. Study of the P140 Peptide Effect in a Mouse Model of Colonic Inflammation (DSS-Induced Model)

Normal mice (C57BL/6; 7 week-old; males) have received the P140 peptide (100/injection, iv route; 10 mice) or saline only (control group; 10 mice) at days −2 and −1. At day 0, dextran sodium sulfate (DSS; 2-3%) was administrated to induce the disease.

Animals were examined every day for body weight loss, stool consistency, diarrhea, and blood in the feces. The animals were sacrificed around day 14 or at any time if they are very sick (loss >25% body weight). Statistics: Mann-Whitney (exact)

Little difference in the DAI ($p=0.5386$). However, this clinical index is not very well adapted to mouse model. There was a significant increase of the colon size, reflecting a decrease of inflammation ($p=0.0011$). No difference of the body weight was observed between the two groups. However there was a tendency at day +3 and day +4. The blood appeared in the feces at day +6 in the control groups versus day +8 only in the P140 group Example 9. Effect of the P140 Phosphopeptide in a 31-Day Model of Eosinophilic Airway Inflammation Induced by House Dust Mite Extract (HDM) in Mice The aim of this study was to evaluate the effect of the P140 phosphopeptide administered systemically (intravenously) in a 31-day model of HDM-induced asthma in mice. The P140 phosphopeptide was solubilized in sterile water (Braun) and 10× concentrate sterile saline was added to adjust osmolarity to 300 mosm. Osmolarity was controlled with a micro osmometer (Loser, type 15) and validated (303 mosm). The P140 phosphopeptide was used in vivo at the dose of 4 mg/kg by intravenous (i.v.) routes. Control animals received equivalent volumes (2 ml/kg) of saline (Table 8).

TABLE 8

| Group Number | Number of Mice | Treatment | Challenge ($D_{28}$-$D_{30}$) |
|---|---|---|---|
| 1 | 6 | Solvent | Saline |
| 2 | 5 | P140 (i.v.) 4 mg/kg | Saline |
| 3 | 8 | Solvent | HDM |
| 4 | 8 | P140 (i.v.) 4 mg/kg | HDM |

Figure 14:
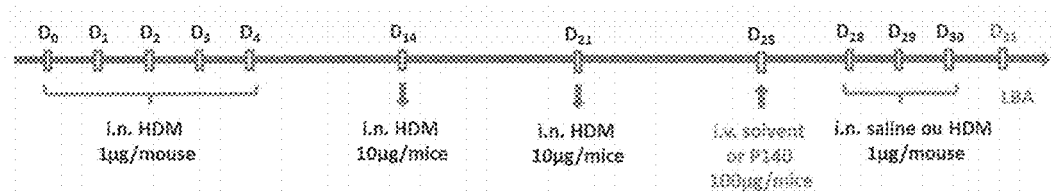
FIG. 14. Nine-week-old male Balb/c mice were sensitized by intranasal (i.n.) administration of HDM extract (Stallergenes): 1 µg in 25 µl saline on days 0, 1, 2, 3, 4, and 10 µg on days 14 and 21. Mice were challenged by i.n. administration of HDM (1 µg) and/or saline on days 28, 29 and 30. Mice were treated by i.v. injection (2 ml/kg) of P140 or solvent on day 25

Nine-week-old male Balb/c mice were sensitized by intranasal (i.n.) administration of HDM extract (Stallergenes): 1 µg in 25 µl saline on days 0, 1, 2, 3, 4, and 10 µg on days 14 and 21. Mice were challenged by i.n. administration of HDM (1 µg) and/or saline on days 28, 29 and 30. Mice were treated by i.v. injection (2 ml/kg) of P140 or solvent on day 25 (see FIG. 14).

Airway response to Methacholine (Flexivent®). On day 31, airway responses to PBS then methacholine were assessed using a forced oscillation technique (Flexivent®, SCIREQ, Montreal, Canada) as described (Daubeuf et al, Bioprotocol, 645, 2013). Mice were anesthetized with an intraperitoneal injection of xylasine (Rompun®; 1 mg/kg), followed fifteen minutes later by an intraperitoneal injection of pentobarbital sodium (3.64 mg/Kg). The trachea was exposed and an 18-gauge metal needle was inserted into the trachea. Airways were connected to a computer-controlled small animal ventilator, and quasi-sinusoidally ventilated with a tidal volume of 10 ml/Kg at a frequency of 150 breaths/min and a positive end-expiratory pressure of 2 cm H2O to achieve a mean respiratory volume close to that of spontaneous breathing. After baseline measurement, each mouse was challenged for 10 sec with an aerosol of PBS generated with an in-line nebulizer and administered directly through the ventilator. Then, aerosolized methacholine (MCh) at 50 mg/ml was administered for 10 sec. The effect of methacholine was calculated as the peak response, i.e. the mean of the three maximal values integrated for calculation of airway resistance (R, cm $H_2O.s\cdot mL^{-1}$), elastance (E, cm $H_2O.mL^{-1}$) and compliance (C, $mL\cdot cm\ H_2O^{-1}$).

BAL was performed after airway responsiveness measurement twenty-four hours after HDM challenge as described (Daubeuf et al. 2012). Mice were anaesthetized IP (Ketamine 150 mg/kg—Xylasine 10 mg/kg). Blood was collected from the heart, centrifuged at 10,000 g for 2 min and serum stored at −20° C.

After semi-excision of the trachea, a plastic cannula was inserted, and airspace washed with 0.5 ml of 0.9% NaCl injected with a 1 ml syringe. This procedure was performed 10 times. The initial concentrated supernatant of the 2 first lavages (volume=2×0.5 ml administered, approximately 0.5 ml recovered) was collected for cytokine measurements. The remaining BAL fluid was centrifuged (300 g for 5 min, 4° C.), and cell pellets pooled. The cell pellet was suspended in 500 µl of 0.9% NaCl and used for total cell counts evaluated on a Muse® Cell Analyser (Millipore). Differential cell counts were assessed by flow cytometry (LSRII® cytometer, BD Bioscience). BAL cells were added with FCblock (0.5 µl, 553142, BD Bioscience) in a black microplate, incubated for 20 min at room temperature. Then, marker antibodies were added: CD11c-FITC (557400, BD bioscience), Gr-1-PeeFluor610 (61-5931-82, eBioscience), F4/80-PE (12-4801-82, eBioscience), CD11b-APC-Cy7 (557657, BD bioscience), CD45-AlexaFluor700 (103128, BioLegend), CD3-BV605 (564009, BD bioscience), CD19-PE-Cy7 (552854, BD bioscience). Antibodies were incubated with BAL cells for 30 min at room temperature before DAPI (5 µl, BD bioscience) addition, and flow cytometry was performed immediately.

All mice were sensitized to HDM on days 0, 1, 2, 3, 4, 14, 21, and challenged either with saline (chronic asthma) or HDM (challenge with allergen). Results are presented as means±SEM. Differences between groups were tested for statistical significance using Student's t test for inflammatory cells and a two-way ANOVA followed by Bonferroni post-test for airway responses. Data were considered significantly different when p≤0.05.

TABLE 9

| Mice | | Total cells | Macrophages | Eosinophils | Neutrophils | T cells | B cells | DCs |
|---|---|---|---|---|---|---|---|---|
| NL715-3 | Ctrl | 979000 | 189 476 | 355 097 | 20 526 | 207 329 | 17 702 | 454 |
| NL715-26 | Ctrl | 767000 | 25 268 | 403 090 | 12 409 | 267 950 | 33 315 | 301 |
| NL715-30 | Ctrl | 386000 | 25 101 | 205 264 | 3 229 | 109 936 | 17 394 | 156 |
| NL715-33 | Ctrl | 768000 | 7 433 | 443 543 | 96 949 | 178 871 | 34 094 | 0 |
| NL715-35 | Ctrl | 913000 | 9 396 | 500 534 | 139 632 | 202 210 | 51 609 | 270 |
| NL715-37 | Ctrl | 801000 | 12 384 | 384 299 | 145 765 | 222 421 | 23 747 | 222 |
| NL715-1 | P140 | 448000 | 130 734 | 124 514 | 2 584 | 57 711 | 2 297 | 0 |
| NL715-5 | P140 | 1390000 | 267 885 | 450 346 | 35 734 | 323 623 | 44 688 | 484 |
| NL715-8 | P140 | 1510000 | 360 987 | 448 074 | 23 986 | 294 011 | 22 879 | 461 |
| NL715-11 | P140 | 815000 | 177 815 | 205 568 | 34 836 | 208 439 | 11 101 | 319 |
| NL715-25 | P140 | 484000 | 73 725 | 239 527 | 2 394 | 86 810 | 7 660 | 160 |
| NL715-4 | HDM | 2210000 | 90 204 | 1 054 534 | 438 909 | 507 196 | 29 645 | 231 |
| NL715-6 | HDM | 1810000 | 63 322 | 842 282 | 396 394 | 372 799 | 72 101 | 329 |
| NL715-8 | HDM | 2330000 | 73 284 | 1 312 253 | 365 962 | 444 121 | 62 314 | 457 |
| NL715-12 | HDM | 2190000 | 118 970 | 975 204 | 344 747 | 543 880 | 87 229 | 1 390 |
| NL715-14 | HDM | 3077000 | 89 870 | 1 466 110 | 663 136 | 573 814 | 193 834 | 915 |
| NL715-26 | HDM | 1470000 | 70 438 | 561 204 | 379 937 | 355 637 | 32 838 | 493 |
| NL715-36 | HDM | 3500000 | 185 702 | 1 850 328 | 73 656 | 1 076 717 | 124 546 | 4 018 |
| NL715-38 | HDM | 2430000 | 94 477 | 1 325 575 | 33 515 | 776 133 | 106 880 | 1 056 |
| NL715-2 | HDM + P140 | 2140000 | 58 705 | 955 824 | 606 700 | 400 329 | 59 092 | 1 034 |
| NL715-7 | HDM + P140 | 2992000 | 118 771 | 1 404 942 | 510 027 | 735 865 | 102 246 | 2 238 |
| NL715-10 | HDM + P140 | 2190000 | 314 326 | 636 065 | 500 004 | 383 074 | 42 085 | 1 793 |
| NL715-13 | HDM + P140 | 1010000 | 126 002 | 342 046 | 147 616 | 243 813 | 25 443 | 242 |
| NL715-27 | HDM + P140 | 2310000 | 34 364 | 1 283 190 | 371 317 | 469 834 | 116 814 | 586 |
| NL715-29 | HDM + P140 | 2220000 | 38 709 | 1 036 803 | 487 119 | 502 985 | 115 000 | 1 350 |
| NL715-31 | HDM + P140 | 1270000 | 29 121 | 538 210 | 284 503 | 334 784 | 53 947 | 733 |
| NL715-34 | HDM + P140 | 2410000 | 73 491 | 1 010 666 | 24 426 | 1 056 303 | 170 980 | 1 928 |

TABLE 9-continued

| Mice | | Rrs cmH2O · s/mL | | Crs mL/cmH2O | | Ers cmH2O/mL | |
|---|---|---|---|---|---|---|---|
| NL715-3 | Ctrl | 0.7599 | 4.7857 | 0.0586 | 0.0270 | 17.0739 | 38.9111 |
| NL715-30 | Ctrl | 0.4768 | 4.5462 | 0.0598 | 0.0172 | 18.7201 | 62.7641 |
| NL715-33 | Ctrl | 0.8317 | 8.8241 | 0.0466 | 0.0079 | 21.5098 | 147.5663 |
| NL715-35 | Ctrl | 0.5620 | 9.2466 | 0.0536 | 0.0053 | 18.6679 | 233.9273 |
| NL715-37 | Ctrl | 0.6316 | 11.2979 | 0.0501 | 0.0083 | 19.9557 | 143.6106 |
| NL715-1 | P140 | 0.5590 | 4.1067 | 0.0545 | 0.0304 | 18.3671 | 33.3720 |
| NL715-5 | P140 | 0.8945 | 9.4002 | 0.0498 | 0.0132 | 20.0811 | 84.9686 |
| NL715-8 | P140 | 0.5926 | 2.2229 | 0.0569 | 0.0380 | 17.5777 | 26.3200 |
| NL715-11 | P140 | 0.8074 | 4.0926 | 0.0541 | 0.0238 | 18.4893 | 42.4174 |
| NL715-25 | P140 | 0.4418 | 2.1844 | 0.0650 | 0.0370 | 15.3975 | 28.6047 |
| NL715-4 | HDM | 1.0205 | 9.0924 | 0.0537 | 0.0081 | 18.6618 | 128.4742 |
| NL715-6 | HDM | 0.9134 | 5.3264 | 0.0452 | 0.0099 | 21.0856 | 173.5647 |
| NL715-9 | HDM | 0.5742 | 6.4096 | 0.0537 | 0.0141 | 18.6092 | 104.8681 |
| NL715-12 | HDM | 0.8239 | 9.3617 | 0.0528 | 0.0056 | 18.9503 | 224.6403 |
| NL715-14 | HDM | 0.6807 | 7.4437 | 0.0493 | 0.0103 | 20.2677 | 156.8403 |
| NL715-28 | HDM | 0.6958 | 5.0333 | 0.0533 | 0.0126 | 18.7594 | 87.2749 |
| NL715-36 | HDM | 0.9430 | 14.8440 | 0.0573 | 0.0051 | 17.5010 | 214.1691 |
| NL715-38 | HDM | 0.7306 | 8.7652 | 0.0538 | 0.0152 | 18.5827 | 71.7470 |
| NL715-2 | HDM + P140 | 0.6405 | 5.6421 | 0.0554 | 0.0146 | 18.0582 | 79.8018 |
| NL715-7 | HDM + P140 | 0.6092 | 10.3886 | 0.0514 | 0.0075 | 19.4433 | 148.4985 |
| NL715-10 | HDM + P140 | 0.7972 | 11.9654 | 0.0528 | 0.0062 | 18.9515 | 188.1151 |
| NL715-13 | HDM + P140 | 0.5185 | 10.5419 | 0.0566 | 0.0065 | 17.6781 | 219.9720 |
| NL715-27 | HDM + P140 | 0.6804 | 8.8810 | 0.0492 | 0.0101 | 20.3326 | 125.7688 |
| NL715-29 | HDM + P140 | 0.6365 | 13.0087 | 0.0458 | 0.0060 | 21.8367 | 173.4582 |
| NL715-31 | HDM + P140 | 0.4744 | 7.0705 | 0.0552 | 0.0138 | 18.1106 | 72.6033 |
| NL715-34 | HDM + P140 | 0.5456 | 9.7688 | 0.0589 | 0.0081 | 16.9723 | 131.8035 |

Airway Responses in Chronic Asthma

Figure 15:
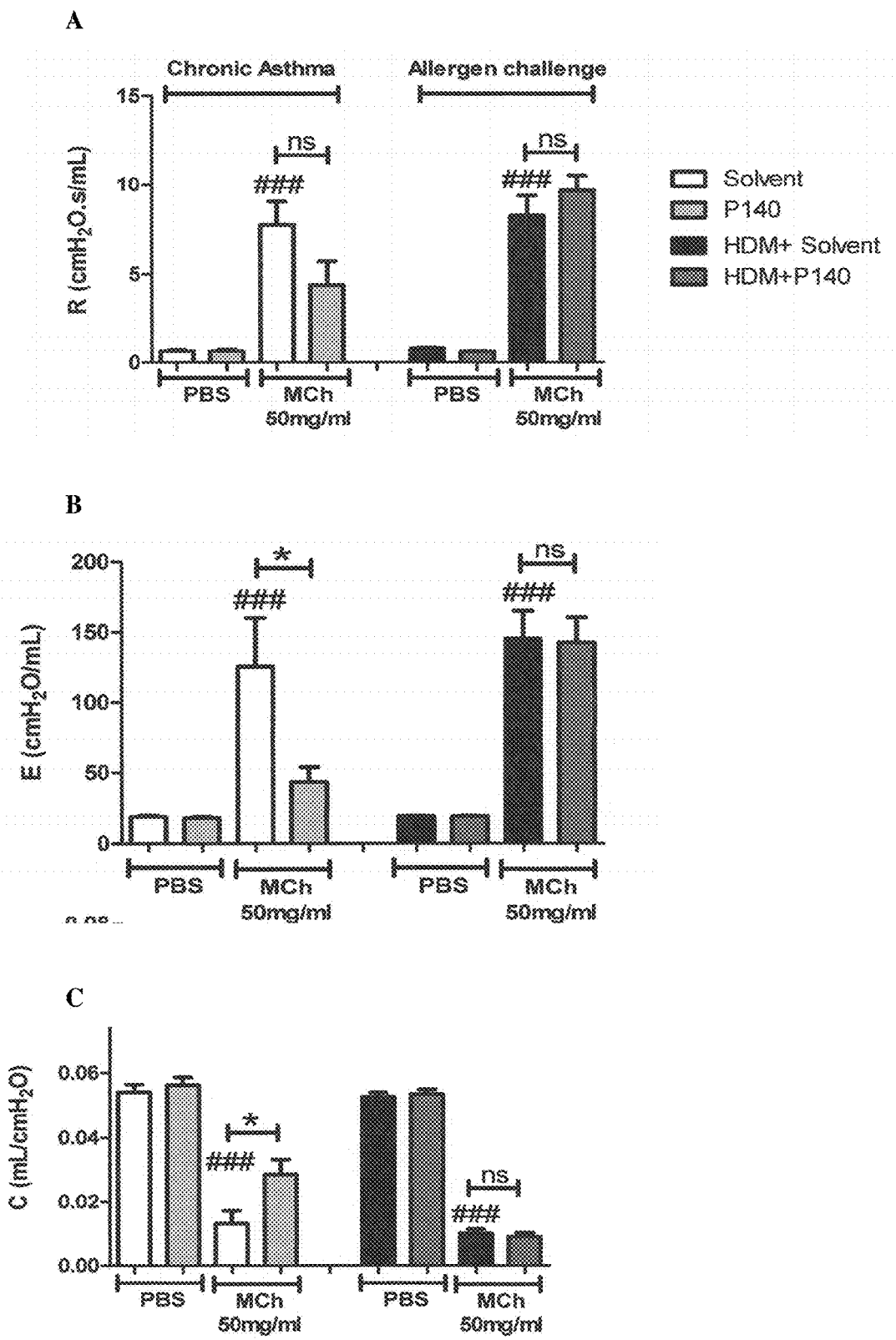
FIG. 15. Effect of the P140 phosphopeptide on airway reactivity in an HDM-induced asthma model in Balb/c mice. Airway resistance R expressed as cm $H_2O \cdot s \cdot mL^{-1}$, elastance E expressed as cm $H_2O \cdot mL^{-1}$ and compliance C expressed as $mL \cdot cm\ H_2^{-1}$ at baseline and in response to aerosolized PBS and MCh (50 mg/mL) was assessed with Flexivent®. Blocks are means and bars are SEM values (n=5 to 8 per group). ####p≤0.001 between PBS and MCh nebulisation, and *p≤0.05 between P140 and solvent groups in chronic asthma.

Inhalation of PBS had no effect on baseline airway resistance, elastance and compliance assessed by the Flexivent® technique in saline-challenged, solvent-treated mice (FIG. 15A-C). Treatment with P140 (i.v., 4 mg/kg, day 25) also had no effect on any parameter as compared to solvent-treated mice (FIG. 15A-C). However, inhalation of methacholine (50 mg/ml) induced a marked increase in airway resistance and elastance accompanied with a decrease in compliance (FIGS. 15A, B and C, respectively) in saline-challenged, solvent-treated mice. Treatment with P140 significantly decreased elastance (−65%, *p<0.05) and increased airway compliance (+115%, *p<0.05) as compared to the solvent group (FIG. 15), as well as decreased airway resistance (−42%) although non-significantly (n=5).

Airway Responses in Mice Challenged with Allergen (HDM)

Inhalation of PBS had no effect on baseline airway resistance, elastance and compliance in HDM-challenged solvent-treated mice. Treatment with P140 had no effect on airway resistance, elastance or compliance in allergen-challenged mice as compared to the solvent group. However, inhalation of methacholine induced significant increases in airway resistance and elastance accompanied with a decrease in compliance in HDM-challenged, solvent-treated mice (FIG. 15).

Effect in Chronic Asthma (HDM-Sensitized, Saline-Challenged Mice)

Figure 16:
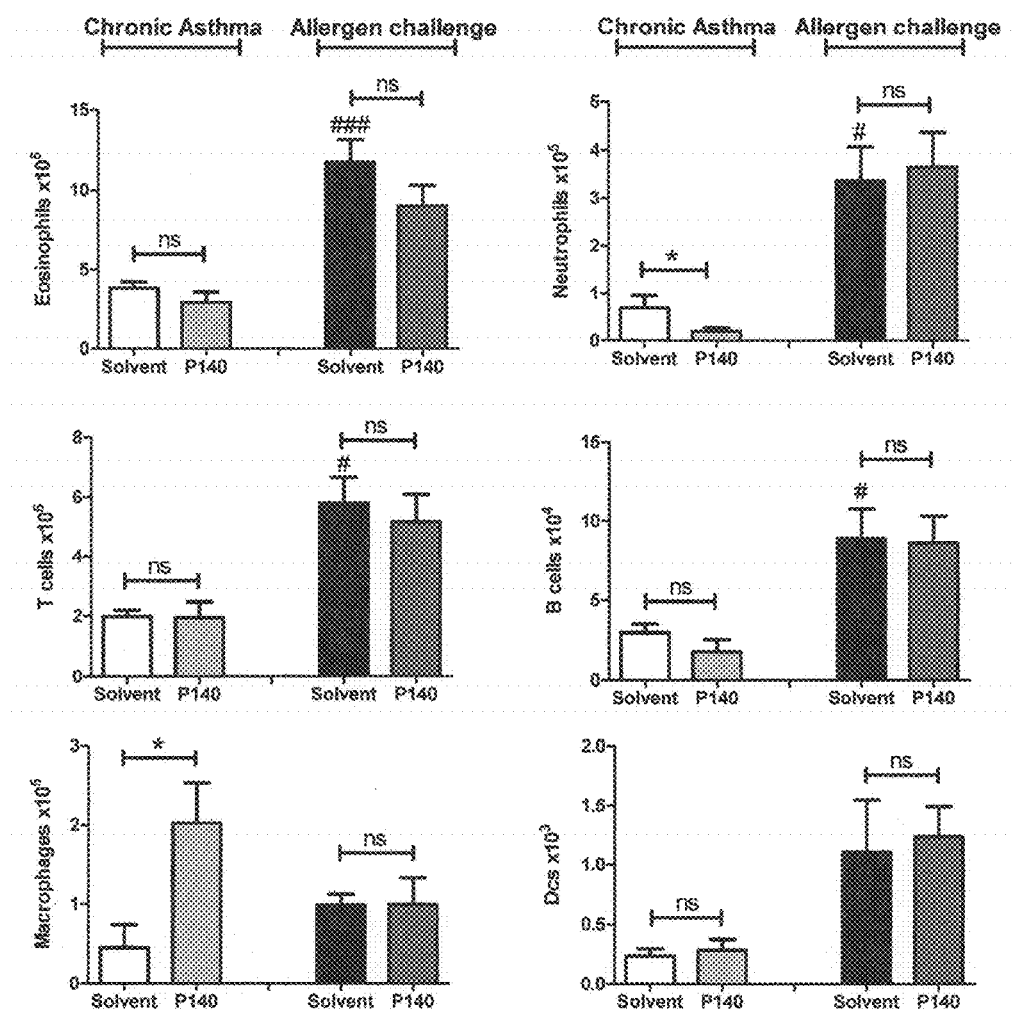
FIG. 16. Effect of the P140 phosphopeptide on airway inflammatory cell recruitment in an HDM-induced asthma model in Balb/c mice. Balb/c mice were sensitized by intranasal (i.n.) administration of HDM (Stallergenes): 1 µg in 25 µl PBS on day 0, 1, 2, 3, 4, and 10 µg on day 14 and 21. Mice were challenged by i.n. administration of HDM and/or PBS on day 28, 29 and 30. Mice were treated by i.v. injection (2 ml/kg) of P140 at the dose of 4 mg/kg or solvent on day 25. Absolute numbers of eosinophils, neutrophils, T cells, B cells, macrophages and DCs in BAL are shown. Blocks are means and bars are SEM values (n=5 to 8 per group). #p≤0.05 and ####p≤0.001 between solvent group in chronic asthma and allergen challenge, and *p≤0.05 between P140 and solvent groups in chronic asthma.

Eosinophils ($3.8 \times 10^5$), neutrophils ($0.7 \times 10^5$), macrophages ($0.4 \times 10^5$), T and B lymphocytes ($1.9 \times 10^5$ and $0.3 \times 10^5$), and dendritic cells ($0.2 \times 10^3$) were recovered in BAL fluid upon saline challenge in solvent-treated mice (FIG. 16). Treatment with P140 (4 mg/kg i.v., day 25) significantly decreased the number of neutrophils (−71%, *p<0.05), as well as eosinophils (−25%) and B cells (−40%) although non-significantly, and significantly increased the number of macrophages by 4.5-fold (*p<0.05) as compared to the solvent group (FIG. 16).

Effect in Mice Challenged with Allergen (HDM-Sensitized and HDM-Challenged)

Figure 2:
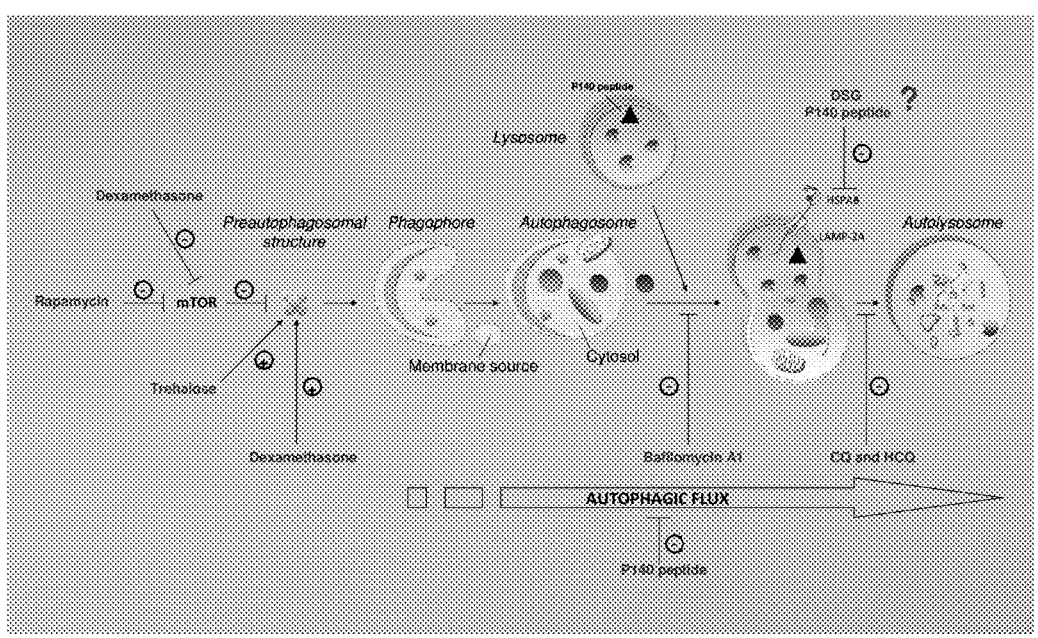
FIG. 2. Pharmacological regulators of autophagy. A diagram illustrating possible sites of intervention of pharmacological autophagy regulators. From the left to the right: rapamycin and dexamethasone inhibit the kinase activity of mTOR, leading to the upregulation of macroautophagy. Dexamethasone is also known as acting on pre-autophagosomal structure. Trehalose, the target of which still remains debated, is an activator of autophagy through an mTOR-independent pathway. Bafilomycin A1 prevents maturation of autophagic vacuoles by inhibiting fusion between autophagosomes and lysosomes. It acts by inhibiting vacuolar H+ ATPase. P140 peptide (▲), the uptake into B lymphocytes by clathrin-mediated endocytosis and homing into lysosomes has been demonstrated after administration to mice, and DSG, both interact with HSPA8 in vitro and alter intralysosomal pH. P140 provokes the accumulation of autophagy markers p62/sequestosome 1 and MAP1LC3-II in MRL/lpr B cells, consistent with a down-regulation of autophagic flux. This peptide affects both CMA and macroautophagy. CQ and HCQ are lysosomotropic agents that prevent endosomal acidification. They accumulate inside endosomes and lysosomes, leading to inhibition of lysosomal enzymes, which requires an acidic pH, defective fusion of endosomes and lysosomes and maturation of autolysosomes. Abbreviations: CMA, chaperone-mediated autophagy; CQ, chloroquine; DSG, 15-deoxyspergualin; HCQ, hydroxychloroquine; HSPA8, heat shock protein 8; LAMP-2A, lysosome-associated membrane protein-2A; MAP1LC3, microtubule-associated protein light chain 3; mTOR, mammalian target of rapamycin.

The number of inflammatory cells recovered in BAL fluid in HDM-challenged mice significantly increased as compared to chronic asthma (saline-challenged) (FIG. 2). This effect was related to a significant increased influx of eosinophils ($11.7 \times 10^5$, ###p<0.001), neutrophils (3.4, #p<0.05), T and B cells ($5.8 \times 10^5$ and $0.9 \times 10^5$, #p<0.05) (FIG. 16) in response to HDM challenge. Thus, treatment with P140 showed no effect on the inflammatory cell recruitment in BAL in HDM-challenged mice in comparison to the solvent group.

The aim of this study was to evaluate whether the P140 phosphopeptide could have an antiasthmatic effect when administered systemically in a 31-day asthma model in Balb/c mice sensitized to house dust mite (HDM) extracts. P140 was administered i.v. in HDM-sensitized mice, 2 days before HDM or saline challenge, i.e. 6 days before assessment of airway responses to MCh and of airway inflammatory cell recovery in the bronchoalveolar lavage.

We chose to design the study as sensitizing all animals to HDM as i) a model of chronic asthma when animals were further challenged with saline (HDM-sensitized, saline-challenged mice), and ii) a model of allergen challenge-induced asthma attack, when animals were further challenged with HDM (HDM-sensitized, HDM-challenged mice). In that, the protocol design could show the effect of P140 i) in every day chronic asthma, as well as ii) during asthma crisis.

In mice with chronic asthma (HDM-sensitized and saline-challenged) Methacholine induced a large increase in airway obstruction measured as increases in airway resistance (R) and elastance (E), accompanied by a decrease in airway compliance (C). As compared to the normal values we use to observe for control, unsensitized and non-challenged Balb/c mice (baseline R, E and C), these values are representative of the presence of airway hyperresponsiveness in these mice with chronic asthma. We show that P140 treatment significantly decreased airway responses to MCh with significant decrease in airway elastance E and increase in compliance C, as well as decrease in airway resistance R although non-significant as compared to the solvent-treated group. This suggests P140 decreases airway hyperresponsiveness observed in our allergic chronic asthma model.

In addition, we observe in this study the effect of P140 treatment on the inflammatory reaction existing in the airways in chronic asthma. Our model of chronic asthma is characterized by infiltration of eosinophils, neutrophils, macrophages, dendritic cells, T and B cells. P140 treatment induced a significant decrease in the number of neutrophils recovered in the bronchoalveolar lavage, as well as of eosinophils and B cells although non-significantly, and a significant increase in macrophages, as compared to solvent-treated mice. Asthma is known as an eosinophilic inflammation of the airways. More importantly, difficult uncontrolled asthma is described as an airway inflammatory disease with a change in the infiltrated inflammatory cell phenotype, most importantly with neutrophils infiltrating the airways. This phenotype is often resistant to glucocorticoid treatment. Therefore, the effect observed with the P140 phosphopeptide suggests that P140 has an antiasthmatic potential in chronic asthma, on airway hyperresponsiveness as well as airway inflammation.

Without being bound by any particular theory, P140 appears to be enhancing the resolution of chronic inflammation, in particular for neutrophils, existing in the airways in asthma, accompanied with resolution of airway hyperresponsiveness, which is one of the most invalidating symptom in asthma patients. In mice challenged with allergen (HDM-sensitized and HDM-challenged) HDM induced further increase in airway hyperresponsiveness and airway inflammatory cell infiltrate recovered in BAL. However, P140 treatment had little effect on this allergen-challenge-induced increased airway hyperresponsiveness to MCh nor inflammatory cell recruitment in BAL. This indicates that P140 treatment, when administered 2 days before allergen challenge is not as potent for blocking the reaction of an asthma crisis, although the basal levels of asthmatic airway responsiveness and inflammation in the absence of HDM challenge were reduced.

Systemic administration of P140 (4 mg/kg i.v.), 2 days before saline challenge, has the potential to restore baseline airway responsiveness, and resolve inflammation in every day chronic asthma. By contrast, in the conditions used for P140 administration, i.e. 2 days before the HDM challenge, P140 had no effect on the consequences of allergen challenge, indicating it does not improve nor worsen the effect of allergen in the sensitized airways. Such activity of P140 measured in the 31-day model of asthma indicates that P140 could be effective in chronic asthma. Increasing delay between P140 treatment(s) and allergen challenge might allow increased activity of P140 in asthma. We anticipate P140 may prevent airway hyperresponsiveness as well as airway inflammation caused by repeated allergen contact, i.e. resolve symptoms of every day chronic asthma.

Example 10. Effect of p140 Peptide on a Rat Model for Chronic Inflammatory Demyelinating Polyradiculoneuropathy Chronic inflammatory demyelinating polyradiculoneuropathy (CIDP) is an autoimmune-mediated inflammatory disease of the peripheral nervous system (PNS) for which therapies are limited/lacking. Recently, a new animal model for CIDP, the chronic-EAN, has been characterized (Brun S, Beaino W, Kremer L, Taleb O, Mensah—Nyagan A G, Lam C D, Greer J M, De Seze J, and Trifilieff T (2015). Characterizaton a new rat model for chronic inflammatory demyelinating polyradiculoneuropathies. *J. Neuroimmunol.* 278: 1-10). This model fulfills electrophysiological criteria of demyelination with axonal degeneration, confirmed by immunohistopathology. The late phase of the chronic disease was characterized by accumulation of IL-17 cytokine-positive cells and macrophages in sciatic nerves, and by high serum IL-17 levels. It is a reliable and reproducible animal model for CIDP, which can be used for translational drug studies for chronic human autoimmune-mediated inflammatory diseases of the PNS, and particularly CIDP, for which, there is a crucial need for new targeted immunotherapies. Thus, this study sought to investigate the possible effect of P140 peptide in this new preclinical rat model for CIDP.

Male Lewis rats, 7-8 weeks old, weighing 250-270 g, purchased from Charles River (Domaine des Oncins, L'Arbresle, France) were used. To induce chronic-EAN (CIDP), rats were immunized with S-palm-P0(180-199) peptide by subcutaneous injection at the base of the tail of 200 µL of an inoculum containing 200 µg of peptide (Ac(palm)KRGRQTPVLYAMLDHSRS), and 0.5 mg of *Mycobacterium tuberculosis* (strain H37 RA, Difco, Detroit, Mich., USA) emulsified in 100 µL of saline solution and 100 µL of Freund's incomplete adjuvant (SIGMA-Aldrich, St-Quentin Fallavier, France).

Body weight and clinical scores are assessed daily until 60 days post-immunization (dpi). Severity of paresis is graded as follows: 0=no illness; 1=flaccid tail; 2=moderate paraparesis; 3=severe paraparesis; 4=tetraparesis; 5=death.

A total of 15 rats were used and treated as indicated in the following table:

TABLE 10

| Number of rats | Emulsion injected at day 0 | Denomination | Treatment |
| --- | --- | --- | --- |
| 4 | S-palm P0(180-199) + CFA | control CIDP | — |
| 7 | S-palm P0(180-199) + CFA | treated CIDP | P140 |

100 µg/rat P140 peptide in 500 µL water/saline (1:10) were intraperitoneally injected at 5, 7, 9, 13 dpi and 3 times per week from 22 dpi until the end of the study.

a) Cytokine ELISA

Sera from treated and non-treated rats will be collected at 18, 40 and 60 dpi. The concentration of IL-17 cytokine will be measured in duplicate in undiluted sera using commercial ELISA kits specific for rat IL-17 (eBioscience, San Diego, Calif., USA), as per the manufacturers' instructions.

b) Antibody ELISA

Sera from treated and non-treated rats will also be tested at 18, 40 and 60 dpi for the presence of anti-PO(180-199) antibodies using ELISA. Peptide will be coated onto 96-well plates at 20 µg/mL in 0.05 M carbonate-bicarbonate buffer solution (pH 9.6, 100 µL/well) and incubated overnight at 4° C. Plates will be then washed with phosphate-buffered saline (PBS) and blocked with 1% bovine serum albumin in PBS for 1 h at 37° C. After washing, sera (100 µL/well) diluted at ⅕₀₀₀ will be added in duplicate and incubated for 2 h at 37° C. After washing, plates will be incubated with goat anti-rat IgG coupled to peroxidase (1:2000, SIGMA-Aldrich) for 2 h at 37° C. After extensive washing, each well will be incubated with 75 µL of TMB at room temperature until color development. The reaction will be stopped by addition of 1 M $H_2SO_4$ (25 µL/well).

c) Immunohistochemistry

To evaluate inflammatory cell infiltration and pathological changes in the PNS, treated and non-treated rats will be sacrificed at 60 dpi. Rats will be deeply anesthetized with Ketamine/Rompun and perfused intracardially with 4° C., 4% (v/v) paraformaldehyde (PFA) in PBS. Sciatic nerves and cauda equina will be dissected out, fixed in Bouin and embedded in paraffin.

After dewaxing, cross-sections (5 μm) will be heated at 80° C. for 10 min in citrate buffer. Endogenous peroxidase will be inhibited with 0.02% $H_2O_2$ in water for 10 min. Non-specific binding sites will be blocked with 5% fetal calf serum (Gibco Invitrogen, Camarillo, Calif., USA) in PBS for 30 min and then with the following monoclonal antibodies: anti-MBP (1:500; produced in house) for myelin; SMI-311 (1:1000; Abcam, Paris, France) for neurofilaments; ED1 (1:400; Serotec, Oxford, UK) for macrophages and anti-interleukin-17 (IL-17; 1:100; Santa Cruz Biotechnology, Santa Cruz, Calif., USA). Antibody binding to tissue sections will be visualized with biotinylated anti-mouse IgG (1:200; Vectastain®, Vector Laboratories, Burlingame, Calif., USA) and Avidin-Biotin-complex (ABC-peroxidase kit; Vectastain®, Vector Laboratories), followed by development with DAB substrate (Vector® DAB SK-4100, Vector Laboratories) for IL-17, and VIP substrate (Vector® VIP SK-4600, Vector Laboratories) for other antibodies.

Figure 17:
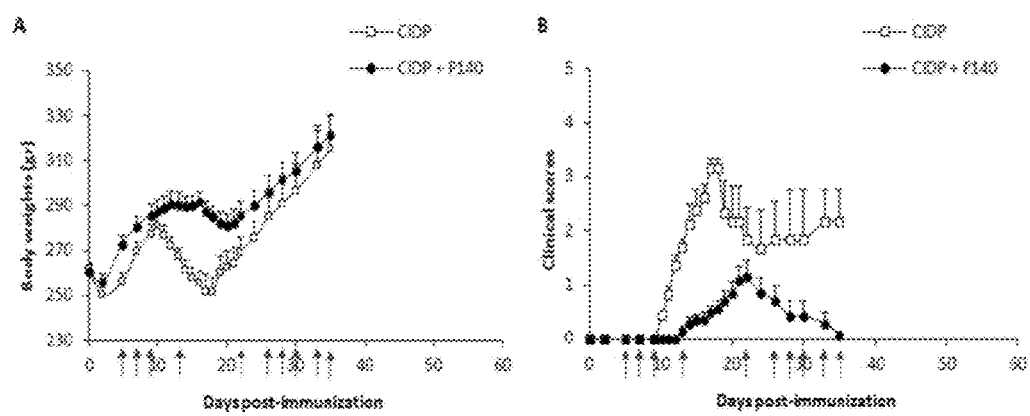
FIG. 17. Body weight (A) and clinical course (B) of CIDP rats treated with P140 peptide (●) compared to untreated rats (□). Injection of P140 peptide is represented by red arrows. Mean values and SEM are indicated.

P140 peptide exhibits an effect on the disease severity in CIDP rats and abolishes the chronicity. To examine the effect of P140 peptide on CIDP rats, animals are treated with P140 (100 μg/rat) intraperitoneally at 5, 7, 9, 13 dpi and 3 times per week from 22 dpi until the end of the study. FIG. 17A shows the evolution of weight during the disease course with a maximal weight loss that corresponds to the maximal of clinical scores of the disease. This weight loss is less important in the treated group compared to untreated rats. As shown in FIG. 17B, treatment of P140 not only delayed the onset of the disease and decreased the maximal clinical scores compared to untreated rats but also seems abolish the chronicity of the disease.

Example 11. Study of the P140 Peptide Effect in a Murine Model of Gougerot-Sjögren Syndrome, the MRL/Lpr Mouse (Focus on Salivary Glands)

In this study MRL/lpr female 11-12 week old mice were used with 10 mice per group for statistical analysis. Each mouse received a single injection by retro-orbital, 100 μg of peptide P140 of 100 μl in 9% NaCl. After 5 days, the mouse blood was collected in heparinized tube and salivary glands (GSS) were removed and placed in Eppendorf tubes containing PBS pH 7.4.

The Effects of Peptide P140 have been Studied in Several Systems

Study of cellularity in peripheral blood: 300 μl mouse blood is lysed in of 3 ml DAKO EasyLyse (ref 52364) according to the protocol provided by the Supplier (Procedure B). After two washes in PBS pH 7.4-2% (v/v) fetal calf serum, the cells are taken up in 300 μL of the same buffer. The cells are then counted on Malassez cell in the presence of Turkish Blue to differentiate the leukocytes remaining red blood cells. We infer a number of cells per ml of blood to be compared between different treatment groups to see if the P140 peptide induces a variation in the amount of leukocytes in the blood.

Preparation Organs Cryostat

Salivary glands (SGs) are washed in PBS pH 7.4 and then placed in a cup dedicated to the preparation of cryostat sections. The cup is filled with "OCT" medium (Cell path, ref. 03803126) until the tissue is completely covered. The cup is then immersed in liquid nitrogen and then stored at −80° C. until use.

The tissue was cut by cryostat sections of 5 microns. Sections were left at room temperature overnight (12 hours). The next day the sections were incubated in 100% acetone for 30 minutes. The sections can then be stored at −80° C. for later use. The sections are then rehydrated in PBS pH 7.4, five minutes before immunostaining.

Immuno Staining:

The protocol is as follows:

Incubate sections in PBS-2% (w/v) BSA for 30 minutes

Wash Twice 5 minutes with the cuts PBS pH 7.4

Dilute the antibody of interest, typically at ½00 in PBS-2% BSA and incubated directly on the sections for 2 hours at room temperature (or overnight at 4° C.)

Wash Three times 10 minutes with PBS pH 7.4

Perform nuclear staining with DAPI diluted 1/5000 in PBS for 15 minutes

Wash Three times 10 minutes with PBS pH 7.4

Set sections with paraformaldehyde (PFA) 4% (v/v) for 20 minutes.

Remove excess PFA then mount the cover slip on the slide with the "DAKO mounting medium" and let dry for 2 hours at room temperature, protected from light.

Visualize with microscope.

Marking hematoxylin/eo sin:

The number of foci site (FS) is determined for each mouse. A focus is defined as an aggregate of 50 or more cells.

The level of inflammation SG is determined semiquantitatively by a scoring system (0-3 scale): Grade 0: no inflammatory cells; Grade 1: few perivascular inflammatory and periductal Infiltrates (<100 cells); Grade 2: moderate number of perivascular inflammatory and periductal Infiltrates (100-500 cells); Grade 3: extensive inflammation with inflammatory foci broad (>500 cells).

Study of Salivary Glands by Flow Cytometry

Cells of total salivary glands stained with fluorescently were labeled antibodies for 40 min at 4° C., Were Collected data by FACSCalibur.

TABLE 11

| Antibodies | References |
| --- | --- |
| CD3-FITC | BD-553062 |
| CD4-FITC | BD-557307 |
| CD8-PercP cy5.5 | BD-551162 |
| CD19-PE | BD-553786 |
| CD45-APC | BD-559864 |
| CD45R (B220)-PercP | BD-553093 |
| TCR γσ-APC | eBioscience-17-5711 |
| TCR β-FITC | BD-553170 |

The results of the study of cellularity in the peripheral blood is provided.

The weight of salivary glands Was Measured after-excision. DNase I (1 mg/ml) and collagenase D (50 μg/ml) were used to digest the salivary glands. Total cell counts were evaluated after the digestion.

Figure 18:
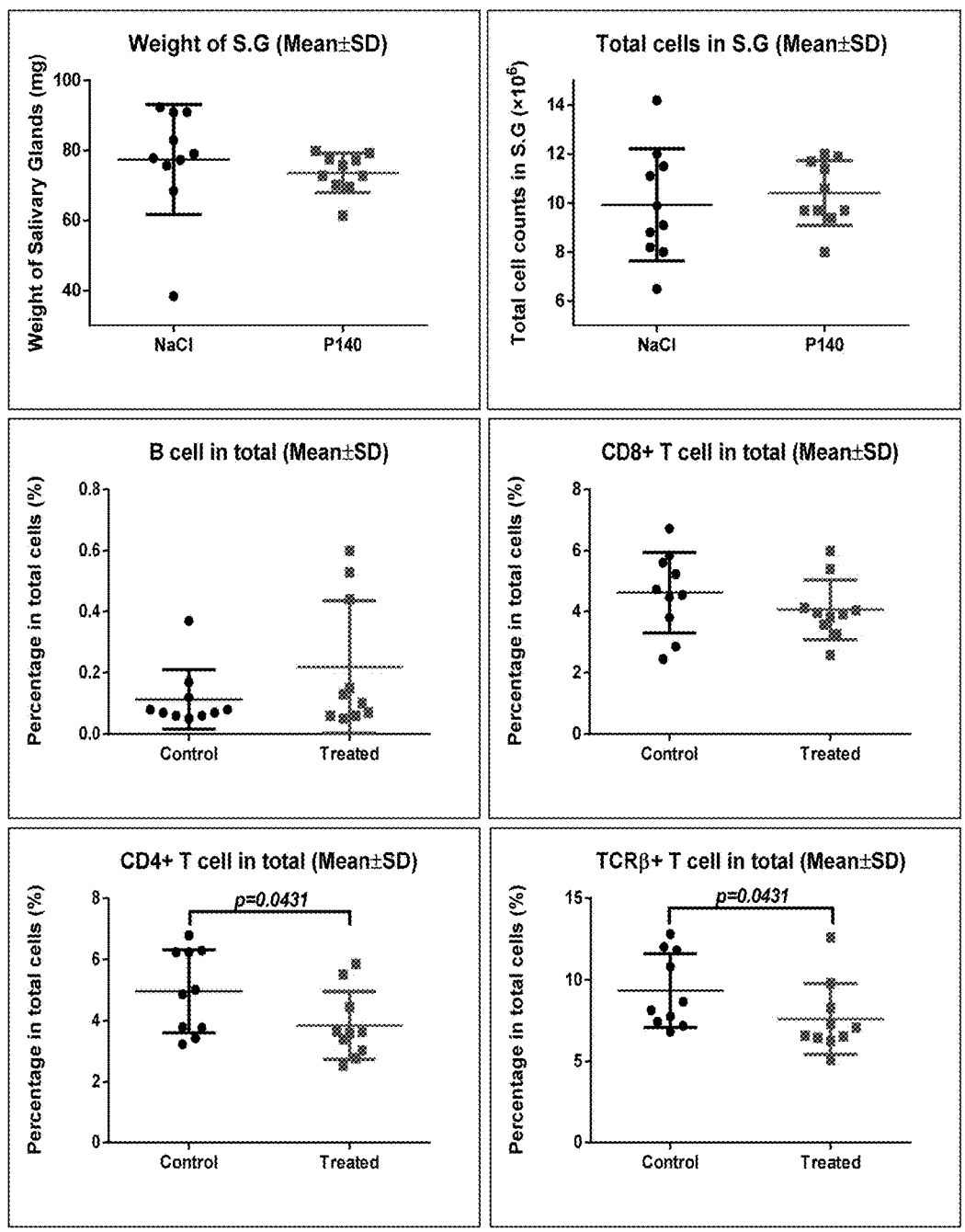
FIG. 18. Evaluation of lymphocyte subpopulations in isolated salivary glands.

In this experiment the mice were evaluated 5 days post-administration (one single iv injection), P140 peptide had no statistically significant effect on the weight of SGs (FIG. 18).

Study of Salivary Glands by Flow Cytometry

P140 treatment (5 days; one single iv injection) had no apparent effect on the total number of cells present in the SGs Treated of MRL/lpr mice (FIG. 18).

However, when lymphocyte subpopulations were examined, it was detected that the P140 peptide effect was specific to particular lymphocyte subsets. P140 decreased CD4+T cells (but not CD8+T cells) in SGs of MRL/lpr mice (FIG. 18). In preliminary experiments (not shown), we saw that CD4+T cells are the predominant cell subpopulation Infiltrated in SG. These T cells are largely β TCR+T cells. P140 peptide had no statistically significant effect on the total number of B cells.

Study of Salivary Glands in Microscopy

Figure 19:
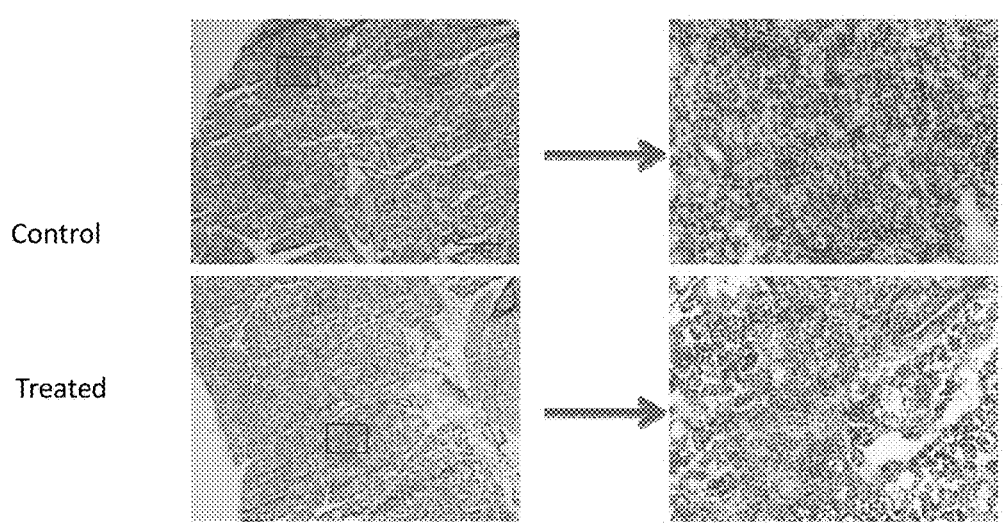
FIG. 19. Evaluation of the level of inflammation in isolated salivary glands.
Figure 20:
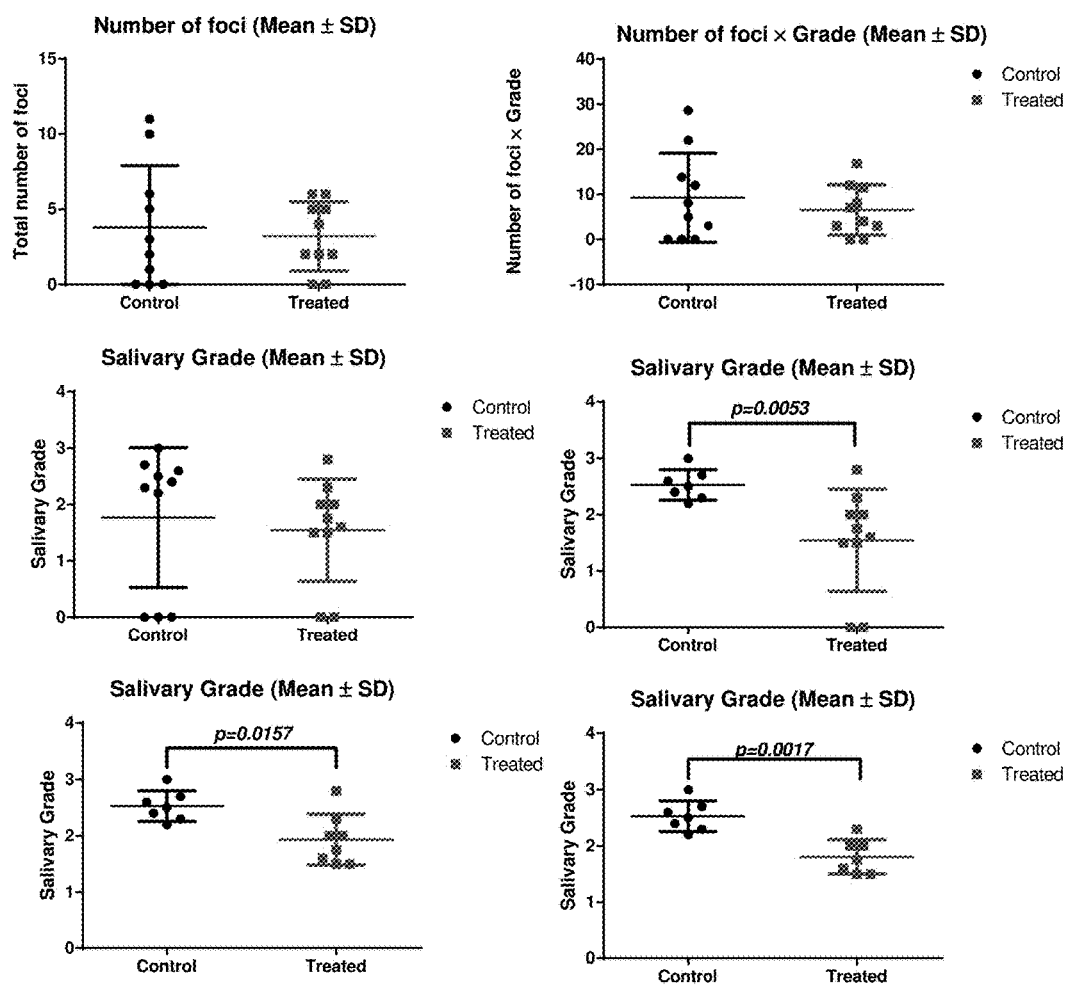
FIG. 20. Evaluation of the number of FS is isolated salivary glands.

The MRL/lpr mice (10 mice per arm) were injected with peptide P140 (100 µl/mouse iv). Five days after injection the mice were sacrificed and SGs collected as indicated above. The tissue was cut by the cryostat sections of 5 µm. The sections were labeled with hematoxylin/eosin staining is the method most frequently used in tissue histology. The level of inflammation and the number of FS were determined (FIGS. 19 and 20). Representative pictures are from sample control group 4 and group Treated sample (Bar 500 µm).

The results show that as soon as 5 days after one single administration of peptide P140, lymphocytic infiltration in the SGs of MRL/lpr mice was significantly reduced.

Example 12. Effect of the P140 Peptide in the Murine Model of Rheumatoid Arthritis Rheumatoid Arthritis (RA) is a chronic inflammatory disease that affects the articulations. The disease evolves by outbreaks of inflammation of varying duration and intensity. In particular, it causes joint swelling in the hands and wrists. Several animal models of RA, usually induced, are available. The following report describes the results obtained in an acute model of RA, namely the model K/BxN mouse. The potential effect of P140 in this mouse has been tested in a "curative" protocol and a "preventive" protocol.

The TCR transgenic mice expressing the KRN and the MHC class II $A^{g7}$ molecule (K/BxN mice) have developed a severe inflammatory arthritis. The administration of serum of these mice to healthy recipient mice causes inflammatory arthritis over a period of about 15 days with a peak ignition around day 7 post-injection.

Two mouse serum administrations from K/BxN were performed (day 0 and day 2). The injection of serum (100 µl/mouse) is performed by intra-peritoneal (ip) injection in mice C57BL/6 (or B6) for 8 weeks (n=10); untreated mouse (n=10).

Figure 21:
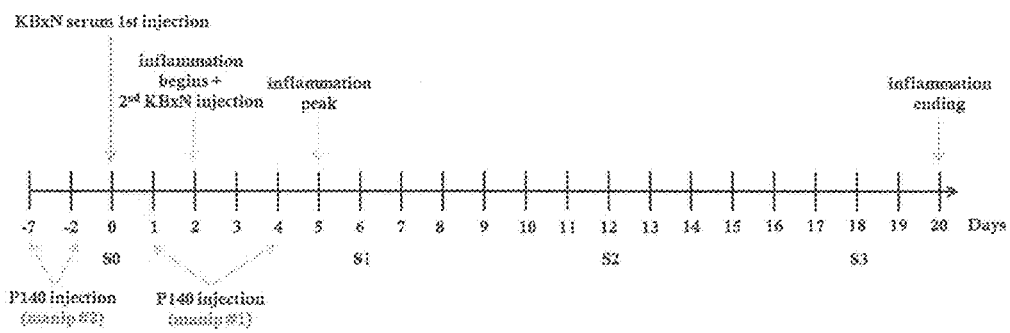
FIG. 21. Effect of the P140 peptide in the murine model of rheumatoid arthritis.

The P140 peptide (100 µg/100 µl; iv retro-orbital) was administered as follows:

Curative treatment: Injection at day 1 and day 4, to guide the peak of inflammatory disease. Preventive treatment: Injection at day −7 and day −2. Bleeding S0 (at day 0) is followed by bloodletting conducted every six days to dispose of serum. The study ends when inflammation has returned to its basal level, to around day 20 (see FIG. 21).

Figure 22:
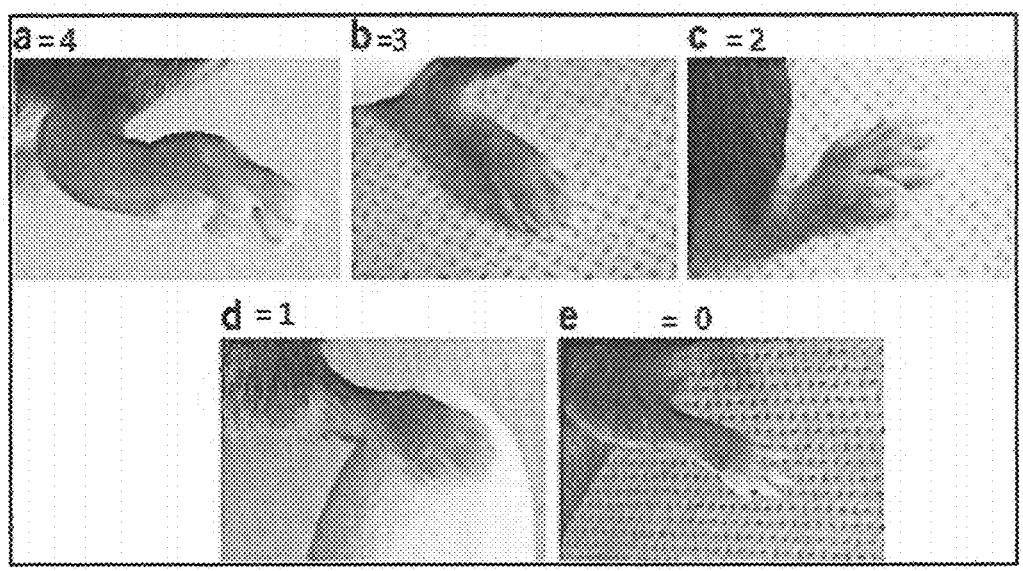
FIG. 22. Effect of the P140 peptide in the murine model of rheumatoid arthritis.

During the peak of inflammation, every day the animals are evaluated, and swelling score of articulation is established. It is ranged from 0 to 4 and based on a joint observation of the animal. In practice, this score is given for each leg (4 values) and these values are added together to get a general score that ranges from 0 to 16 (FIG. 22).

In this experiment, the induction of the disease has been suboptimal. We did not observe significant increase clinical signs of the disease.

Figure 23:
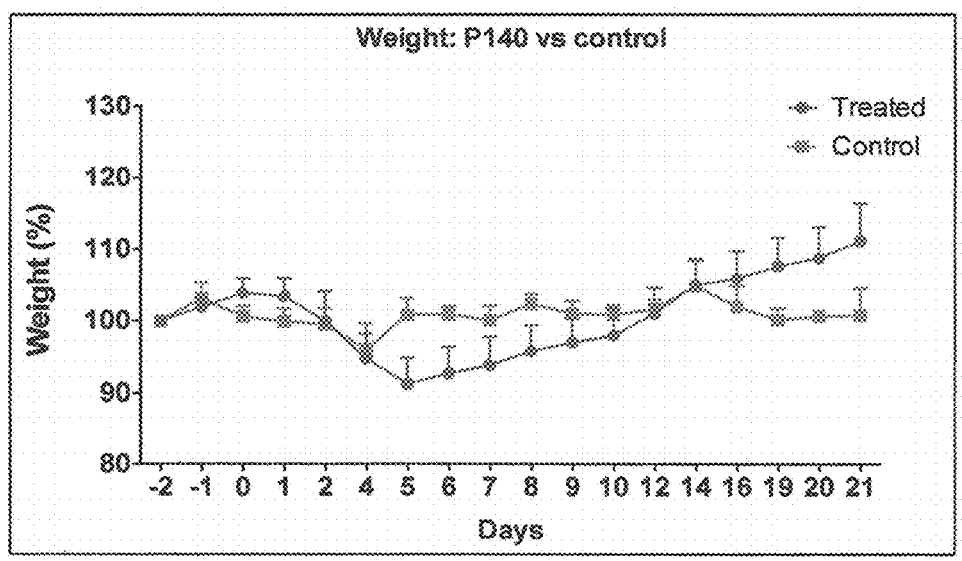
FIG. 23. Effect of the P140 peptide in the murine model of rheumatoid arthritis.

On day 2 (two days after the injection of K/BxN serum, and the day of the 2nd injection serum K/BxN), mice treated P140 NaCl begin to lose weight (15 and 10%). From day 5, the animals begin to regain weight: we notice a weight gain of 20% for P140 mice treated between day 5 and the end of the study while the mouse controls exceed 5% weight gain. The difference was statistically significant between these two curves (2 way ANOVA) (FIG. 23).

Evolution of the Size of the Legs of the Animals

Figure 24:
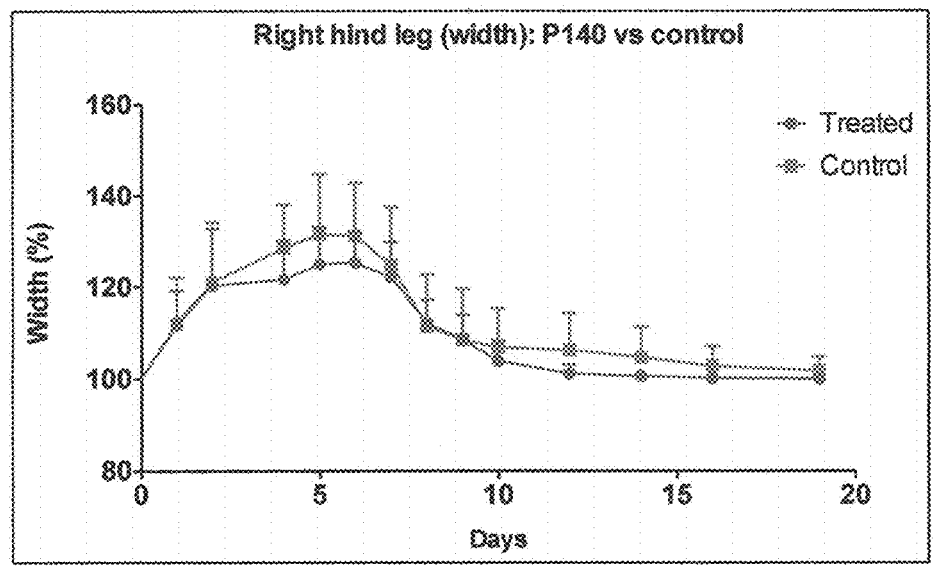
FIG. 24. Effect of the P140 peptide in the murine model of rheumatoid arthritis.

Right back legs: we see an increase in width of the rear leg from day 0 to day 6, with a maximum between days 5-6 of 30%. From day 6, this increase reverses and we see a return to normal around day 10. The difference was statistically significant between these two curves (2 way ANOVA) (FIG. 24).

Figure 25:
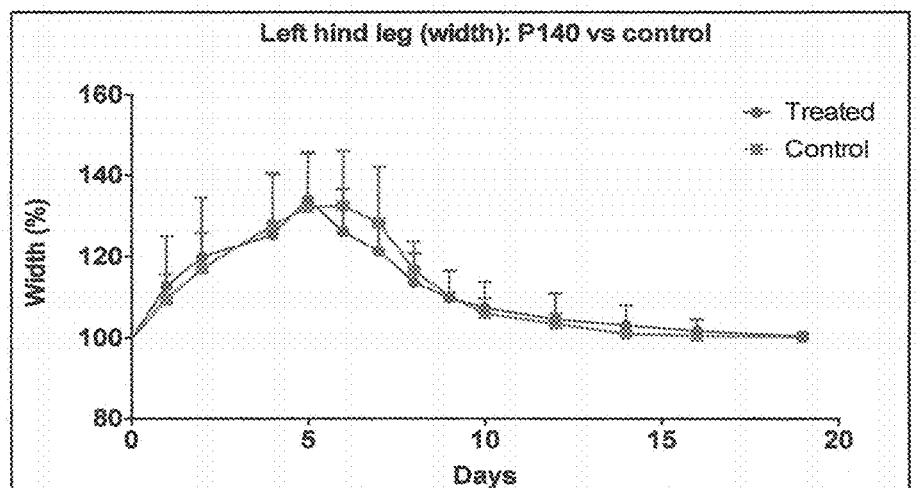
FIG. 25. Effect of the P140 peptide in the murine model of rheumatoid arthritis.

Left back legs: we observe an increase of about 30% of the leg width, with a peak around day 5-6, and then a return to normal gradually, from day 6. The difference was statistically significant between these two curves (2 way ANOVA) (FIG. 25).

Evolution of Inflammation Score

Figure 26:
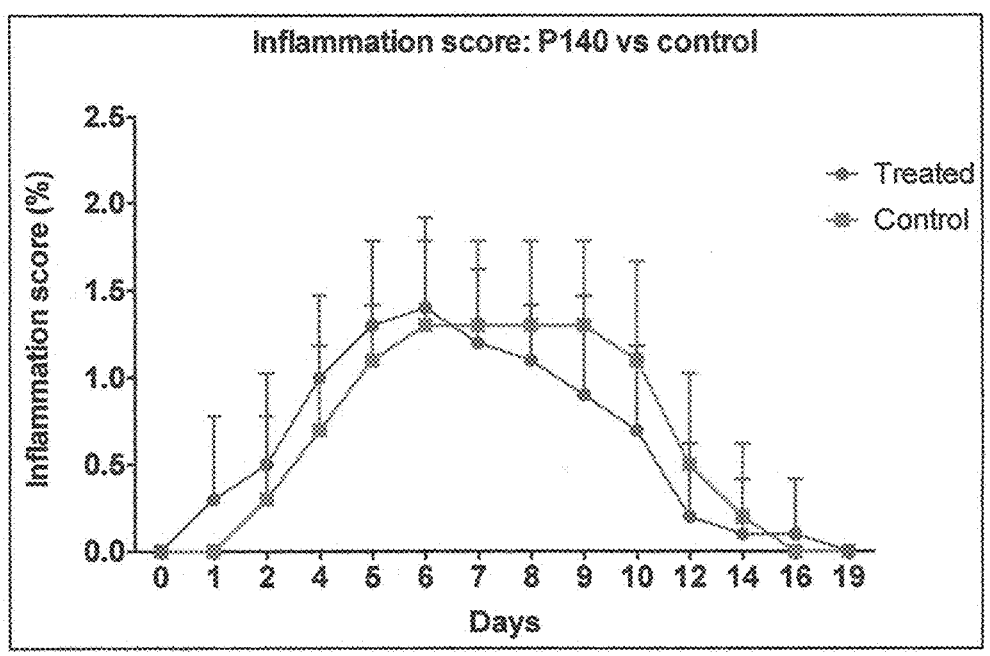
FIG. 26. Effect of the P140 peptide in the murine model of rheumatoid arthritis.

For this experiment, the inflammation scores were calculated independently, for each leg (rear legs left and right). The score exceeds only 1.5 for maximum either for P140 treated mice or mice controls.*For the treated mice the two curves do not show any statistically significant difference in two way ANOVA (FIG. 26).

The results obtained during this preliminary experience have enabled us to identify some important points that will be very useful for the design of the next experiments:

1) inflammation was very moderate (small increase in the size of legs, little weight loss, inflammation of very low scores). The mode of administration serum K/BxN will be changed from 100 µl of serum with 50 µl of vehicle (NaCl) to 100 µl without vehicle.

2) Only the two rear paws of the animal were examined. But ultimately, it was observed that the front legs are most affected by the disease. Next, the four legs of the animal will be taken into account for the measured height joints in foot slides.

3) In the next experiment, an animal's overall inflammation score will be calculated (adding the individual score of the four legs).

Preventive Protocol: Evolution of the Weight of the Animals

Figure 27:
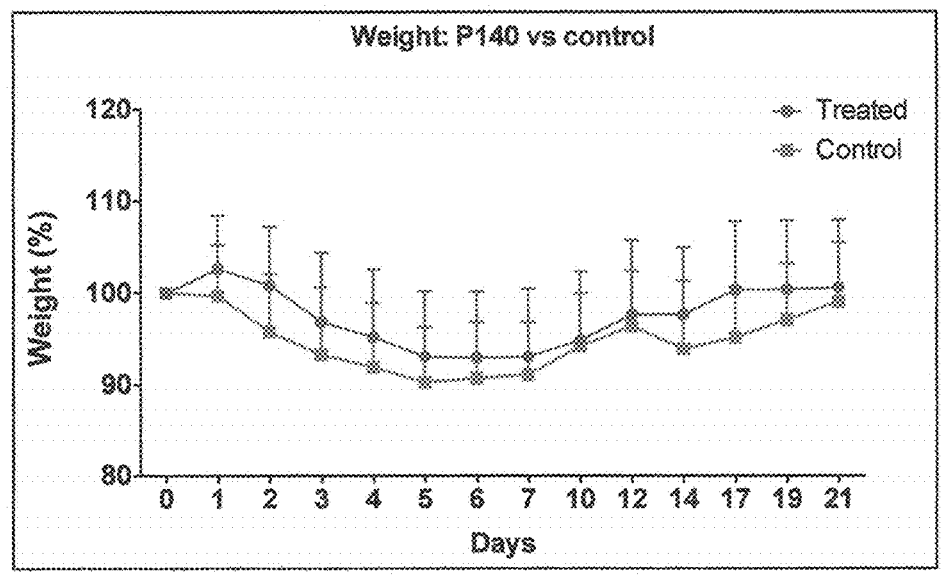
FIG. 27. Effect of the P140 peptide in the murine model of rheumatoid arthritis.

Analysis of the weight of the animals showed a loss of 5% weight-mice treated by the P140 and 10% for controls mouse. This weight loss occurs during the initiation phase (day 1 to day 7). We note a slightly faster return to original weight for mice treated mice compared to controls. However, it is no statistical difference significantly between the two curves (2 way ANOVA) (FIG. 27).

Evolution of the Size of the Legs of the Animals

Figure 28:
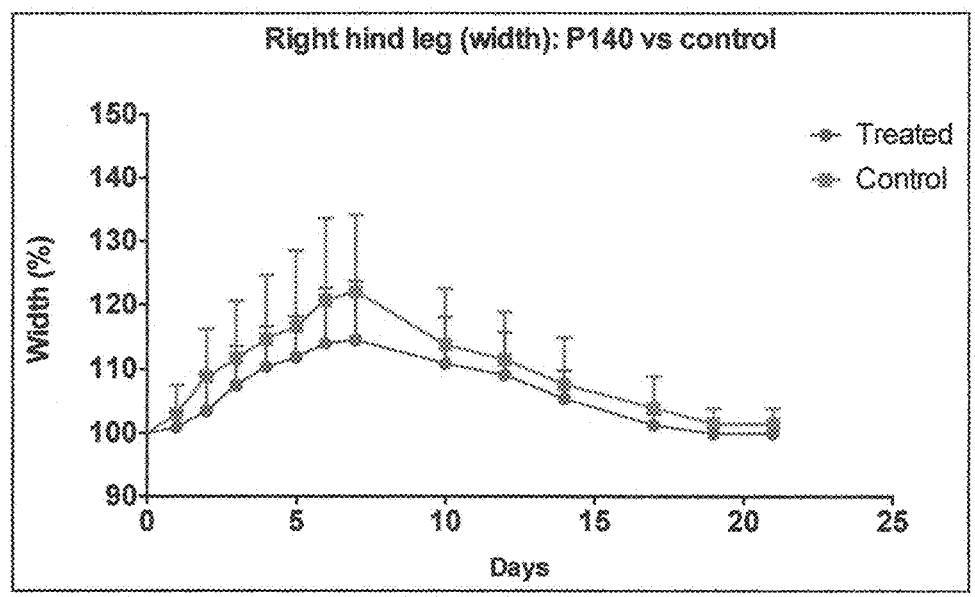
FIG. 28. Effect of the P140 peptide in the murine model of rheumatoid arthritis.

Right back legs: increasing the size of joints around 12% in treated mice and about 22% in control mice. This increase in size joints occurs between day 0 and day 7, before a return to normal gradually. We note a slight difference in the two curves, but without difference statistically significant (2-way ANOVA) (FIG. 28).

Figure 29:
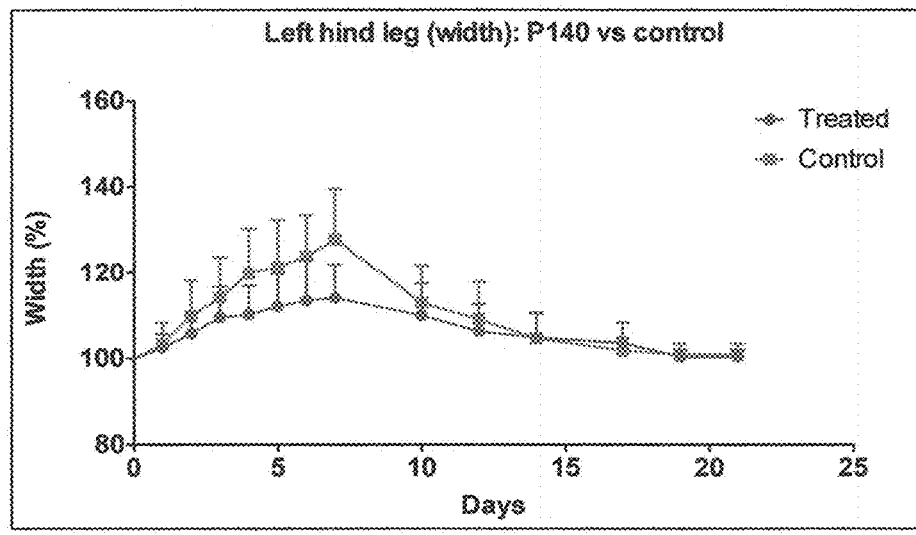
FIG. 29. Effect of the P140 peptide in the murine model of rheumatoid arthritis.

Left hind paws: increase in the size of the joint of about 15% in the treated mice and about 30% among controls mouse. This increase takes place between day 0 and day 7 then a return to normal is observed. We are seeing a lag of two curves, but with no statistical difference significance (2-way ANOVA) (FIG. 29).

Figure 30:
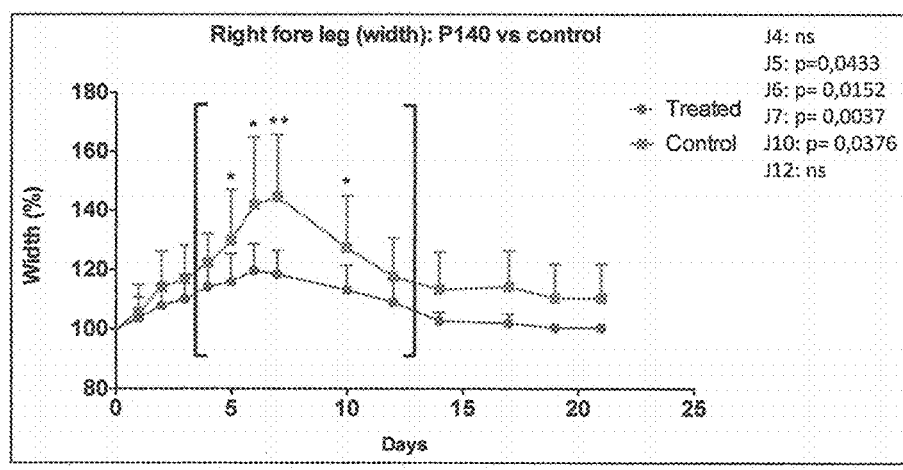
FIG. 30. Effect of the P140 peptide in the murine model of rheumatoid arthritis.

Right front legs: as with the rear legs, inflammation occurs between day 0 and day 7 and returns to the normal after day 7 with the treated mice showing moderate swelling in the joints of right front leg (+20%) while the mouse controls undergo an increase of nearly 45%. The difference between the two curves is statistically significant in two way ANOVA (p=0.0069; **) (FIG. 30).

Figure 33:
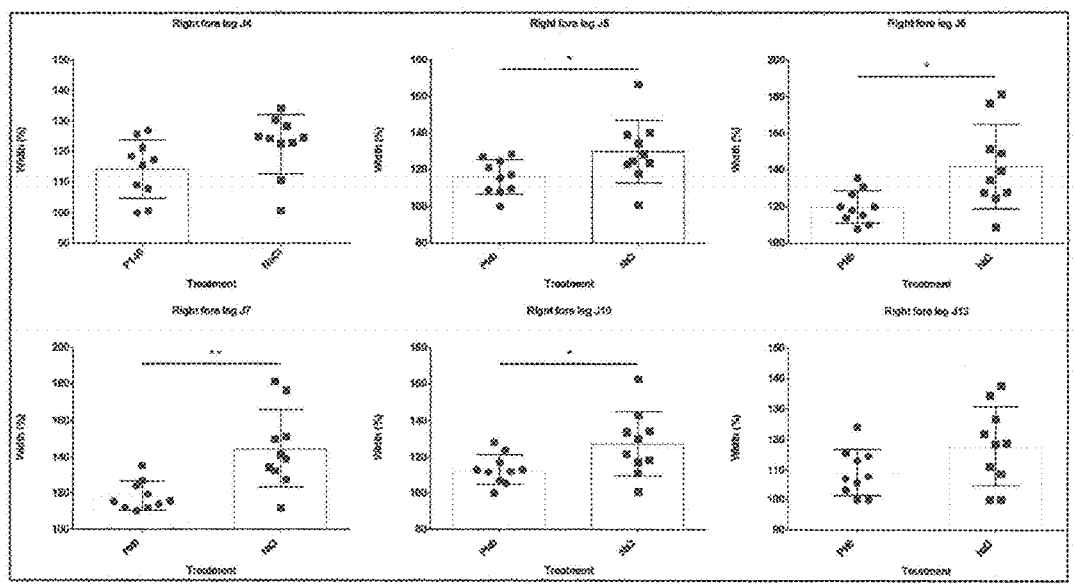
FIG. 33. Evolution of the size of the front straight panes daily, P140 vs NaCl (unpaired T test)

If one compares not the entirety of the curves between them but day by day (unpaired t test) by framing the peak of ignition (between day 4 and day 12; FIG. 30 and FIG. 33), we observe that a maximum of inflammation (day 7), the controls are more affected by the disease than mice treated: p=0.0037; **.

Figure 31:
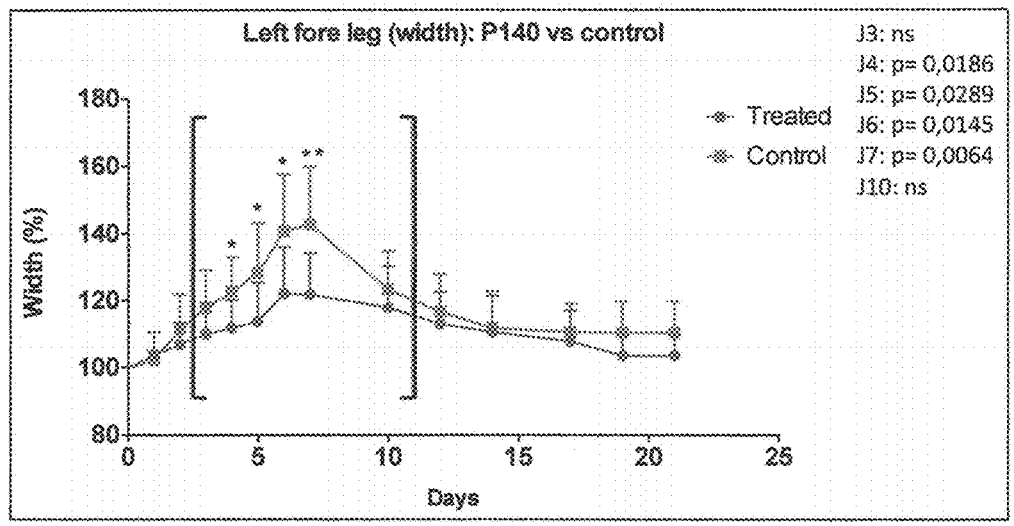
FIG. 31. Effect of the P140 peptide in the murine model of rheumatoid arthritis.

Left front leg: the treated mice showed an increase in the size of their 20% articulation d'- and mouse controls '–' 45%. The difference between the two curves is statistically significant (two way ANOVA-P=0.0397; *) (FIG. 31). We also realized a framework of inflammation from the curves of the growth of the size of the joints of the left front legs. Compared to the previous curve (FIG. 30), it is between about day 3 and day 10.

Figure 34:
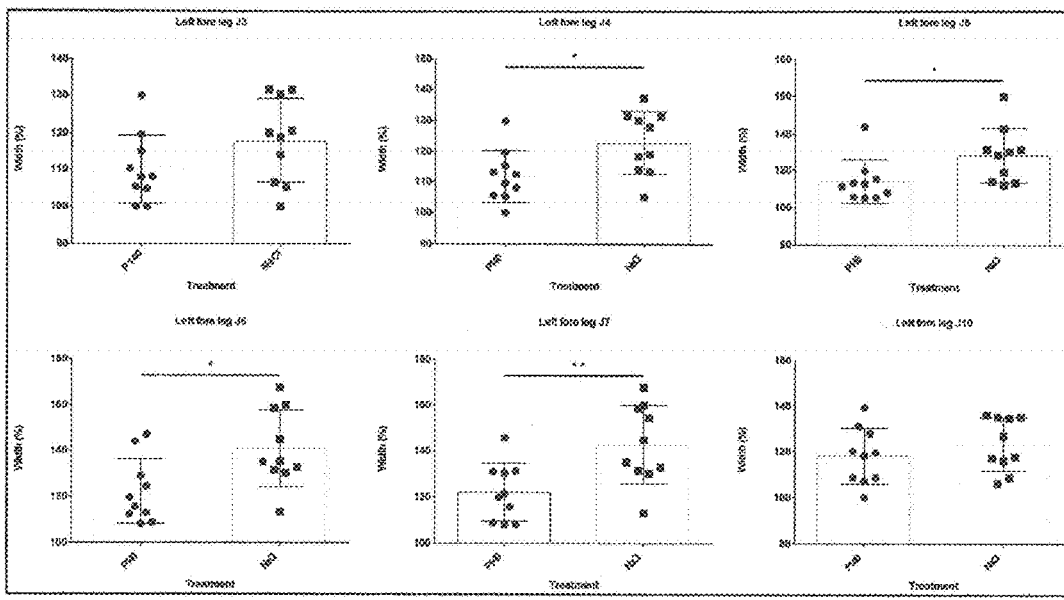
FIG. 34. Evolution of the size of the left front legs daily, P140 vs NaCl (unpaired T test)

We note that at peak inflammation (day 7), the controls are more mice affected by clinical signs of disease than mice treated: p=0.0064; **. The representation above (FIG. 31 and FIG. 34) compares daily the growth in the size of the left front legs of mice treated mice compared to controls (Unpaired t test).

Evolution of Inflammation Score

Figure 32:
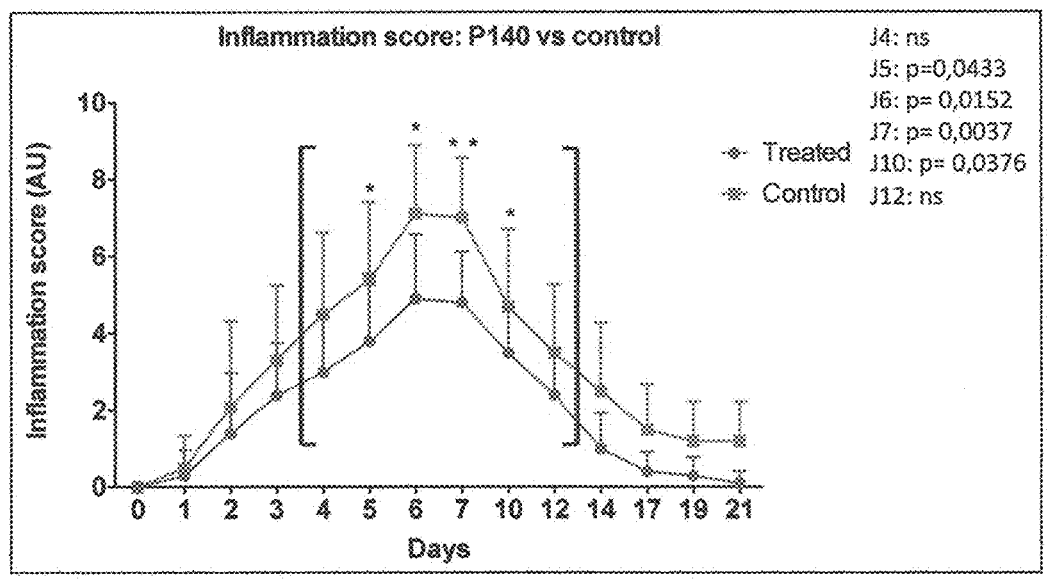
FIG. 32. Effect of the P140 peptide in the murine model of rheumatoid arthritis.
Figure 35:
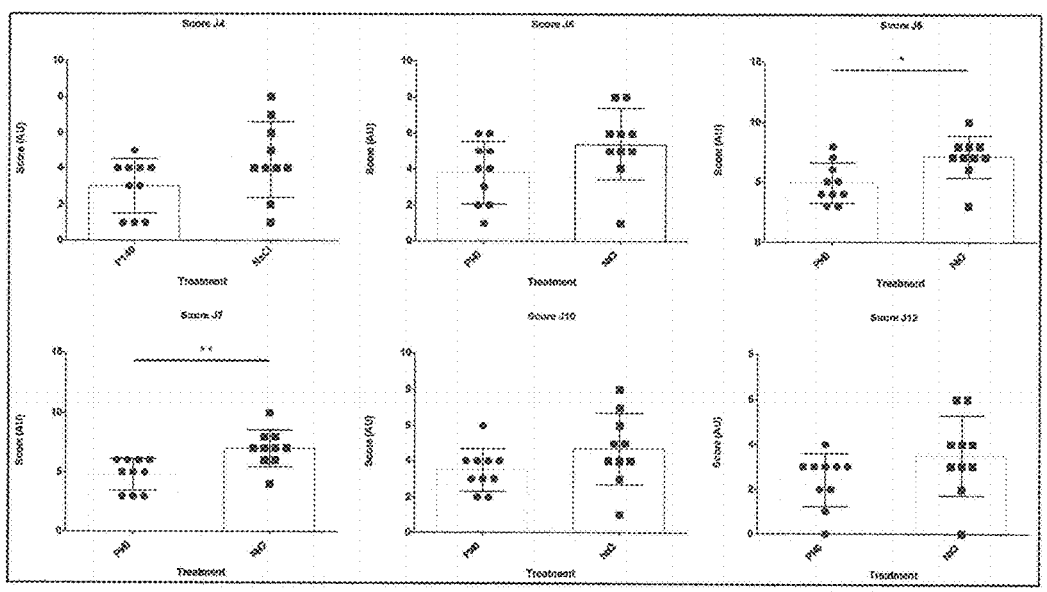
FIG. 35. Evolution of inflammation score overnight, P140/NaCl vs Lupuzor™.

The inflammation scores were calculated independently for each leg (rear legs and front left and right) and then added together to obtain a score of general inflammation for each mouse (FIG. 32). The score for control mice reached a maximum of around day 7 whereas mice treated do not exceed day 5. The framework was realized day 4 to day 12 has on both curves representing revolution of inflammation score (FIG. 32, and FIG. 35). The Two curves are significantly different: p=0.0156; * (Two way ANOVA) (FIG. 32).

In this study, demonstrate an important effect of the P140 peptide in the K/BxN model that mimics RA. All clinical signs (swelling joints, weight loss, appearance of inflammation score) tend to be attenuated.

In the preventive model and in a statistically significant manner, we find: a loss of less weight of treated mice and a return to normal faster; a lower inflammation in the paws and a limitation of their deformation; their inflammation score decreases sharply when the inflammation is at its maximum.

For the curative model, we cannot conclude on the effect of peptide P140, knowing that the induction of the disease has been very moderate or even zero.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating or ameliorating a chronic inflammatory or hyper-chaperone-mediated-autophagy(CMA)-related disease or disorder, the method comprising administering to a patient in need thereof a composition comprising an effective amount of at least one peptide selected from the group consisting of SEQ ID NO:1, 2, 4, 5 and a combination thereof, wherein at least one serine in the peptide is phosphorylated, wherein the chronic inflammatory or hyper CMA-related disease or disorder is selected from the group consisting of muscular dystrophy (MD), fibromyalgia, myopathies, chronic inflammatory demyelinating polyradiculoneuropathy (CIDP), asthma, chronic pulmonary obstructive disorder (COPD), eosinophilic airway inflammation, and psoriasis, and the composition is effective in treating or ameliorating at least one symptom of the chronic inflammatory or hyper CMA-related disease or disorder.

2. The method of claim 1, wherein said chronic inflammatory or hyper-CMA-related disease or disorder is MD.

3. The method of claim 1, wherein said chronic inflammatory or hyper-CMA-related disease or disorder is fibromyalgia.

4. The method of claim 1, wherein said chronic inflammatory or hyper-CMA-related disease or disorder is myopathies.

5. The method of claim 1, wherein said chronic inflammatory or hyper-CMA-related disease or disorder is eosinophilic airway inflammation.

6. The method of claim 1, wherein said chronic inflammatory or hyper-CMA-related disease or disorder is COPD.

7. The method of claim 1, wherein said chronic inflammatory or hyper-CMA-related disease or disorder is CIDP.

8. The method of claim 1, wherein said chronic inflammatory or hyper-CMA-related disease or disorder is asthma.

9. The method of claim 1, wherein said chronic inflammatory or hyper-CMA-related disease or disorder is psoriasis.

10. The method of claim 1, wherein the composition is administered at a dosage of from about 100 ng to about 5 mg.

11. The method of claim 10, wherein the composition further comprises a pharmaceutically acceptable excipient.

12. The method of claim 11, wherein the excipient is mannitol.

13. The method of claim 1, wherein the peptide comprises the amino acid sequence of SEQ ID NO:1 including a phosphoserine at position 10.

14. The method of claim 1, wherein the peptide comprises the amino acid sequence of SEQ ID NO:1 including a phosphoserine at position 10 and an oxidized methionine.

15. The method of claim 1, wherein the peptide has the structure:
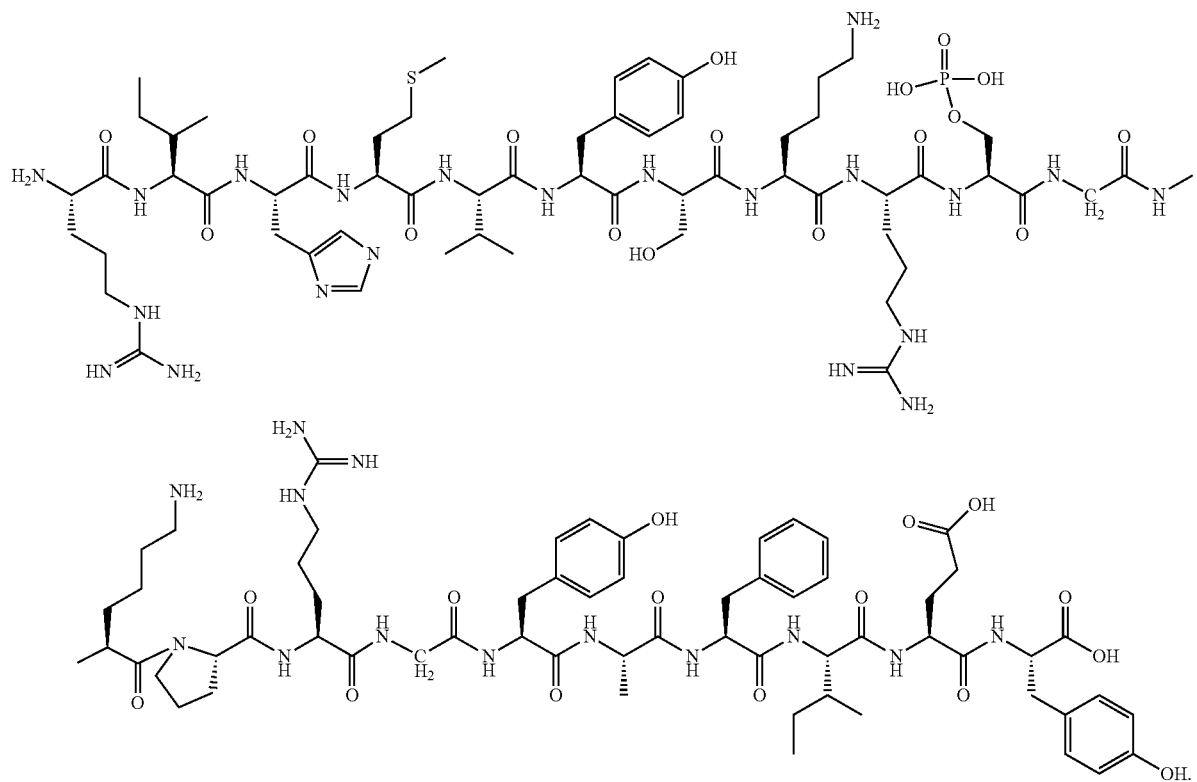
16. The method of claim 1, wherein the peptide has the structure:
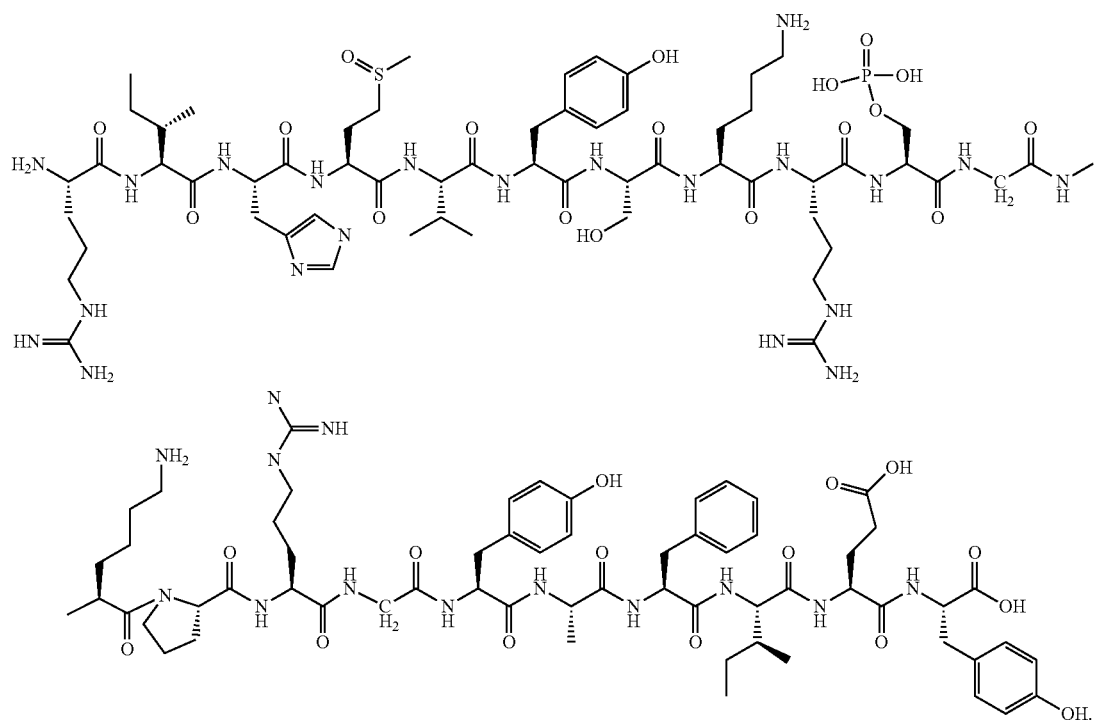
* * * * *